US012161668B2

(12) United States Patent
Maus et al.

(10) Patent No.: US 12,161,668 B2
(45) Date of Patent: Dec. 10, 2024

(54) T CELLS EXPRESSING A CHIMERIC ANTIGEN RECEPTOR

(71) Applicant: The General Hospital Corporation, Boston, MA (US)

(72) Inventors: Marcela V. Maus, Lexington, MA (US); Bryan Choi, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 313 days.

(21) Appl. No.: 16/476,595

(22) PCT Filed: Jan. 10, 2018

(86) PCT No.: PCT/US2018/013221
§ 371 (c)(1),
(2) Date: Jul. 9, 2019

(87) PCT Pub. No.: WO2018/132513
PCT Pub. Date: Jul. 19, 2018

(65) Prior Publication Data
US 2019/0328787 A1    Oct. 31, 2019

Related U.S. Application Data

(60) Provisional application No. 62/580,258, filed on Nov. 1, 2017, provisional application No. 62/516,279, filed on Jun. 7, 2017, provisional application No. 62/444,622, filed on Jan. 10, 2017.

(51) Int. Cl.
*C07K 14/705* (2006.01)
*A61K 35/17* (2015.01)
*A61P 35/00* (2006.01)
*C07K 14/725* (2006.01)
*A61K 45/06* (2006.01)

(52) U.S. Cl.
CPC .............. *A61K 35/17* (2013.01); *A61P 35/00* (2018.01); *C07K 14/7051* (2013.01); *C07K 14/70517* (2013.01); *C07K 14/70575* (2013.01); *C07K 14/70578* (2013.01); *A61K 45/06* (2013.01)

(58) Field of Classification Search
CPC .................................................. C07K 14/705
See application file for complete search history.

(56) References Cited

U.S. PATENT DOCUMENTS

| 10,570,186 B2 | 2/2020 | Cooper et al. | |
| 10,774,343 B2 | 9/2020 | Morgan et al. | |
| 2004/0043401 A1 | 3/2004 | Sadelain et al. | |
| 2004/0127410 A1 | 7/2004 | McWherter et al. | |
| 2006/0003407 A1* | 1/2006 | Rennert et al. ......... | C07H 21/04 435/69.1 |
| 2010/0105136 A1* | 4/2010 | Carter et al. ......... | C12N 5/0783 435/372.3 |
| 2013/0266551 A1 | 10/2013 | Campana et al. | |
| 2013/0280220 A1 | 10/2013 | Ahmed et al. | |
| 2014/0271635 A1* | 9/2014 | Brogdon et al. ... | C07K 16/2896 424/133.1 |
| 2014/0322275 A1 | 10/2014 | Brogdon et al. | |
| 2015/0306141 A1* | 10/2015 | Jensen et al. .......... | A61K 35/17 |
| 2015/0368342 A1 | 12/2015 | Wu et al. | |
| 2016/0237139 A1* | 8/2016 | Pule et al. ....... | C07K 14/70578 |
| 2016/0289294 A1* | 10/2016 | Puléet al. ......... | C07K 14/70503 |
| 2017/0267739 A1 | 9/2017 | Berger et al. | |
| 2021/0054086 A1 | 2/2021 | Maus et al. | |

FOREIGN PATENT DOCUMENTS

| WO | WO 2013/123061 A1 | 8/2013 | |
| WO | WO-2015/052538 A1 | 4/2015 | |
| WO | WO 2015/075468 A1 | 5/2015 | |
| WO | WO 2015/075469 A1 | 5/2015 | |
| WO | WO 2015/075470 A1 | 5/2015 | |
| WO | WO 2015/077789 A2 | 5/2015 | |
| WO | WO 2015/077789 A3 | 8/2015 | |
| WO | WO 2016/112983 A1 | 7/2016 | |
| WO | WO-2016/174405 A1 | 11/2016 | |
| WO | WO 2017/140632 A1 | 8/2017 | |
| WO | WO2017222593 A1 * | 12/2017 | ............. A61K 35/17 |
| WO | WO 2018/132513 A1 | 7/2018 | |
| WO | WO 2019/140127 A2 | 7/2019 | |

(Continued)

OTHER PUBLICATIONS

Guedan et al. (Mar. 2019) "Engineering and Design of Chimeric Antigen Receptors" Molecular Therapy-Methods & Clinical Development, 12, 145-156. (Year: 2019).*
Accession No. NP_001552.2, tumor necrosis factor receptor superfamily member 9 precursor [*Homo sapiens*], National Library of Medicine (US): National Center for Biotechnology Information, revision date: Oct. 7, 2016. (Year: 2016).*
International Search Report and Written Opinion for International Application No. PCT/US18/13221, mailed May 29, 2018 (19 pages).
International Preliminary Report on Patentability for International Application No. PCT/US2018/013221 issued Jul. 16, 2019 (9 pages).

(Continued)

*Primary Examiner* — Teresa E Knight
*Assistant Examiner* — James Joseph Graber
(74) *Attorney, Agent, or Firm* — Wolf, Greenfield & Sacks, P.C.

(57) ABSTRACT

Described herein are methods for producing and utilizing T cells comprising chimeric antigen receptors (CAR) comprising a portion of the extracellular domain of a Tumor Necrosis Factor (TNF) superfamily receptor ligand, e.g., A PRoliferation-Inducing Ligand (APRIL). The CAR T cells of this present invention overcome resistance to anti-BCMA targeted therapies and utilize dimerizing and trimerizing transmembrane domains for optimal function. Further, this invention is related to methods of treating cancer, plasma cell diseases or disorders, or autoimmune diseases or disorders.

18 Claims, 14 Drawing Sheets

Specification includes a Sequence Listing.

(56) References Cited

FOREIGN PATENT DOCUMENTS

WO  WO 2019/140127 A3  8/2019

OTHER PUBLICATIONS

Schmidts et al., "Engineering an Optimized Trimeric APRIL-Based CAR to Broaden Targetability of Multiple Myeloma," Blood. 132:2059 (2018) (Abstract) (5 pages).

UniProtKB Accession No. Q6U617, Jul. 5, 2004, available <https://www.uniprot.org/uniprot/Q6U617.txt>, (1 page).

International Search Report and Written Opinion for International Patent Application No. PCT/US2019/013103, mailed Jul. 10, 2019 (22 pages).

Bielamowicz et al., Trivalent CAR T cells overcome interpatient antigenic variability in glioblastoma. Neuro Oncol. Mar. 27, 2018;20(4):506-518. doi: 10.1093/neuonc/nox182.

Schmidts et al., Rational design of a trimeric APRIL-based CAR-binding domain enables efficient targeting of multiple myeloma. Blood Adv. Nov. 12, 2019;3(21):3248-3260. doi: 10.1182/bloodadvances.2019000703.

Vincent et al., The BAFF/APRIL system: emerging functions beyond B cell biology and autoimmunity. Cytokine Growth Factor Rev. Jun. 2013;24(3):203-15. doi: 10.1016/j.cytogfr.2013.04.003. Epub May 15, 2013.

Extended European Search Report for Application No. EP19738635.2, mailed Oct. 4, 2021.

Schmidts et al., Rational design of a trimeric APRIL-based CAR-binding domain enables efficient targeting of multiple myeloma. Blood Adv. Nov. 12, 2019;3(21):3248-3260. doi: 10.1182/bloodadvances.2019000703. Supplemental Information, 11 pages.

Chen et al., Recent Advances in Diagnosis and Treatment of Gynecologic Tumors, 2nd Edition. People's Army Medical Press. Sep. 30, 2015. p. 401.

Geldres et al., Chimeric antigen receptor-redirected T cells return to the bench. Semin Immunol. Feb. 2016;28(1):3-9. doi: 10.1016/j.smim.2015.12.001. Epub Jan. 12, 2016.

Wang et al., Current development of chimeric antigen receptor T-cell therapy. Stem Cell Investig. Dec. 3, 2018:5:44. doi: 10.21037/sci.2018.11.05. eCollection 2018.

\* cited by examiner

SEQUENCE LISTING

<160> NUMBER OF SEQ ID NOS: 38

<210> SEQ ID NO 1
<211> LENGTH: 1140
<212> TYPE: DNA
<213> ORGANISM: Artificial Sequence
<220> FEATURE:
<223> OTHER INFORMATION: Synthetic Construct

<400> SEQUENCE: 1
atggccctcc ctgtcaccgc cctgctgctt ccgctggctc ttctgctcca cgccgctcgg      60

```
ccccactctg tcctgcacct ggttcccatt aacgccacct ccaaggatga ctccgatgtg    120
acagaggtga tgtggcaacc agctcttagg cgtgggagag gcctacaggc ccaaggatat    180
ggtgtccgaa tccaggatgc tggagtttat ctgctgtata gccaggtcct gtttcaagac    240
gtgactttca ccatgggtca ggtggtgtct cgagaaggcc aaggaaggca ggagactcta    300
ttccgatgta taagaagtat gccctcccac ccggaccggg cctacaacag ctgctatagc    360
gcaggtgtct tccatttaca ccaaggggat attctgagtg tcataattcc cgggcaagg     420 gcgaaactta acctctctcc acatggaacc ttcctggggt tgtgaaact gaccactacc     480 ccagcaccga ggccacccac ccggctcct accatcgcct cccagcctct gtccctgcgt     540
ccggaggcat gtagacccgc agctggtggg gccgtgcata cccggggtct tgacttcgcc    600
tgcgatatct acatttgggc ccctctggct ggtacttgcg gggtcctgct gctttcactc    660
gtgatcactc tttactgtaa gcgcggtcgg aagaagctgc tgtacatctt taagcaaccc    720
ttcatgaggc ctgtgcagac tactcaagag gaggacggct gttcatgccg gttcccagag    780
gaggaggaag gcggctgcga actgcgcgtg aaattcagcc gcagcgcaga tgctccagcc    840
taccaacagg ggcagaacca gctctacaac gaactcaatc ttggtcggag agaggagtac    900
gacgtgctgg acaagcggag aggacgggac ccagaaatgg gcgggaagcc gcgcagaaag    960
aatccccaag agggcctgta caacgagctc caaaaggata agatggcaga agcctatagc   1020
gagattggta tgaaggggaa acgcagaaga ggcaaaggcc acgacggact gtaccaggga   1080
ctcagcaccg ccaccaagga cacctatgac gctcttcaca tgcaggccct gccgcctcgg   1140
```

<210> SEQ ID NO 2
<211> LENGTH: 63
<212> TYPE: DNA
<213> ORGANISM: Artificial Sequence
<220> FEATURE:
<223> OTHER INFORMATION: Synthetic Construct

<400> SEQUENCE: 2

```
atggccctcc ctgtcaccgc cctgctgctt ccgctggctc ttctgctcca cgccgctcgg     60
ccc                                                                   63
```

<210> SEQ ID NO 3
<211> LENGTH: 408
<212> TYPE: DNA
<213> ORGANISM: Artificial Sequence
<220> FEATURE:
<223> OTHER INFORMATION: Synthetic Construct

<400> SEQUENCE: 3

```
cactctgtcc tgcacctggt tcccattaac gccacctcca aggatgactc cgatgtgaca     60
gaggtgatgt ggcaaccagc tcttaggcgt gggagaggcc tacaggccca aggatatggt    120
gtccgaatcc aggatgctgg agtttatctg ctgtatagcc aggtcctgtt tcaagacgtg    180
actttcacca tgggtcaggt ggtgtctcga gaaggccaag gaaggcagga gactctattc    240
cgatgtataa gaagtatgcc ctcccacccg gaccgggcct acaacagctg ctatagcgca    300
ggtgtcttcc atttacacca aggggatatt ctgagtgtca taattcccgg gcaagggcg     360 aaacttaacc tctctccaca tggaaccttc ctggggtttg tgaaactg                408
```

<210> SEQ ID NO 4
<211> LENGTH: 207
<212> TYPE: DNA
<213> ORGANISM: Artificial Sequence

```
<220> FEATURE:
<223> OTHER INFORMATION: Synthetic Construct

<400> SEQUENCE: 4
accactaccc cagcaccgag gccacccacc ccggctccta ccatcgcctc ccagcctctg     60
tccctgcgtc cggaggcatg tagacccgca gctggtgggg ccgtgcatac ccggggtctt    120
gacttcgcct gcgatatcta catttgggcc cctctggctg gtacttgcgg ggtcctgctg    180
ctttcactcg tgatcactct ttactgt                                        207

<210> SEQ ID NO 5
<211> LENGTH: 126
<212> TYPE: DNA
<213> ORGANISM: Artificial Sequence
<220> FEATURE:
<223> OTHER INFORMATION: Synthetic Construct

<400> SEQUENCE: 5
aagcgcggtc ggaagaagct gctgtacatc tttaagcaac ccttcatgag gcctgtgcag     60
actactcaag aggaggacgg ctgttcatgc cggttcccag aggaggagga aggcggctgc    120
gaactg                                                               126

<210> SEQ ID NO 6
<211> LENGTH: 336
<212> TYPE: DNA
<213> ORGANISM: Artificial Sequence
<220> FEATURE:
<223> OTHER INFORMATION: Synthetic Construct

<400> SEQUENCE: 6
cgcgtgaaat tcagccgcag cgcagatgct ccagcctacc aacagggca gaaccagctc      60 tacaacgaac tcaatcttgg tcggagagag gagtacgacg tgctggacaa gcggagagga    120
cgggacccag aaatgggcgg gaagccgcgc agaaagaatc cccaagaggg cctgtacaac    180
gagctccaaa aggataagat ggcagaagcc tatagcgaga ttggtatgaa aggggaacgc    240
agaagaggca aggccacga cggactgtac cagggactca gcaccgccac caaggacacc    300
tatgacgctc ttcacatgca ggccctgccg cctcgg                              336

<210> SEQ ID NO 7
<211> LENGTH: 1095
<212> TYPE: DNA
<213> ORGANISM: Artificial Sequence
<220> FEATURE:
<223> OTHER INFORMATION: Synthetic Construct

<400> SEQUENCE: 7
atggccctcc ctgtcaccgc cctgctgctt ccgctggctc ttctgctcca cgccgctcgg     60
ccccactctg tcctgcacct ggttcccatt aacgccacct ccaaggatga ctccgatgtg    120
acagaggtga tgtggcaacc agctcttagg cgtgggagag gcctacaggc ccaaggatat    180
ggtgtccgaa tccaggatgc tggagtttat ctgctgtata gccaggtcct gtttcaagac    240
gtgactttca ccatgggtca ggtggtgtct cgagaaggcc aaggaaggca ggagactcta    300
ttccgatgta taagaagtat gccctcccac ccggaccggg cctacaacag ctgctatagc    360
gcaggtgtct tccatttaca ccaagggga ttctgagtg tcataattcc ccgggcaagg    420
gcgaaactta acctctctcc acatggaacc ttcctggggt ttgtgaaact gccatctcca    480
gccgacctct ctccgggagc atcctctgtg acccccgcctg cccctgcgag agagccagga    540
```

```
cactctccgc agatcatctc cttctttctt gcgctgacgt cgactgcgtt gctcttcctg    600
ctgttcttcc tcacgctccg tttctctgtt gttaagcgcg gtcggaagaa gctgctgtac    660
atctttaagc aaccccttcat gaggcctgtg cagactactc aagaggagga cggctgttca   720
tgccggttcc cagaggagga ggaaggcggc tgcgaactgc gcgtgaaatt cagccgcagc    780
gcagatgctc cagcctacca acaggggcag aaccagctct acaacgaact caatcttggt    840
cggagagagg agtacgacgt gctggacaag cggagaggac gggacccaga aatgggcggg    900
aagccgcgca gaaagaatcc ccaagagggc ctgtacaacg agctccaaaa ggataagatg    960
gcagaagcct atagcgagat tggtatgaaa ggggaacgca agagaggcaa aggccacgac    1020
ggactgtacc agggactcag caccgccacc aaggacacct atgacgctct tcacatgcag    1080
gccctgccgc ctcgg                                                     1095

<210> SEQ ID NO 8
<211> LENGTH: 63
<212> TYPE: DNA
<213> ORGANISM: Artificial Sequence
<220> FEATURE:
<223> OTHER INFORMATION: Synthetic Construct

<400> SEQUENCE: 8
atggccctcc ctgtcaccgc cctgctgctt ccgctggctc ttctgctcca cgccgctcgg    60
ccc                                                                  63

<210> SEQ ID NO 9
<211> LENGTH: 408
<212> TYPE: DNA
<213> ORGANISM: Artificial Sequence
<220> FEATURE:
<223> OTHER INFORMATION: Synthetic Construct

<400> SEQUENCE: 9
cactctgtcc tgcacctggt tcccattaac gccacctcca aggatgactc cgatgtgaca    60
gaggtgatgt ggcaaccagc tcttaggcgt gggagaggcc tacaggccca aggatatggt   120
gtccgaatcc aggatgctgg agtttatctg ctgtatagcc aggtcctgtt tcaagacgtg   180
actttcacca tgggtcaggt ggtgtctcga aaggccaag gaaggcagga gactctattc    240
cgatgtataa gaagtatgcc ctcccacccg gaccgggcct acaacagctg ctatagcgca   300
ggtgtcttcc atttacacca aggggatatt ctgagtgtca taattccccg gcaagggcg    360 aaacttaacc tctctccaca tggaaccttc ctggggtttg tgaaactg                408

<210> SEQ ID NO 10
<211> LENGTH: 162
<212> TYPE: DNA
<213> ORGANISM: Artificial Sequence
<220> FEATURE:
<223> OTHER INFORMATION: Synthetic Construct

<400> SEQUENCE: 10
ccatctccag ccgacctctc tccgggagca tcctctgtga ccccgcctgc ccctgcgaga    60
gagccaggac actctccgca gatcatctcc ttctttcttg cgctgacgtc gactgcgttg   120
ctcttcctgc tgttcttcct cacgctccgt ttctctgttg tt                      162

<210> SEQ ID NO 11
<211> LENGTH: 126
<212> TYPE: DNA
<213> ORGANISM: Artificial Sequence
```

```
<220> FEATURE:
<223> OTHER INFORMATION: Synthetic Construct

<400> SEQUENCE: 11
aagcgcggtc ggaagaagct gctgtacatc tttaagcaac ccttcatgag gcctgtgcag      60
actactcaag aggaggacgg ctgttcatgc cggttcccag aggaggagga aggcggctgc     120
gaactg                                                                126

<210> SEQ ID NO 12
<211> LENGTH: 336
<212> TYPE: DNA
<213> ORGANISM: Artificial Sequence
<220> FEATURE:
<223> OTHER INFORMATION: Synthetic Construct

<400> SEQUENCE: 12
cgcgtgaaat tcagccgcag cgcagatgct ccagcctacc aacagggca gaaccagctc       60 tacaacgaac tcaatcttgg tcggagagag gagtacgacg tgctggacaa gcggagagga    120
cgggacccag aaatgggcgg gaagccgcgc agaaagaatc cccaagaggg cctgtacaac    180
gagctccaaa aggataagat ggcagaagcc tatagcgaga ttggtatgaa aggggaacgc    240
agaagaggca aaggccacga cggactgtac cagggactca gcaccgccac caaggacacc    300
tatgacgctc ttcacatgca ggccctgccg cctcgg                              336

<210> SEQ ID NO 13
<211> LENGTH: 1200
<212> TYPE: DNA
<213> ORGANISM: Artificial Sequence
<220> FEATURE:
<223> OTHER INFORMATION: Synthetic Construct

<400> SEQUENCE: 13
atggccctcc ctgtcaccgc cctgctgctt ccgctggctc ttctgctcca cgccgctcgg       60
ccccactctg tcctgcacct ggttcccatt aacgccaccc caaggatga ctccgatgtg     120 acagaggtga tgtggcaacc agctcttagg cgtgggagag gcctacaggc ccaaggatat    180
ggtgtccgaa tccaggatgc tggagtttat ctgctgtata gccaggtcct gtttcaagac    240
gtgactttca ccatgggtca ggtggtgtct cgagaaggcc aaggaaggca ggagactcta    300
ttccgatgta taagaagtat gccctccac ccggaccggg cctacaacag ctgctatagc    360
gcaggtgtct tccatttaca ccaaggggat attctgagtg tcataattcc ccgggcaagg    420
gcgaaactta acctctctcc acatggaacc ttcctggggt tgtgaaact gccatctcca    480 gccgacctct ctccgggagc atcctctgtg accccgcctg cccctgcgag agagccagga    540
cactctccgc agatcatctc cttctttctt gcgctgacgt cgactgcgtt gctcttcctg    600
ctgttcttcc tcacgctccg tttctctgtt gttaagcgcg tcggaagaa gctgctgtac    660 atctttaagc aacccttcat gaggcctgtg cagactactc aagaggagga cggctgttca    720
tgccggttcc cagaggagga ggaaggcggc tgcgaactgc gcgtgaaatt cagccgcagc    780
gcagatgctc cagcctacca acaggggcag aaccagctct acaacgaact caatcttggt    840
cggagagagg agtacgacgt gctggacaag cggagaggac gggacccaga aatgggcggg    900
aagccgcgca gaaagaatcc ccaagagggc ctgtacaacg agctccaaaa ggataagatg    960
gcagaagcct atagcgagat tggtatgaaa ggggaacgca agagaggcaa aggccacgac   1020
ggactgtacc aggacagcca cttccaagca gttccagtac aggaaaagaa aaaaaggctc   1080
```
agaagggcac cgtggcgtgc attcgcccag ccccagaggt taaagcaccg aaacaatgaa    1140
ctacctgact ccctagagcc catatataaa aacatttgga acaaaacatt tataggagag    1200

<210> SEQ ID NO 14
<211> LENGTH: 63
<212> TYPE: DNA
<213> ORGANISM: Artificial Sequence
<220> FEATURE:
<223> OTHER INFORMATION: Synthetic Construct

<400> SEQUENCE: 14
atggccctcc ctgtcaccgc cctgctgctt ccgctggctc ttctgctcca cgccgctcgg     60
ccc                                                                  63

<210> SEQ ID NO 15
<211> LENGTH: 408
<212> TYPE: DNA
<213> ORGANISM: Artificial Sequence
<220> FEATURE:
<223> OTHER INFORMATION: Synthetic Construct

<400> SEQUENCE: 15
cactctgtcc tgcacctggt tcccattaac gccacctcca aggatgactc cgatgtgaca     60
gaggtgatgt ggcaaccagc tcttaggcgt gggagaggcc tacaggccca aggatatggt    120
gtccgaatcc aggatgctgg agtttatctg ctgtatagcc aggtcctgtt tcaagacgtg    180
actttcacca tgggtcaggt ggtgtctcga aaggccaag gaaggcagga gactctattc     240
cgatgtataa gaagtatgcc ctcccacccg gaccgggcct acaacagctg ctatagcgca    300
ggtgtcttcc atttacacca aggggatatt ctgagtgtca taattccccg ggcaagggcg    360
aaacttaacc tctctccaca tggaaccttc ctggggtttg tgaaactg                 408

<210> SEQ ID NO 16
<211> LENGTH: 162
<212> TYPE: DNA
<213> ORGANISM: Artificial Sequence
<220> FEATURE:
<223> OTHER INFORMATION: Synthetic Construct

<400> SEQUENCE: 16
ccatctccag ccgacctctc tccgggagca tcctctgtga ccccgcctgc ccctgcgaga     60
gagccaggac actctccgca gatcatctcc ttctttcttg cgctgacgtc gactgcgttg    120
ctcttcctgc tgttcttcct cacgctccgt ttctctgttg tt                      162

<210> SEQ ID NO 17
<211> LENGTH: 126
<212> TYPE: DNA
<213> ORGANISM: Artificial Sequence
<220> FEATURE:
<223> OTHER INFORMATION: Synthetic Construct

<400> SEQUENCE: 17
aagcgcggtc ggaagaagct gctgtacatc tttaagcaac ccttcatgag gcctgtgcag     60
actactcaag aggaggacgg ctgttcatgc cggttcccag aggaggagga aggcggctgc    120
gaactg                                                              126

<210> SEQ ID NO 18
<211> LENGTH: 441
<212> TYPE: DNA
<213> ORGANISM: Artificial Sequence

```
<220> FEATURE:
<223> OTHER INFORMATION: Synthetic Construct

<400> SEQUENCE: 18
cgcgtgaaat tcagccgcag cgcagatgct ccagcctacc aacaggggca gaaccagctc      60
tacaacgaac tcaatcttgg tcggagagag gagtacgacg tgctggacaa gcggagagga     120
cgggacccag aaatgggcgg gaagccgcgc agaaagaatc cccaagaggg cctgtacaac     180
gagctccaaa aggataagat ggcagaagcc tatagcgaga ttggtatgaa aggggaacgc     240
agaagaggca aggccacga cggactgtac caggacagcc acttccaagc agttccagta     300
caggaaaaga aaaaaaggct cagaagggca ccgtggcgtg cattcgccca gccccagagg     360
ttaaagcacc gaaacaatga actacctgac tccctagagc ccatatataa aacatttgg     420 aacaaaacat ttataggaga g                                               441

<210> SEQ ID NO 19
<211> LENGTH: 380
<212> TYPE: PRT
<213> ORGANISM: Artificial Sequence
<220> FEATURE:
<223> OTHER INFORMATION: Synthetic Construct

<400> SEQUENCE: 19
```

Met Ala Leu Pro Val Thr Ala Leu Leu Leu Pro Leu Ala Leu Leu Leu
1               5                   10                  15

His Ala Ala Arg Pro His Ser Val Leu His Leu Val Pro Ile Asn Ala
                20                  25                  30

Thr Ser Lys Asp Asp Ser Asp Val Thr Glu Val Met Trp Gln Pro Ala
            35                  40                  45

Leu Arg Arg Gly Arg Gly Leu Gln Ala Gln Gly Tyr Gly Val Arg Ile
        50                  55                  60

Gln Asp Ala Gly Val Tyr Leu Leu Tyr Ser Gln Val Leu Phe Gln Asp
65                  70                  75                  80

Val Thr Phe Thr Met Gly Gln Val Val Ser Arg Glu Gly Gln Gly Arg
                85                  90                  95

Gln Glu Thr Leu Phe Arg Cys Ile Arg Ser Met Pro Ser His Pro Asp
                100                 105                 110

Arg Ala Tyr Asn Ser Cys Tyr Ser Ala Gly Val Phe His Leu His Gln
            115                 120                 125

Gly Asp Ile Leu Ser Val Ile Ile Pro Arg Ala Arg Ala Lys Leu Asn
        130                 135                 140

Leu Ser Pro His Gly Thr Phe Leu Gly Phe Val Lys Leu Thr Thr Thr
145                 150                 155                 160

Pro Ala Pro Arg Pro Pro Thr Pro Ala Pro Thr Ile Ala Ser Gln Pro
                165                 170                 175

Leu Ser Leu Arg Pro Glu Ala Cys Arg Pro Ala Ala Gly Gly Ala Val
            180                 185                 190

His Thr Arg Gly Leu Asp Phe Ala Cys Asp Ile Tyr Ile Trp Ala Pro
        195                 200                 205

Leu Ala Gly Thr Cys Gly Val Leu Leu Leu Ser Leu Val Ile Thr Leu
    210                 215                 220

Tyr Cys Lys Arg Gly Arg Lys Lys Leu Leu Tyr Ile Phe Lys Gln Pro
225                 230                 235                 240

Phe Met Arg Pro Val Gln Thr Thr Gln Glu Glu Asp Gly Cys Ser Cys
                245                 250                 255

```
Arg Phe Pro Glu Glu Glu Gly Gly Cys Glu Leu Arg Val Lys Phe
            260                 265                 270

Ser Arg Ser Ala Asp Ala Pro Tyr Gln Gln Gly Gln Asn Gln Leu
        275                 280                 285

Tyr Asn Glu Leu Asn Leu Gly Arg Arg Glu Tyr Asp Val Leu Asp
    290                 295                 300

Lys Arg Arg Gly Arg Asp Pro Glu Met Gly Gly Lys Pro Arg Arg Lys
305                 310                 315                 320

Asn Pro Gln Glu Gly Leu Tyr Asn Glu Leu Gln Lys Asp Lys Met Ala
                325                 330                 335

Glu Ala Tyr Ser Glu Ile Gly Met Lys Gly Glu Arg Arg Gly Lys
            340                 345                 350

Gly His Asp Gly Leu Tyr Gln Gly Leu Ser Thr Ala Thr Lys Asp Thr
            355                 360                 365

Tyr Asp Ala Leu His Met Gln Ala Leu Pro Pro Arg
    370                 375                 380

<210> SEQ ID NO 20
<211> LENGTH: 21
<212> TYPE: PRT
<213> ORGANISM: Artificial Sequence
<220> FEATURE:
<223> OTHER INFORMATION: Synthetic Construct

<400> SEQUENCE: 20

Met Ala Leu Pro Val Thr Ala Leu Leu Leu Pro Leu Ala Leu Leu Leu
1               5                   10                  15

His Ala Ala Arg Pro
            20

<210> SEQ ID NO 21
<211> LENGTH: 136
<212> TYPE: PRT
<213> ORGANISM: Artificial Sequence
<220> FEATURE:
<223> OTHER INFORMATION: Synthetic Construct

<400> SEQUENCE: 21

His Ser Val Leu His Leu Val Pro Ile Asn Ala Thr Ser Lys Asp Asp
1               5                   10                  15

Ser Asp Val Thr Glu Val Met Trp Gln Pro Ala Leu Arg Arg Gly Arg
            20                  25                  30

Gly Leu Gln Ala Gln Gly Tyr Gly Val Arg Ile Gln Asp Ala Gly Val
        35                  40                  45

Tyr Leu Leu Tyr Ser Gln Val Leu Phe Gln Asp Val Thr Phe Thr Met
    50                  55                  60

Gly Gln Val Val Ser Arg Glu Gly Gln Gly Arg Gln Glu Thr Leu Phe
65                  70                  75                  80

Arg Cys Ile Arg Ser Met Pro Ser His Pro Asp Arg Ala Tyr Asn Ser
                85                  90                  95

Cys Tyr Ser Ala Gly Val Phe His Leu His Gln Gly Asp Ile Leu Ser
            100                 105                 110

Val Ile Ile Pro Arg Ala Arg Ala Lys Leu Asn Leu Ser Pro His Gly
        115                 120                 125

Thr Phe Leu Gly Phe Val Lys Leu
    130                 135

<210> SEQ ID NO 22
```

```
<211> LENGTH: 69
<212> TYPE: PRT
<213> ORGANISM: Artificial Sequence
<220> FEATURE:
<223> OTHER INFORMATION: Synthetic Construct

<400> SEQUENCE: 22

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 23
<211> LENGTH: 42
<212> TYPE: PRT
<213> ORGANISM: Artificial Sequence
<220> FEATURE:
<223> OTHER INFORMATION: Synthetic Construct

<400> SEQUENCE: 23

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 24
<211> LENGTH: 112
<212> TYPE: PRT
<213> ORGANISM: Artificial Sequence
<220> FEATURE:
<223> OTHER INFORMATION: Synthetic Construct

<400> SEQUENCE: 24

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 25
<211> LENGTH: 365
<212> TYPE: PRT
<213> ORGANISM: Artificial Sequence
<220> FEATURE:
```

<223> OTHER INFORMATION: Synthetic Construct

<400> SEQUENCE: 25

```
Met Ala Leu Pro Val Thr Ala Leu Leu Leu Pro Leu Ala Leu Leu Leu
1               5                   10                  15

His Ala Ala Arg Pro His Ser Val Leu His Leu Val Pro Ile Asn Ala
            20                  25                  30

Thr Ser Lys Asp Asp Ser Asp Val Thr Glu Val Met Trp Gln Pro Ala
        35                  40                  45

Leu Arg Arg Gly Arg Gly Leu Gln Ala Gln Gly Tyr Gly Val Arg Ile
    50                  55                  60

Gln Asp Ala Gly Val Tyr Leu Leu Tyr Ser Gln Val Leu Phe Gln Asp
65                  70                  75                  80

Val Thr Phe Thr Met Gly Gln Val Val Ser Arg Glu Gly Gln Gly Arg
                85                  90                  95

Gln Glu Thr Leu Phe Arg Cys Ile Arg Ser Met Pro Ser His Pro Asp
            100                 105                 110

Arg Ala Tyr Asn Ser Cys Tyr Ser Ala Gly Val Phe His Leu His Gln
        115                 120                 125

Gly Asp Ile Leu Ser Val Ile Ile Pro Arg Ala Arg Ala Lys Leu Asn
    130                 135                 140

Leu Ser Pro His Gly Thr Phe Leu Gly Phe Val Lys Leu Pro Ser Pro
145                 150                 155                 160

Ala Asp Leu Ser Pro Gly Ala Ser Ser Val Thr Pro Ala Pro Ala
                165                 170                 175

Arg Glu Pro Gly His Ser Pro Gln Ile Ile Ser Phe Phe Leu Ala Leu
            180                 185                 190

Thr Ser Thr Ala Leu Leu Phe Leu Leu Phe Phe Leu Thr Leu Arg Phe
        195                 200                 205

Ser Val Val Lys Arg Gly Arg Lys Lys Leu Leu Tyr Ile Phe Lys Gln
    210                 215                 220

Pro Phe Met Arg Pro Val Gln Thr Thr Gln Glu Glu Asp Gly Cys Ser
225                 230                 235                 240

Cys Arg Phe Pro Glu Glu Glu Glu Gly Gly Cys Glu Leu Arg Val Lys
                245                 250                 255

Phe Ser Arg Ser Ala Asp Ala Pro Ala Tyr Gln Gln Gly Gln Asn Gln
            260                 265                 270

Leu Tyr Asn Glu Leu Asn Leu Gly Arg Arg Glu Glu Tyr Asp Val Leu
        275                 280                 285

Asp Lys Arg Arg Gly Arg Asp Pro Glu Met Gly Gly Lys Pro Arg Arg
    290                 295                 300

Lys Asn Pro Gln Glu Gly Leu Tyr Asn Glu Leu Gln Lys Asp Lys Met
305                 310                 315                 320

Ala Glu Ala Tyr Ser Glu Ile Gly Met Lys Gly Glu Arg Arg Arg Gly
                325                 330                 335

Lys Gly His Asp Gly Leu Tyr Gln Gly Leu Ser Thr Ala Thr Lys Asp
            340                 345                 350

Thr Tyr Asp Ala Leu His Met Gln Ala Leu Pro Pro Arg
        355                 360                 365
```

<210> SEQ ID NO 26
<211> LENGTH: 21
<212> TYPE: PRT
<213> ORGANISM: Artificial Sequence
<220> FEATURE:

<223> OTHER INFORMATION: Synthetic Construct

<400> SEQUENCE: 26

Met Ala Leu Pro Val Thr Ala Leu Leu Leu Pro Leu Ala Leu Leu Leu
1               5                   10                  15

His Ala Ala Arg Pro
            20

<210> SEQ ID NO 27
<211> LENGTH: 136
<212> TYPE: PRT
<213> ORGANISM: Artificial Sequence
<220> FEATURE:
<223> OTHER INFORMATION: Synthetic Construct

<400> SEQUENCE: 27

His Ser Val Leu His Leu Val Pro Ile Asn Ala Thr Ser Lys Asp Asp
1               5                   10                  15

Ser Asp Val Thr Glu Val Met Trp Gln Pro Ala Leu Arg Arg Gly Arg
            20                  25                  30

Gly Leu Gln Ala Gln Gly Tyr Gly Val Arg Ile Gln Asp Ala Gly Val
        35                  40                  45

Tyr Leu Leu Tyr Ser Gln Val Leu Phe Gln Asp Val Thr Phe Thr Met
    50                  55                  60

Gly Gln Val Val Ser Arg Glu Gly Gln Gly Arg Gln Glu Thr Leu Phe
65                  70                  75                  80

Arg Cys Ile Arg Ser Met Pro Ser His Pro Asp Arg Ala Tyr Asn Ser
                85                  90                  95

Cys Tyr Ser Ala Gly Val Phe His Leu His Gln Gly Asp Ile Leu Ser
            100                 105                 110

Val Ile Ile Pro Arg Ala Arg Ala Lys Leu Asn Leu Ser Pro His Gly
        115                 120                 125

Thr Phe Leu Gly Phe Val Lys Leu
    130                 135

<210> SEQ ID NO 28
<211> LENGTH: 54
<212> TYPE: PRT
<213> ORGANISM: Artificial Sequence
<220> FEATURE:
<223> OTHER INFORMATION: Synthetic Construct

<400> SEQUENCE: 28

Pro Ser Pro Ala Asp Leu Ser Pro Gly Ala Ser Ser Val Thr Pro Pro
1               5                   10                  15

Ala Pro Ala Arg Glu Pro Gly His Ser Pro Gln Ile Ile Ser Phe Phe
            20                  25                  30

Leu Ala Leu Thr Ser Thr Ala Leu Leu Phe Leu Leu Phe Phe Leu Thr
        35                  40                  45

Leu Arg Phe Ser Val Val
    50

<210> SEQ ID NO 29
<211> LENGTH: 42
<212> TYPE: PRT
<213> ORGANISM: Artificial Sequence
<220> FEATURE:
<223> OTHER INFORMATION: Synthetic Construct

<400> SEQUENCE: 29

```
Lys Arg Gly Arg Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40
```

<210> SEQ ID NO 30
<211> LENGTH: 112
<212> TYPE: PRT
<213> ORGANISM: Artificial Sequence
<220> FEATURE:
<223> OTHER INFORMATION: Synthetic Construct

<400> SEQUENCE: 30

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
            100                 105                 110
```

<210> SEQ ID NO 31
<211> LENGTH: 400
<212> TYPE: PRT
<213> ORGANISM: Artificial Sequence
<220> FEATURE:
<223> OTHER INFORMATION: Synthetic Construct

<400> SEQUENCE: 31

```
Met Ala Leu Pro Val Thr Ala Leu Leu Leu Pro Leu Ala Leu Leu Leu
1               5                   10                  15

His Ala Ala Arg Pro His Ser Val Leu His Leu Val Pro Ile Asn Ala
            20                  25                  30

Thr Ser Lys Asp Asp Ser Asp Val Thr Glu Val Met Trp Gln Pro Ala
            35                  40                  45

Leu Arg Arg Gly Arg Gly Leu Gln Ala Gln Gly Tyr Gly Val Arg Ile
        50                  55                  60

Gln Asp Ala Gly Val Tyr Leu Leu Tyr Ser Gln Val Leu Phe Gln Asp
65                  70                  75                  80

Val Thr Phe Thr Met Gly Gln Val Val Ser Arg Glu Gly Gln Gly Arg
            85                  90                  95

Gln Glu Thr Leu Phe Arg Cys Ile Arg Ser Met Pro Ser His Pro Asp
            100                 105                 110

Arg Ala Tyr Asn Ser Cys Tyr Ser Ala Gly Val Phe His Leu His Gln
            115                 120                 125

Gly Asp Ile Leu Ser Val Ile Ile Pro Arg Ala Arg Ala Lys Leu Asn
        130                 135                 140

Leu Ser Pro His Gly Thr Phe Leu Gly Phe Val Lys Leu Pro Ser Pro
145                 150                 155                 160
```

```
Ala Asp Leu Ser Pro Gly Ala Ser Ser Val Thr Pro Pro Ala Pro Ala
            165                 170                 175

Arg Glu Pro Gly His Ser Pro Gln Ile Ile Ser Phe Phe Leu Ala Leu
        180                 185                 190

Thr Ser Thr Ala Leu Leu Phe Leu Leu Phe Phe Leu Thr Leu Arg Phe
            195                 200                 205

Ser Val Val Lys Arg Gly Arg Lys Lys Leu Leu Tyr Ile Phe Lys Gln
        210                 215                 220

Pro Phe Met Arg Pro Val Gln Thr Thr Gln Glu Glu Asp Gly Cys Ser
225                 230                 235                 240

Cys Arg Phe Pro Glu Glu Glu Gly Gly Cys Glu Leu Arg Val Lys
                245                 250                 255

Phe Ser Arg Ser Ala Asp Ala Pro Ala Tyr Gln Gln Gly Gln Asn Gln
                260                 265                 270

Leu Tyr Asn Glu Leu Asn Leu Gly Arg Arg Glu Glu Tyr Asp Val Leu
            275                 280                 285

Asp Lys Arg Arg Gly Arg Asp Pro Glu Met Gly Gly Lys Pro Arg Arg
        290                 295                 300

Lys Asn Pro Gln Glu Gly Leu Tyr Asn Glu Leu Gln Lys Asp Lys Met
305                 310                 315                 320

Ala Glu Ala Tyr Ser Glu Ile Gly Met Lys Gly Glu Arg Arg Arg Gly
                325                 330                 335

Lys Gly His Asp Gly Leu Tyr Gln Asp Ser His Phe Gln Ala Val Pro
            340                 345                 350

Val Gln Glu Lys Lys Arg Leu Arg Arg Ala Pro Trp Arg Ala Phe
        355                 360                 365

Ala Gln Pro Gln Arg Leu Lys His Arg Asn Asn Glu Leu Pro Asp Ser
        370                 375                 380

Leu Glu Pro Ile Tyr Lys Asn Ile Trp Asn Lys Thr Phe Ile Gly Glu
385                 390                 395                 400

<210> SEQ ID NO 32
<211> LENGTH: 21
<212> TYPE: PRT
<213> ORGANISM: Artificial Sequence
<220> FEATURE:
<223> OTHER INFORMATION: Synthetic Construct

<400> SEQUENCE: 32

Met Ala Leu Pro Val Thr Ala Leu Leu Leu Pro Leu Ala Leu Leu Leu
1               5                   10                  15

His Ala Ala Arg Pro
            20

<210> SEQ ID NO 33
<211> LENGTH: 136
<212> TYPE: PRT
<213> ORGANISM: Artificial Sequence
<220> FEATURE:
<223> OTHER INFORMATION: Synthetic Construct

<400> SEQUENCE: 33

His Ser Val Leu His Leu Val Pro Ile Asn Ala Thr Ser Lys Asp Asp
1               5                   10                  15

Ser Asp Val Thr Glu Val Met Trp Gln Pro Ala Leu Arg Arg Gly Arg
            20                  25                  30

Gly Leu Gln Ala Gln Gly Tyr Gly Val Arg Ile Gln Asp Ala Gly Val
```

```
                35                  40                  45
Tyr Leu Leu Tyr Ser Gln Val Leu Phe Gln Asp Val Thr Phe Thr Met
 50                  55                  60
Gly Gln Val Val Ser Arg Glu Gly Gln Gly Arg Gln Glu Thr Leu Phe
 65                  70                  75                  80
Arg Cys Ile Arg Ser Met Pro Ser His Pro Asp Arg Ala Tyr Asn Ser
                 85                  90                  95
Cys Tyr Ser Ala Gly Val Phe His Leu His Gln Gly Asp Ile Leu Ser
                100                 105                 110
Val Ile Ile Pro Arg Ala Arg Ala Lys Leu Asn Leu Ser Pro His Gly
            115                 120                 125
Thr Phe Leu Gly Phe Val Lys Leu
            130                 135

<210> SEQ ID NO 34
<211> LENGTH: 54
<212> TYPE: PRT
<213> ORGANISM: Artificial Sequence
<220> FEATURE:
<223> OTHER INFORMATION: Synthetic Construct

<400> SEQUENCE: 34

Pro Ser Pro Ala Asp Leu Ser Pro Gly Ala Ser Ser Val Thr Pro Pro
 1               5                  10                  15
Ala Pro Ala Arg Glu Pro Gly His Ser Pro Gln Ile Ile Ser Phe Phe
                20                  25                  30
Leu Ala Leu Thr Ser Thr Ala Leu Leu Phe Leu Leu Phe Phe Leu Thr
            35                  40                  45
Leu Arg Phe Ser Val Val
    50

<210> SEQ ID NO 35
<211> LENGTH: 42
<212> TYPE: PRT
<213> ORGANISM: Artificial Sequence
<220> FEATURE:
<223> OTHER INFORMATION: Synthetic Construct

<400> SEQUENCE: 35

Lys Arg Gly Arg Lys Lys Leu Leu Tyr Ile Phe Lys Gln Pro Phe Met
 1               5                  10                  15
Arg Pro Val Gln Thr Thr Gln Glu Glu Asp Gly Cys Ser Cys Arg Phe
                20                  25                  30
Pro Glu Glu Glu Glu Gly Gly Cys Glu Leu
            35                  40

<210> SEQ ID NO 36
<211> LENGTH: 147
<212> TYPE: PRT
<213> ORGANISM: Artificial Sequence
<220> FEATURE:
<223> OTHER INFORMATION: Synthetic Construct

<400> SEQUENCE: 36

Arg Val Lys Phe Ser Arg Ser Ala Asp Ala Pro Ala Tyr Gln Gln Gly
 1               5                  10                  15
Gln Asn Gln Leu Tyr Asn Glu Leu Asn Leu Gly Arg Arg Glu Glu Tyr
                20                  25                  30
Asp Val Leu Asp Lys Arg Arg Gly Arg Asp Pro Glu Met Gly Gly Lys
            35                  40                  45
```

```
Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
 65              70                  75                      80

Arg Arg Gly Lys Gly His Asp Gly Leu Tyr Gln Asp Ser His Phe Gln
                85                  90                  95

Ala Val Pro Val Gln Glu Lys Lys Arg Leu Arg Arg Ala Pro Trp
                100                 105                 110

Arg Ala Phe Ala Gln Pro Gln Arg Leu Lys His Arg Asn Asn Glu Leu
            115                 120                 125

Pro Asp Ser Leu Glu Pro Ile Tyr Lys Asn Ile Trp Asn Lys Thr Phe
        130                 135                 140

Ile Gly Glu
145

<210> SEQ ID NO 37
<211> LENGTH: 132
<212> TYPE: PRT
<213> ORGANISM: Artificial Sequence
<220> FEATURE:
<223> OTHER INFORMATION: Synthetic Construct

<400> SEQUENCE: 37

Val Leu His Leu Val Pro Ile Asn Ala Thr Ser Lys Asp Asp Ser Asp
 1               5                  10                  15

Val Thr Glu Val Met Trp Gln Pro Ala Leu Arg Arg Gly Arg Gly Leu
                20                  25                  30

Gln Ala Gln Gly Tyr Gly Val Arg Ile Gln Asp Ala Gly Val Tyr Leu
            35                  40                  45

Leu Tyr Ser Gln Val Leu Phe Gln Asp Val Thr Phe Thr Met Gly Gln
        50                  55                  60

Val Val Ser Arg Glu Gly Gln Gly Arg Gln Glu Thr Leu Phe Arg Cys
 65                 70                  75                  80

Ile Arg Ser Met Pro Ser His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val
    130

<210> SEQ ID NO 38
<211> LENGTH: 6
<212> TYPE: PRT
<213> ORGANISM: Artificial Sequence
<220> FEATURE:
<223> OTHER INFORMATION: Synthetic

<400> SEQUENCE: 38

Lys Gln Lys Lys Gln His
 1               5
```

T CELLS EXPRESSING A CHIMERIC ANTIGEN RECEPTOR

CROSS-REFERENCE TO RELATED APPLICATIONS

This application claims benefit under 35 U.S.C. § 119 (c) of U.S. Provisional Application Nos. 62/444,622, filed Jan. 10, 2017, 62/516,279, filed Jun. 7, 2017, and 62/580,258, filed Nov. 1, 2017, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created Nov. 30, 2023, is named M105370012US03-SUBSEQ-ARM and is 35,151 bytes in size.

TECHNICAL FIELD

The technology described herein relates to immunotherapy.

BACKGROUND

Chimeric antigen receptors (CARs) provide a way to direct a cytotoxic T cell response to target cells expressing a selected target antigen, most often a tumor antigen or tumor-associated antigen. CARs are an adaptation of the T cell receptor, where the antigen binding domain is replaced with the antigen binding domain of an antibody that specifically binds the derived target antigen. Engagement of the target antigen on the surface of a target cell by a CAR expressed on a T cell ("CAR T cell") promotes killing of the target cell.

SUMMARY

CAR T cells are a cutting edge therapeutic that shows great promise in treating cancer. The technique has proven particularly effective against various non-solid cancers, e.g., leukemias, lymphomas and myelomas. One of the greatest challenges with creating CAR T cells for a given disease or disorder is overcoming adverse reactions from off-target and systemic effects, such as cytokine release syndrome. While cytokine release syndrome is generally treatable, there is concern that the treatments for this complication may limit the efficacy and/or long term sustained effects of the CAR T cell treatment.

Another issue encountered in CAR T therapeutic designs is the escape of tumors through loss of the targeted antigen or tumor-associated factor recognized by the CAR. When a tumor down-regulates or otherwise loses cell surface expression of a targeted antigen or factor, it will no longer be efficiently attacked by CAR T cells designed to target that antigen or factor. This has been observed, for example in CAR T therapy targeting B cell maturation antigen (BCMA), which is expressed for example in B cell malignancies, leukemias, lymphomas and multiple myelomas.

Described herein are improvements in CAR design that avoid off-target effects and reduce the possibility for tumor escape by loss of target antigen. Accordingly, one aspect of the invention described herein relates to a chimeric antigen receptor (CAR) polypeptide comprising: one or more extracellular domains comprising a portion of Tumor Necrosis Factor (TNF) superfamily receptor ligand; a hinge and transmembrane domain; a co-stimulatory domain; and an intracellular signaling domain. In one embodiment, an approach is described herein, demonstrated using BCMA-related proteins as example tumor-associated targets, that uses a single ligand that binds two different tumor-related antigens or factors. In some embodiments, a single ligand is fused to transmembrane and T cell receptor intracellular effector domains, optionally with co-stimulatory domains, essentially as for CARs known in the art. Having a ligand that binds two different tumor-associated antigens or factors, instead of a single antigen means that a CAR will not lose effectiveness if one or the other of the antigens or factors is down-regulated by cells of the tumor. This is illustrated herein using as a ligand a portion of the APRIL (A PROliferation-Inducing Ligand) polypeptide, which binds with high affinity to both BCMA and TACI, another tumor-related antigen or factor. In some embodiments of any of the aspects described herein, the ligand oligomerizes (e.g., dimerizes or trimerizes), for example, by self-oligomerization. For example, in some embodiments, the ligand is a portion of a TNF superfamily receptor ligand. In some aspects, the CAR design includes more than one ligand (e.g., 2, 3, 4, 5, 6, 7, 8, 9, 10, or more ligands).

Accordingly, one aspect of the invention described herein relates to a CAR polypeptide comprising an extracellular domain comprising a portion of a TNF superfamily receptor ligand, which is N-terminal to the endogenous cleavage site, a hinge and transmembrane domain, a co-stimulatory domain, and an intracellular signaling domain. In one embodiment, the TNF superfamily receptor ligand is APRIL. In other embodiments, the TNF superfamily receptor ligand is TNF-alpha, lymphotoxin beta, OX40L, CD154, FasL, LIGHT, TL1A, CD70, Siva, CD153, 4-1BB ligand, TRAIL, RANKL, TWEAK, BAFF, CAMLG, LIGHT, NGF, BDNF, NT-3, NT-4, GITR ligand, TL1A, or EDA-A2.

Accordingly, one aspect of the invention described herein relates to a CAR polypeptide comprising an extracellular domain comprising a portion of APRIL, which is N-terminal to the endogenous cleavage site, a hinge and transmembrane domain, a co-stimulatory domain, and an intracellular signaling domain.

In one embodiment of any aspect, the CAR polypeptide further comprises a CD8 leader sequence. In one embodiment, the CD8 leader sequence comprises the sequence selected from SEQ ID NO: 20, 26, or 32, or is encoded by a nucleic acid comprising the sequence selected from SEQ ID NO: 2, 9, or 14.

In one embodiment, the portion of APRIL comprises the sequence selected from SEQ ID NO: 21, 27, or 33, or is encoded by a nucleic acid comprising the sequence selected from SEQ ID NO: 3, 9, or 15. In one embodiment of any aspect, the portion of APRIL does not comprise a lysine-rich region of APRIL.

In one embodiment of any aspect, the hinge and transmembrane domain comprises the hinge and transmembrane domain of CD8 or 4-1BB. In one embodiment, the CD8 hinge and transmembrane domain sequence comprises the sequence of SEQ ID NO: 22, or is encoded by a nucleic acid comprising the sequence of SEQ ID NO: 4. In one embodiment, the 4-1BB hinge and transmembrane domain sequence is selected from SEQ ID NO: 28 or 34, or is encoded by a nucleic acid comprising the sequence of SEQ ID NO: 10 or 16.

In one embodiment of any aspect, the intracellular signaling domain comprises the signaling domain of CD3zeta, CD3 eta, or CD3 theta. In one embodiment, the CD3zeta intracellular signaling domain sequence is selected from SEQ ID NO: 24 or 30, or is encoded by a nucleic acid comprising the sequence of SEQ ID NO: 6 or 12. In one embodiment, the CD3 theta intracellular signaling domain sequence comprises the sequence of SEQ ID NO: 36, or is encoded by a nucleic acid comprising the sequence of SEQ ID NO: 18.

In one embodiment of any aspect, the co-stimulatory domain is 4-1BB intracellular domain (ICD), CD28 ICD, CD27 ICD, ICOS ICD, or OX40 ICD. In one embodiment, the co-stimulatory domain is 4-1BB ICD. In one embodiment, the 4-1BB ICD sequence comprises a sequence selected from SEQ ID NO: 23, 29, or 35, or is encoded by a nucleic acid comprising the sequence of SEQ ID NO: 5, 11, or 17.

In one embodiment of any aspect, the CAR polypeptide comprises two or more (e.g., two or more, three or more, four or more, five or more, six or more, seven or more, eight or more, nine or more, or ten or more) extracellular domains comprising a portion of a TNF superfamily receptor ligand. In one embodiment, the CAR polypeptide comprises three extracellular domains comprising a portion of TNF superfamily receptor ligand.

Another aspect of the invention described herein relates to a CAR polypeptide comprising at least 95% identity with a sequence selected from SEQ ID NO: 19, 25, or 31, or that is encoded by a sequence comprising at least 95% identity with a sequence selected from SEQ ID NO: 1, 7, or 13.

Another aspect of the invention described herein relates to a CAR polypeptide comprising a sequence selected from SEQ ID NO: 19, 25, or 31, or that is encoded by a sequence selected from SEQ ID NO: 1, 7, or 13.

Another aspect of the invention described herein relates to a CAR polypeptide comprising a sequence corresponding to a sequence selected from SEQ ID NO: 19, 25, or 31, or that is encoded by a sequence selected from SEQ ID NO: 1, 7, or 13.

Another aspect of the invention described herein relates to a polypeptide complex comprising two or more (e.g., two or more, three or more, four or more, five or more, six or more, seven or more, eight or more, nine or more, or ten or more) of any of the CAR polypeptides described herein. In one embodiment, the polypeptide complex comprises three of any of the CAR polypeptides described herein.

Another aspect of the invention described herein relates to a mammalian cell comprising: any of the CAR polypeptides described herein; a nucleic acid encoding any of the CAR polypeptides described herein; or any of the polypeptide complexes described herein.

In one embodiment of any aspect, the cell is a T cell. In one embodiment, the cell is a human cell. In one embodiment, the cell is obtained from an individual having or diagnosed as having cancer, a plasma cell disorder, or autoimmune disease.

Another aspect of the invention described herein relates to a method of treating cancer, a plasma cell disorder, amyloidosis, or an autoimmune disease in a subject, the method comprising: engineering a T cell to comprise any of the CAR polypeptides described herein on the T cell surface; administering the engineered T cell to the subject.

Another aspect of the invention described herein relates to a method of treating cancer, a plasma cell disorder, or an autoimmune disease in a subject, the method comprising administering a cell comprising any of the CAR polypeptides described herein, or a nucleic acid encoding any of the CAR polypeptides described herein.

In one embodiment of any aspect, the cancer is BAFF+, BCMA+ and/or TACI$^+$. In one embodiment, wherein the cancer is multiple myeloma or smoldering myeloma.

In one embodiment of any aspect, the subject is further administered an anti-BCMA therapy. In one embodiment, the subject is resistant to anti-BCMA therapies.

In one embodiment of any aspect, the autoimmune disease is selected from the group consisting of hemophilia with antibodies to coagulation factors, myasthenia gravis, multiple sclerosis, and chronic graft v. host disease.

Another aspect of the technology described herein relates to a composition comprising a CAR polypeptide as described herein formulated for the treatment of cancer. In one embodiment, the composition further comprises a pharmaceutically acceptable carrier.

Another aspect of the technology described herein relates to a composition comprises a protein complex as described herein formulated for the treatment of cancer. In one embodiment, the composition further comprises a pharmaceutically acceptable carrier.

Another aspect of the technology described herein relates to a composition comprises a CAR T cell as described herein formulated for the treatment of cancer. In one embodiment, the composition further comprises a pharmaceutically acceptable carrier.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (cd.), John Wiley and Sons, Inc., 2005; and Current Protocols in Immunology (CPI) (John E. Coligan, ADA M Kruisbeck, David H Margulies, Ethan M Shevach, Warren Strobe, (cds.) John Wiley and Sons, Inc., 2003 (ISBN 0471142735, 9780471142737), the contents of which are all incorporated by reference herein in their entireties.

The term "TNF superfamily receptor ligand" refers to a ligand that binds to a TNF superfamily receptor. TNF superfamily receptor ligands can be active as non-covalent oligomers (e.g., trimers). In some embodiments, a TNF superfamily receptor ligand is active as a homooligomer (e.g., a homotrimer). However, some TNF superfamily receptor ligands can be active as a heterooligomer (e.g., a heterotrimer), including BAFF, which can form a heterooligomer with APRIL. In some embodiments, the TNF superfamily receptor ligand is one that is described in Aggarwal, *Nat. Rev. Immunol.* 3:745-756, 2003 or Croft et al. *Nat. Rev. Immunol.* 9 (4): 271-285, 2009. In some embodiments, the TNF superfamily receptor ligand is TNF-alpha, lymphotoxin beta, OX40L, CD154, FasL, LIGHT, TLIA, CD70, Siva, CD153, 4-1BB ligand, TRAIL, RANKL, TWEAK, BAFF, CAMLG, LIGHT, NGF, BDNF, NT-3, NT-4, GITR ligand, TLIA, or EDA-A2. In some embodiments, the TNF superfamily receptor ligand binds to a TNF superfamily receptor described in Aggarwal, supra, or Croft et al, supra, including, e.g., TNFR1, TNFR2, CD95, DCR3, DR3, DR4, DR5, DCR1, DCR2, DR6, EDAR, NGFR, OPG, RANK, LTbetaR, FN14, HVEM, CD27, CD30, CD40, 4-1BB, OX40, GITR, BCMA, TACI, BAFFR, XEDAR, TROY, or RELT.

The term "portion" refers to a part of a polypeptide, e.g., a TNF superfamily receptor ligand (e.g., APRIL). In some embodiments, a portion of a TNF superfamily receptor ligand is N-terminal to the endogenous cleavage site, and comprises at least the TNF-like domain. In some embodiments, a portion of a TNF superfamily receptor ligand is capable of oligomerization (e.g., dimerization or trimerization). The oligomerization may be homooligomerizaion or heterooligomerization.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. Where applicable, a decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include, for example, chimpanzees, cynomologous monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of disease e.g., cancer. A subject can be male or female.

A subject can be one who has been previously diagnosed with or identified as suffering from or having a condition in need of treatment (e.g. leukemia or another type of cancer, among others) or one or more complications related to such a condition, and optionally, have already undergone treatment for the condition or the one or more complications related to the condition. Alternatively, a subject can also be one who has not been previously diagnosed as having such condition or related complications. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

A "disease" is a state of health of an animal, for example a human, wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "tumor antigen" and "cancer antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), and fusion proteins resulting from internal deletions or chromosomal translocations. Still other cancer antigens can be encoded by viral genes such as those carried on RNA and DNA tumor viruses. Many tumor antigens have been defined in terms of multiple solid tumors: MAGE 1, 2, & 3, defined by immunity; MART-1/Melan-A, gp100, carcinoembryonic antigen (CEA), HER2, mucins (i.e., MUC-1), prostate-specific antigen (PSA), and prostatic acid phosphatase (PAP). In addition, viral proteins such as some encoded by hepatitis B (HBV), Epstein-Barr (EBV), and human papilloma (HPV) have been shown to be important in the development of hepatocellular carcinoma, lymphoma, and cervical cancer, respectively.

As used herein, the term "chimeric" refers to the product of the fusion of portions of at least two or more different polynucleotide molecules. In one embodiment, the term "chimeric" refers to a gene expression element produced through the manipulation of known elements or other polynucleotide molecules.

In some embodiments, "activation" can refer to the state of a T cell that has been sufficiently stimulated to induce detectable cellular proliferation. In some embodiments activation can refer to induced cytokine production. In other embodiments, activation can refer to detectable effector functions. At a minimum, an "activated T cell" as used herein is a proliferative T cell.

As used herein, the terms "specific binding" and "specifically binds" refer to a physical interaction between two molecules, compounds, cells and/or particles wherein the first entity binds to the second, target, entity with greater specificity and affinity than it binds to a third entity which is a non-target. In some embodiments, specific binding can refer to an affinity of the first entity for the second target, entity, which is at least 10 times, at least 50 times, at least 100 times, at least 500 times, at least 1000 times or more greater than the affinity for the third nontarget entity under the same conditions. A reagent specific for a given target is one that exhibits specific binding for that target under the conditions of the assay being utilized. A non-limiting example includes an antibody, or a ligand, which recognizes and binds with a cognate binding partner (for example, a stimulatory and/or costimulatory molecule present on a T cell) protein.

A "stimulatory ligand," as used herein, refers to a ligand that when present on an antigen presenting cell (APC e.g., a macrophage, a dendritic cell, a B-cell, an artificial APC, and the like) can specifically bind with a cognate binding partner (referred to herein as a "stimulatory molecule" or "co-stimulatory molecule") on a T cell, thereby mediating a primary response by the T cell, including, but not limited to, proliferation, activation, initiation of an immune response, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

A "stimulatory molecule," as the term is used herein, means a molecule on a T cell that specifically binds with a cognate stimulatory ligand present on an antigen presenting cell.

"Co-stimulatory ligand," as the term is used herein, includes a molecule on an APC that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, 4-1BBL, OX40L, CD7, B7-1 (CD80), B7-2 (CD86), PD-L1, PD-L2, inducible COStimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll-like receptor and a ligand that specifically binds with B7-H3. A co-stimulatory ligand also can include, but is not limited to, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA, a Toll-like receptor, CD27, CD28, 4-1BB, OX40, CD30, CD40, PD-1, ICOS, lymphocyte function-associated antigen-1 (LFA-1), CD2, CD7, LIGHT, NKG2C, B7-H3, and CD83.

In one embodiment, the term "engineered" and its grammatical equivalents as used herein can refer to one or more human-designed alterations of a nucleic acid, e.g., the nucleic acid within an organism's genome. In another embodiment, engineered can refer to alterations, additions, and/or deletion of genes. An "engineered cell" can refer to a cell with an added, deleted and/or altered gene. The term "cell" or "engineered cell" and their grammatical equivalents as used herein can refer to a cell of human or non-human animal origin.

As used herein, the term "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. The two polynucleotide molecules may or may not be part of a single contiguous polynucleotide molecule and may or may not be adjacent. For example, a promoter is operably linked to a gene of interest if the promoter regulates or mediates transcription of the gene of interest in a cell.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of ordinary skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. ligand-mediated receptor activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser(S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, a polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to an assay known in the art or described below herein. A functional fragment can comprise conservative substitutions of the sequences disclosed herein.

In some embodiments, a polypeptide described herein can be a variant of a polypeptide or molecule as described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity of the non-variant polypeptide. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp® or BLASTn® with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of a polypeptide also can be substituted, generally with serine, to improve the oxidative stability of the molecule and prevent aberrant crosslinking. Conversely, cysteine bond(s) can be added to a polypeptide to improve its stability or facilitate oligomerization.

As used herein, the term "DNA" is defined as deoxyribonucleic acid. The term "polynucleotide" is used herein interchangeably with "nucleic acid" to indicate a polymer of nucleosides. Typically a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e. the succession of letters used as abbreviations for bases) that biochemically characterizes a specific nucleic acid. A polynucleotide sequence presented herein is presented in a 5' to 3' direction unless otherwise indicated.

The term "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a nonpolypeptide moiety covalently or noncovalently associated therewith is still considered a "polypeptide." Exemplary modifications include glycosylation and palmitoylation. Polypeptides can be purified from natural sources, produced using recombinant DNA technology or synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

In some embodiments, a nucleic acid encoding a polypeptide as described herein (e.g. a CAR polypeptide) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain a nucleic acid encoding a polypeptide as described herein in place of non-essential viral genes. The vector and/or particle may be utilized for the purpose of transferring nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra-chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. acute lymphoblastic leukemia or other cancer, disease, or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier in which the active ingredient would not be found to occur in nature.

As used herein, the term "administering," refers to the placement of a therapeutic or pharmaceutical composition as disclosed herein into a subject by a method or route which results in at least partial delivery of the agent at a desired site. Pharmaceutical compositions comprising agents as disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the technology.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined within the description of the various aspects and embodiments of the technology of the following.

DETAILED DESCRIPTION

Figure 1:
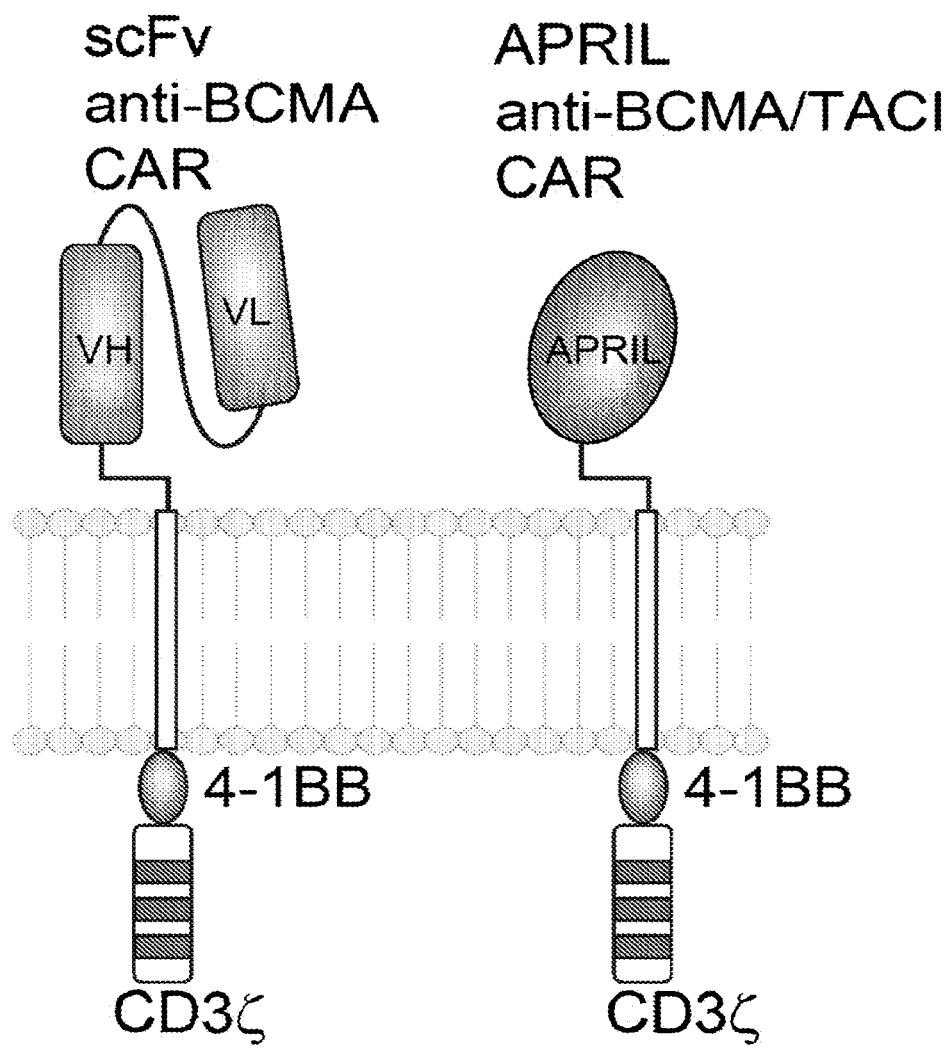
FIG. 1 depicts a schematic comparison of scFv-based anti-BCMA CAR vs. APRIL anti-BCMA/TACI CAR.

Described herein are improvements in CAR design that avoid off-target effects and reduce the possibility for tumor escape by loss of target antigen. In one embodiment, an approach is described herein that uses a single ligand that binds two different tumor-related antigens or factors. The single ligand is fused to transmembrane and T cell receptor intracellular effector domains, optionally with co-stimulatory domains, essentially as for CARs known in the art. A CAR with a ligand that binds two different tumor-associated antigens or factors will not lose effectiveness if one or the other of the antigens or factors is down-regulated by targeted cells. In some embodiments, the CAR includes a ligand that includes a portion of a TNF superfamily receptor ligand. This is illustrated herein using as a ligand a portion of the APRIL polypeptide, which binds with high affinity to both the multiple myeloma and leukemia-associated BCMA polypeptide and TACI, another factor expressed on multiple myelomas.

Embodiments of the technology described herein relate to the discovery that a T cell comprising a CAR polypeptide comprising an extracellular portion of a TNF superfamily receptor ligand (e.g., APRIL) is an efficient therapeutic to treat cancer, a plasma cell disorder, or an autoimmune disease, without invoking off-target effects or adverse reactions.

Accordingly, one aspect of the invention described herein relates to a CAR polypeptide comprising a) an extracellular domain comprising a portion of a TNF superfamily receptor ligand (e.g., APRIL), which is N-terminal to the endogenous cleavage site, and comprises at least the TNF-like domain, b) a hinge and transmembrane domain, and c) an intracellular signaling domain. In some embodiments, the TNF superfamily receptor ligand is APRIL. In other embodiments, the TNF superfamily receptor ligand is TNF-alpha, lymphotoxin beta, OX40L, CD154, FasL, LIGHT, TLIA, CD70, Siva, CD153, 4-1BB ligand, TRAIL, RANKL, TWEAK, BAFF, CAMLG, LIGHT, NGF, BDNF, NT-3, NT-4, GITR ligand, TLIA, or EDA-A2.

Considerations necessary to make and use these and other aspects of the technology are described in the following.

Chimeric Antigen Receptors

The technology described herein provides improved CARs for use in immunotherapy. The following discusses CARs and the various improvements.

The terms "chimeric antigen receptor" or "CAR" or "CARs" as used herein refer to engineered T cell receptors, which graft a ligand or antigen specificity onto T cells (for example naïve T cells, central memory T cells, effector memory T cells or combinations thereof). CARs are also known as artificial T-cell receptors, chimeric T-cell receptors or chimeric immunoreceptors.

A CAR places a chimeric extracellular target-binding domain that specifically binds a target, e.g., a polypeptide expressed on the surface of a cell to be targeted for a T cell response onto a construct including a transmembrane domain, and intracellular domain(s) (including signaling domains) of a T cell receptor molecule. In one embodiment, the chimeric extracellular target-binding domain comprises the antigen-binding domain(s) of an antibody that specifically binds an antigen expressed on a cell to be targeted for a T cell response. The properties of the intracellular signaling domain(s) of the CAR can vary as known in the art and as disclosed herein, but the chimeric target/antigen-binding domains(s) render the receptor sensitive to signaling activation when the chimeric target/antigen binding domain binds the target/antigen on the surface of a targeted cell.

With respect to intracellular signaling domains, so-called "first-generation" CARs include those that solely provide CD3zeta (CD3) signals upon antigen binding. So-called "second-generation" CARs include those that provide both co-stimulation (e.g., CD28 or CD 137) and activation (CD35) domains, and so-called "third-generation" CARs include those that provide multiple costimulatory (e.g., CD28 and CD 137) domains and activation domains (e.g., CD32). In various embodiments, the CAR is selected to have high affinity or avidity for the target/antigen—for example, antibody-derived target or antigen binding domains will generally have higher affinity and/or avidity for the target antigen than would a naturally-occurring T cell receptor. This property, combined with the high specificity one can select for an antibody provides highly specific T cell targeting by CAR T cells.

As used herein, a "CAR T cell" or "CAR-T" refers to a T cell which expresses a CAR. When expressed in a T cell, CARs have the ability to redirect T-cell specificity and reactivity toward a selected target in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape.

As used herein, the term "extracellular target binding domain" refers to a polypeptide found on the outside of the cell sufficient to facilitate binding to a target. The extracellular target binding domain will specifically bind to its binding partner. As non-limiting examples, the extracellular target-binding domain can include an antigen-binding domain of an antibody, or a ligand (for example, APRIL), which recognizes and binds with a cognate binding partner protein. In this context, a ligand is a molecule which binds specifically to a portion of a protein and/or receptor. The cognate binding partner of a ligand useful in the methods and compositions described herein can generally be found on the surface of a cell. Ligand: cognate partner binding can result in the alteration of the ligand-bearing receptor, or activate a physiological response, for example, the activation of a signaling pathway or cascade. In one embodiment, the ligand can be non-native to the genome. Optionally, the ligand has a conserved function across at least two species.

Antibody Reagents

In various embodiments, the CARs described herein comprise an antibody reagent or an antigen-binding domain thereof as an extracellular target-binding domain.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F (ab') 2, Fd fragments, Fv fragments, scFv, CDRs, and domain antibody (dAb) fragments (see, e.g. de Wildt et al., Eur J. Immunol. 1996; 26 (3): 629-39; which is incorporated by reference herein in its entirety)) as well as complete antibodies. An antibody can have the structural features of IgA, IgG, IgE, IgD, or IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like. Fully human antibody binding domains can be selected, for example, from phage display libraries using methods known to those of ordinary skill in the art.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

In one embodiment, the antibody or antibody reagent is not a human antibody or antibody reagent, (i.e., the antibody or antibody reagent is mouse), but has been humanized. A "humanized antibody or antibody reagent" refers to a non-human antibody or antibody reagent that has been modified at the protein sequence level to increase its similarity to antibody or antibody reagent variants produced naturally in humans. One approach to humanizing antibodies employs the grafting of murine or other non-human CDRs onto human antibody frameworks.

In one embodiment, a CAR's extracellular target binding domain comprises or consists essentially of a single-chain Fv (scFv) fragment created by fusing the VH and VL domains of an antibody, generally a monoclonal antibody, via a flexible linker peptide. In various embodiments, the scFv is fused to a transmembrane domain and to a T cell receptor intracellular signaling domain, e.g., an engineered intracellular signaling domain as described herein.

Antibody binding domains and ways to select and clone them are well known to those of ordinary skill in the art.

In one embodiment, the extracellular domain of the CAR polypeptide comprises a portion of a TNF superfamily receptor ligand, wherein the portion of the TNF superfamily receptor ligand is N-terminal to the endogenous cleavage site, and comprises at least the TNF-like domain.

For example, in one embodiment, the extracellular domain of the CAR polypeptide comprises a portion of APRIL, wherein the portion of APRIL is N-terminal to the endogenous cleavage site, and comprises at least the TNF-like domain (SEQ ID NO: 37).

(SEQ ID NO: 37)
VLHLVPINATSKDDSDVTEVMWQPALRRGRGLQAQGYGVRIQDAGVYLLY

SQVLFQDVTFTMGQVVSREGQGRQETLFRCIRSMPSHPDRAYNSCYSAGV

FHLHQGDILSVIIPRARAKLNLSPHGTFLGFV

APRIL is a member of the tumor necrosis factor ligand (TNF) family, and functions as a ligand for BCMA. APRIL sequences are known for a number of species, e.g., human APRIL, also known as TNFSF13 (NCBI Gene ID: 8741) polypeptide (e.g., NCBI Ref Seq NP_001185551.1) and mRNA (e.g., NCBI Ref Seq NM_001198622.1). APRIL can refer to human APRIL, including naturally occurring variants, molecules, and alleles thereof. In some embodiments of any of the aspects, e.g., in veterinary applications, APRIL can refer to the APRIL of, e.g., dog, cat, cow, horse, pig, and the like. Homologs and/or orthologs of human APRIL are readily identified for such species by one of skill in the art, e.g., using the NCBI ortholog search function or searching available sequence data for a given species for sequence similar to a reference APRIL sequence.

In one embodiment, the portion of APRIL has a sequence corresponding to a sequence selected from SEQ ID NO: 3, 8, 15, 21, 27, or 33; or comprises a sequence selected from SEQ ID NO: 3, 8, 15, 21, 27, or 33; or comprises a sequence with at least 80%, at least 85%, at least 90%, at least 91%, at least 92%, at least 93%, at least 94%, at least 95%, at least 96%, at least 97%, at least 98%, at least 99%, or at least 100% sequence identity to a sequence selected from SEQ ID NO 3, 8, 15, 21, 27, or 33. In one embodiment, the portion of APRIL consists essentially of a sequence selected from SEQ ID NO: 3, 8, 15, 21, 27, or 33; or consists essentially of a sequence with at least 80%, at least 85%, at least 90%, at least 91%, at least 92%, at least 93%, at least 94%, at least 95%, at least 96%, at least 97%, at least 98%, at least 99%, or at least 100% sequence identity to a sequence selected from SEQ ID NO 3, 8, 15, 21, 27, or 33. In one embodiment, the portion of APRIL does not comprise a sequence derived from the portion of APRIL which is C-terminal of the endogenous cleavage site.

In one embodiment, the CAR polypeptide comprises a portion of a TNF superfamily receptor ligand that comprises one or more mutations within its coding region. For example, in one embodiment, the CAR polypeptide comprises a portion of APRIL that comprises one or more mutations within its coding region. Exemplary amino acid mutations include point mutation made to amino acids 18, 61, 91, 92, and 117 of SEQ ID NO: 21; amino acids 18, 63, 91, 92, 117 of SEQ ID NO: 27; and amino acids 18, 63, 91, 92, 117 of SEQ ID NO: 33. One skilled in the art will be capable of introducing mutations into the nucleic acid sequence of a gene or gene product using standard techniques. For example, point mutations can be introduced via site-directed point mutagenesis, a PCR technique. Site-directed mutagenesis kits are commercially available, for instance, through New England Biolabs®; Ipswich, MA. Non-limiting examples of alternative methods to introduce point mutations to the nucleic acid sequence of a gene or gene product include cassette mutagenesis or whole plasmid mutagenesis.

Optionally, the portion of a TNF superfamily receptor ligand (e.g., APRIL) does not comprise a lysine-rich region. In one embodiment, a "lysine-rich region" refers to a region of the amino acid sequence that comprises at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% lysine amino acids. As used herein a "region" refers to at least 4 or more consecutive amino acids. In one embodiment, the lysine rich sequence comprises a sequence of KOKKQH (SEQ ID NO: 38).

In one embodiment, the CARs useful in the technology described herein comprise at least two antigen-specific targeting regions in an extracellular domain, a transmembrane domain, and an intracellular signaling domain. In such embodiments, the two or more antigen-specific targeting regions target at least two different antigens and may be arranged in tandem and separated by linker sequences. In another embodiment, the CAR is a bispecific CAR. A bispecific CAR is specific to two different antigens.

Figure 16:
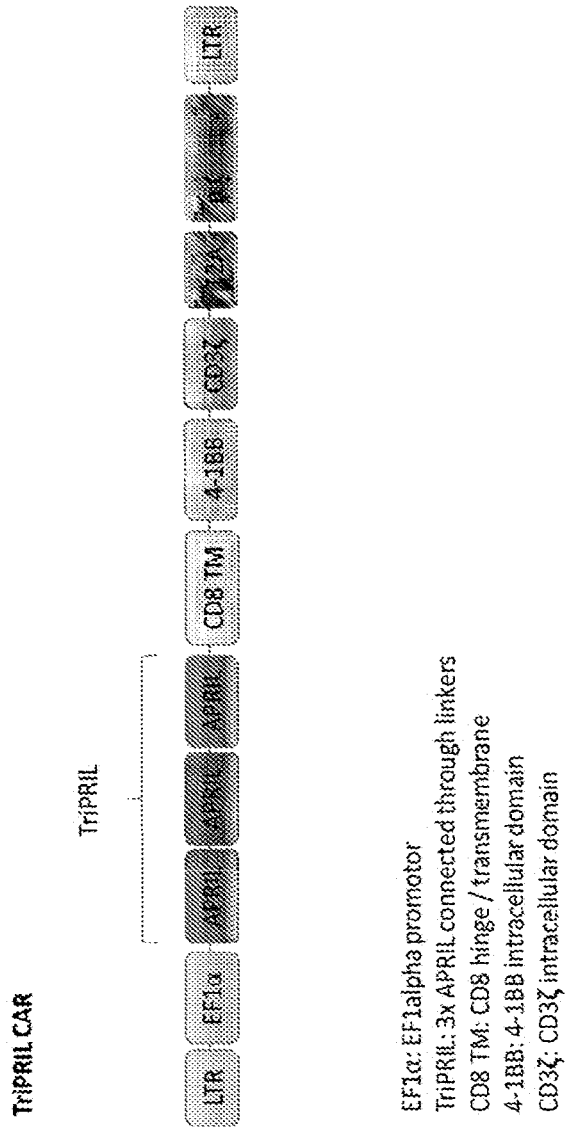
FIG. 16 depicts a schematic diagram of the exemplary TriPRIL construct.

In one embodiment of any aspect, the CAR polypeptide comprises two or more (e.g., two or more, three or more, four or more, five or more, six or more, seven or more, eight or more, nine or more, or ten or more) extracellular domains comprising a portion of a TNF superfamily receptor ligand (e.g., APRIL). In one embodiment, the CAR polypeptide comprises three extracellular domains comprising a portion of TNF superfamily receptor ligand (e.g., APRIL). For example, in some embodiments, the CAR polypeptide may include a repeat of two or more (e.g., two or more, three or more, four or more, five or more, six or more, seven or more, eight or more, nine or more, or ten or more) TNF superfamily receptor ligands (e.g., APRIL, as is shown in FIG. 16 where APRIL is provided as a triple repeat). In some embodiments, the TNF superfamily receptor ligands are the same. In other embodiments, the TNF superfamily receptor ligands may be different (e.g., the CAR may include one or more portions of APRIL and one or more portions of a second TNF superfamily receptor ligand (e.g., BAFF).

In one embodiment of any aspect, the TNF superfamily receptor ligand (e.g., APRIL) oligomerizes (e.g., dimerizes or trimerizes) with another TNF superfamily receptor ligand (e.g., APRIL). The oligomerization may be intramolecular or intermolecular. The oligomer may be a homooligomer or a heterooligomer.

Target/Antigen

Any cell-surface moiety can be targeted by a CAR. Most often, the target will be a cell-surface polypeptide differentially or preferentially expressed on a cell one wishes to target for a T cell response. In this regard, tumor antigens or tumor-associated antigens provide attractive targets, providing a means to target tumor cells while avoiding or at least limiting collateral damage to non-tumor cells or tissues. Non-limiting examples of tumor antigens or tumor-associated antigens include CEA, Immature laminin receptor, TAG-72, HPV E6 and E7, BING-4, Calcium-activated chloride channel 2, Cyclin B1, 9D7, Ep-CAM, EphA3, Her2/neu, Telomerase, Mesotheliun, SAP-1, Survivin, BAGE family, CAGE family, GAGE family, MAGE family, SAGE family, XAGE family, NY-ESO-1/LAGE-1, PRAME, SSX-2, Melan-A/MART-1, Gp100/pmel17, Tyrosinase, TRP-1/-2, MCIR, BRCA1/2, CDK4, MART-2, p53, Ras, MUCI, and TGF-βRII.

In one aspect, the cell-surface moiety may be a TNF superfamily receptor, e.g., TNFR1, TNFR2, CD95, DCR3, DR3, DR4, DR5, DCR1, DCR2, DR6, EDAR, NGFR, OPG, RANK, LTbetaR, FN14, HVEM, CD27, CD30, CD40, 4-1BB, OX40, GITR, BCMA, TACI, BAFFR, XEDAR, TROY, or RELT. In some embodiments, the TNF superfamily receptor is BCMA or TACI.

Hinge and TM Domain

Each CAR as described herein necessarily includes a transmembrane domain that joins the extracellular target-binding domain to the intracellular signaling domain.

As used herein, "hinge domain" refers to an amino acid region that allows for separation and flexibility of the binding moiety and the T cell membrane. The length of the flexible hinges also allow for better binding to relatively inaccessible epitopes, e.g., longer hinge regions are allow for optimal binding. One skilled in the art will be able to determine the appropriate hinge for the given CAR target. In one embodiment, the transmembrane domain or fragment thereof of any of the CAR polypeptides described herein comprises a CD8 or 4-1BB hinge domain.

Each CAR as described herein necessarily includes a transmembrane domain that joins the extracellular target-binding domain to the intracellular signaling domain.

As used herein, "transmembrane domain" (TM domain) refers to the generally hydrophobic region of the CAR which crosses the plasma membrane of a cell. The TM domain can be the transmembrane region or fragment thereof of a transmembrane protein (for example a Type I transmembrane protein or other transmembrane protein), an artificial hydrophobic sequence, or a combination thereof. While specific examples are provided herein and used in the Examples, other transmembrane domains will be apparent to those of skill in the art and can be used in connection with alternate embodiments of the technology. A selected transmembrane region or fragment thereof would preferably not interfere with the intended function of the CAR. As used in relation to a transmembrane domain of a protein or polypeptide, "fragment thereof" refers to a portion of a transmembrane domain that is sufficient to anchor or attach a protein to a cell surface.

In one embodiment, the transmembrane domain or fragment thereof of any of the CAR polypeptides described herein comprises a transmembrane domain selected from the transmembrane domain of CD8 or 4-1BB. In an alternate embodiment of any aspect, the transmembrane domain or fragment thereof of the CAR described herein comprises a transmembrane domain selected from the transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R a, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

4-1BBL is a type 2 transmembrane glycoprotein belonging to the TNFR/TNF ligand superfamily. 4-1BBL is a co-stimulatory ligand that binds receptor 4-1BB (CD137) expressed on T cell. 4-1BBL is expressed on professional APCs including dendritic cells, macrophages, and activated B cells. 4-1BBL sequences are known for a number of species, e.g., human 4-1BBL, also known as TNFSF9 (NCBI Gene ID: 8744) polypeptide (e.g., NCBI Ref Seq NP_003802.1) and mRNA (e.g., NCBI Ref Seq NM_003811.3). 4-1BBL can refer to human 4-1BBL, including naturally occurring variants, molecules, and alleles thereof. In some embodiments of any of the aspects, e.g., in veterinary applications, 4-1BBL can refer to the 4-1BBL of, e.g., dog, cat, cow, horse, pig, and the like. Homologs and/or orthologs of human 4-1BBL are readily identified for such species by one of skill in the art, e.g., using the NCBI ortholog search function or searching available sequence data for a given species for sequence similar to a reference 4-1BBL sequence.

In one embodiment, the 4-1BBL hinge and transmembrane sequence corresponds to a nucleotide sequence selected from SEQ ID NO: 10 or 16; or comprises a sequence selected from SEQ ID NO: 10 or 16; or comprises a sequence with at least 80%, at least 85%, at least 90%, at least 91%, at least 92%, at least 93%, at least 94%, at least 95%, at least 96%, at least 97%, at least 98%, at least 99%, or at least 100% sequence identity to a sequence selected from SEQ ID NO: 10 or 16. In one embodiment, the 4-1BBL hinge and transmembrane sequence corresponds to an amino acid sequence selected from SEQ ID NO: 28 or 34; or comprises a sequence selected from SEQ ID NO: 28 or 34; or comprises a sequence with at least 80%, at least 85%, at least 90%, at least 91%, at least 92%, at least 93%, at least 94%, at least 95%, at least 96%, at least 97%, at least 98%, at least 99%, or at least 100% sequence identity to a sequence selected from SEQ ID NO: 28 or 34.

CD8 is an antigen preferentially found on the cell surface of cytotoxic T lymphocytes. CD8 mediates cell-cell interactions within the immune system, and acts as a T cell coreceptor. CD8 consists of an alpha (CD8a) and beta (CD8b) chain. CD8a sequences are known for a number of species, e.g., human CD8a, (NCBI Gene ID: 925) polypeptide (NCBI Ref Seq NP_001139345.1) and mRNA (e.g., NCBI Ref Seq NM_000002.12). CD8 can refer to human CD8, including naturally occurring variants, molecules, and alleles thereof. In some embodiments of any of the aspects, e.g., in veterinary applications, CD8 can refer to the CD8 of, e.g., dog, cat, cow, horse, pig, and the like. Homologs and/or orthologs of human CD8 are readily identified for such species by one of skill in the art, e.g., using the NCBI ortholog search function or searching available sequence data for a given species for sequence similar to a reference CD8 sequence.

In one embodiment, the CD8 hinge and transmembrane sequence corresponds to the nucleotide sequence of SEQ ID NO: 4; or comprises the sequence of SEQ ID NO: 4; or comprises a sequence with at least 80%, at least 85%, at least 90%, at least 91%, at least 92%, at least 93%, at least 94%, at least 95%, at least 96%, at least 97%, at least 98%, at least 99%, or at least 100% sequence identity to the sequence of SEQ ID NO: 4. In one embodiment, the CD8 hinge and transmembrane sequence corresponds to the amino acid sequence of SEQ ID NO: 22; or comprises the sequence of SEQ ID NO: 22; or comprises a sequence with at least 80%, at least 85%, at least 90%, at least 91%, at least 92%, at least 93%, at least 94%, at least 95%, at least 96%, at least 97%, at least 98%, at least 99%, or at least 100% sequence identity to the sequence of SEQ ID NO: 22.

Co-Stimulatory Domain

Each CAR described herein comprises an intracellular domain of a co-stimulatory molecule, or co-stimulatory domain. As used herein, the term "co-stimulatory domain" refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules include CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70. In one embodiment, the intracellular domain is the intracellular domain of 4-1BB.

In one embodiment, the CAR polypeptide further comprises an intracellular domain. As used herein, an "intracellular domain" refers to a nucleic acid fully comprised within a cell. In one embodiment, the intracellular domain refers to the intracellular domain of a receptor. An intracellular domain can interact with the interior of a cell. With respect to the intracellular domain of a receptor, the intracellular domain can function to relay a signal transduced. An intracellular domain of a receptor can comprise enzymatic activity.

In one embodiment, the intracellular domain is the intracellular domain of a 4-1BB. In one embodiment, the 4-1BB intracellular domain sequence corresponds to a nucleotide sequence selected from SEQ ID NO: 511, or 17; or comprises a sequence selected from SEQ ID NO: 5, 11, or 17; or comprises at least 80%, at least 85%, at least 90%, at least 95%, at least 96%, at least 97%, at least 98%, at least 99%, or at least 100% sequence identity to a sequence selected from SEQ ID NO: 5, 11, or 17. In one embodiment, the 4-1BB intracellular domain amino acid sequence corresponds to an amino acid sequence selected from SEQ ID NO: 23, 29, or 35; or comprises a sequence selected from SEQ ID NO: 23, 29, or 35; or comprises at least 80%, at least 85%, at least 90%, at least 95%, at least 96%, at least 97%, at least 98%, at least 99%, or at least 100% sequence identity to a sequence selected from SEQ ID NO: 23, 29, or 35.

Intracellular Signaling Domain

CARs as described herein comprise an intracellular signaling domain. An "intracellular signaling domain," refers to the part of a CAR polypeptide that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited following antigen binding to the extracellular CAR domain.

CD3 is a T cell co-receptor that facilitates T lymphocytes activation when simultaneously engaged with the appropriate co-stimulation (e.g., binding of a co-stimulatory molecule). A CD3 complex consists of 4 distinct chains; mammal CD3 consists of a CD3γ chain, a CD3δ chain, and two CD3δ chains. These chains associate with a molecule known as the T cell receptor (TCR) and the CD3ξ to generate an activation signal in T lymphocytes. A complete TCR complex comprises a TCR, CD3ξ, and the complete CD3 complex.

In some embodiments of any aspect, a CAR polypeptide described herein comprises an intracellular signaling domain that comprises an Immunoreceptor Tyrosine-based Activation Motif or ITAM from CD3 zeta (CD3ξ). In some embodiments of any aspect, the ITAM comprises three motifs of ITAM of CD3ξ (ITAM3). In some embodiments of any aspect, the three motifs of ITAM of CD3& are mutated.

ITAMS are known as a primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs. Non-limiting examples of ITAM containing intracellular signaling domains that are of particular use in the technology include those derived from TCRζ, FcRγ, FcRβ, CD3γ, CD3θ, CD3δ, CD3ε, CD3ζ, CD22, CD79a, CD79b, and CD66d.

One skilled in the art will be capable of introducing mutations into the nucleic acid sequence of a gene or gene product, for example ITAM, using standard techniques. For example, point mutations can be introduced via site-directed point mutagenesis, a PCR technique. Site-directed mutagenesis kits are commercially available, for instance, through New England Biolabs®; Ipswich, MA. Non-limiting examples of alternative methods to introduce point mutations to the nucleic acid sequence of a gene or gene product include cassette mutagenesis or whole plasmid mutagenesis.

In one embodiment, the ITAM utilized in the CAR is based on alternatives to CD3ζ, including mutated ITAMs from CD3ζ (which contains 3 ITAM motifs), truncations of CD3ζ, and alternative splice variants known as CD3ε, CD3θ, and artificial constructs engineered to express fusions between CD3ε or CD3θ and CD3ζ.

In one embodiment, the CD3ζ intracellular signaling sequence corresponds to a nucleotide sequence selected from SEQ ID NO: 6 or 12; or comprises a sequence selected from SEQ ID NO: 6 or 12; or comprises a sequence with at least 80%, at least 85%, at least 90%, at least 91%, at least 92%, at least 93%, at least 94%, at least 95%, at least 96%, at least 97%, at least 98%, at least 99%, or at least 100% sequence identity to a sequence selected from SEQ ID NO: 6 or 12. In one embodiment, the CD3ζ intracellular signaling sequence corresponds to an amino acid sequence selected from SEQ ID NO: 24 or 30; or comprises a sequence selected from SEQ ID NO: 24 or 30; or comprises a sequence with at least 80%, at least 85%, at least 90%, at least 91%, at least 92%, at least 93%, at least 94%, at least 95%, at least 96%, at least 97%, at least 98%, at least 99%, or at least 100% sequence identity to a sequence selected from SEQ ID NO: 24 or 30.

In one embodiment, the CD30 intracellular signaling sequence corresponds to the nucleotide sequence of SEQ ID NO: 18; or comprises the sequence of SEQ ID NO: 18; or comprises a sequence at least 80%, at least 85%, at least 90%, at least 91%, at least 92%, at least 93%, at least 94%, at least 95%, at least 96%, at least 97%, at least 98%, at least 99%, or at least 100% sequence identity to the sequence of SEQ ID NO: 18. In one embodiment, the CD30 intracellular signaling sequence corresponds to the amino acid sequence of SEQ ID NO: 36; or comprises the sequence of SEQ ID NO: 36; or comprises a sequence at least 80%, at least 85%, at least 90%, at least 91%, at least 92%, at least 93%, at least 94%, at least 95%, at least 96%, at least 97%, at least 98%, at least 99%, or at least 100% sequence identity to the sequence of SEQ ID NO: 36.

A more detailed description of CARs and CAR T cells can be found in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

In one embodiment, the CAR polypeptide further comprises a CD8 leader sequence. As used herein, a "leader sequence", also known as leader RNA, refers to a region of an mRNA that is directly upstream of the initiation codon. A leader sequence can be important for the regulation of translation of a transcript.

In one embodiment, the CD8 leader sequence corresponds to a nucleotide sequence selected from SEQ ID NO: 2, 8, or 14; or comprises a sequence selected from SEQ ID NO: 2, 8, or 14; or comprises a sequence with at least 80%, at least 85%, at least 90%, at least 91%, at least 92%, at least 93%, at least 94%, at least 95%, at least 96%, at least 97%, at least 98%, at least 99%, or at least 100% sequence identity to a sequence selected from SEQ ID NO: 2, 8, or 14. In one embodiment, the CD8 leader sequence corresponds to an amino acid sequence selected from SEQ ID NO: 20, 26, or 32; or comprises a sequence selected from SEQ ID NO: 20, 26, or 32; or comprises a sequence with at least 80%, at least 85%, at least 90%, at least 91%, at least 92%, at least 93%, at least 94%, at least 95%, at least 96%, at least 97%, at least 98%, at least 99%, or at least 100% sequence identity to a sequence selected from SEQ ID NO: 20, 26, or 32.

In one embodiment, the CAR further comprises a linker domain. As used herein "linker domain" refers to an oligo- or polypeptide region from about 2 to 100 amino acids in length, which links together any of the domains/regions of the CAR as described herein. In some embodiment, linkers can include or be composed of flexible residues such as glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. In one embodiment, the linker region is T2A derived from Thosea asigna virus. Non-limiting examples of linkers include linkers derived from Thosea asigna virus, and a linker derived from the internal ribosomal entry site (IRES) sequence.

In one embodiment, a CAR as described herein further comprises a reporter molecule, e.g., to permit for non-invasive imaging (e.g., positron-emission tomography PET scan). In a bispecific CAR that includes a reporter molecule, the first extracellular binding domain and the second extracellular binding domain can include different or the same reporter molecule. In a bispecific CAR T cell, the first CAR and the second CAR can express different or the same reporter molecule. In another embodiment, a CAR as described herein further comprises a reporter molecule (for example hygromycin phosphotransferase (hph)) that can be imaged alone or in combination with a substrate or chemical (for example 9-[4-[$^{18}$F]fluoro-3-(hydroxymethyl) butyl]guanine ([$^{18}$F]FHBG)). In another embodiment, a CAR as described herein further comprises nanoparticles at can be readily imaged using non-invasive techniques (e.g., gold nanoparticles (GNP) functionalized with $^{64}Cu^{2+}$). Labeling of CAR T cells for non-invasive imaging is reviewed, for example in Bhatnagar P, et al. Integr Biol. (Camb). 2013 January; 5 (1): 231-238, and Keu K V, et al. Sdci Transl Med. 2017 Jan. 18; 9 (373), which are incorporated herein by reference in their entireties.

GFP and mCherry are demonstrated herein as fluorescent tags useful for imaging a CAR expressed on a T cell (e.g., a CAR T cell). It is expected that essentially any fluorescent protein known in the art can be used as a fluorescent tag for this purpose. For clinical applications, the CAR need not include a fluorescent tag or fluorescent protein.

Another aspect of the invention relates to a CAR polypeptide comprising a sequence with at least 80%, at least 85%, at least 90%, at least 91%, at least 92%, at least 93%, at least 94%, at least 95%, at least 96%, at least 97%, at least 98%, at least 99%, or at least 100% sequence identity with a sequence selected from SEQ ID NO: 19, 25, or 31, or that is encoded by a nucleic acid comprising a nucleotide sequence with at least 80%, at least 85%, at least 90%, at least 91%, at least 92%, at least 93%, at least 94%, at least 95%, at least 96%, at least 97%, at least 98%, at least 99%, or at least 100% sequence identity with the sequence of SEQ ID NO: 1, 7, or 13.

Another aspect of the invention relates to a CAR polypeptide comprising a sequence selected from SEQ ID NO: 19, 25, or 31, or that is encoded by a nucleic acid comprising a nucleotide sequence selected from SEQ ID NO: 1, 7, or 13.

Another aspect of the invention relates to a CAR polypeptide comprising a sequence corresponding to a sequence selected from SEQ ID NO: 19, 25, or 31, or that is encoded by a nucleic acid comprising a nucleotide sequence selected from SEQ ID NO: 1, 7, or 13.

Another aspect of the invention described herein relates to a polypeptide complex comprising two or more (e.g., two or more, three or more, four or more, five or more, six or more, seven or more, eight or more, nine or more, or ten or more) of any of the CAR polypeptides described herein. In one embodiment, the polypeptide complex comprises three of any of the CAR polypeptides described herein.

Another aspect of the invention relates to a mammalian cell comprising any of the CAR polypeptides described herein; or a nucleic acid encoding any of the CAR polypeptides described herein. In one embodiment, the mammalian cell comprises an antibody, antibody reagent, antigen-binding portion thereof, or any of the CAR polypeptides described herein, or a nucleic acid encoding such an antibody, antibody reagent, antigen-binding portion thereof, or any of the CAR polypeptides described herein. The mammalian cell or tissue can be of human, primate, hamster, rabbit, rodent, cow, pig, sheep, horse, goat, dog or cat origin, but any other mammalian cell may be used. In a preferred embodiment of any aspect, the mammalian cell is human.

In one embodiment, the cell is a T cell. In alternate embodiments of any aspect, the cell is an immune cell. As used herein, "immune cell" refers to a cell that plays a role in the immune response. Immune cells are of hematopoietic origin, and include lymphocytes, such as B cells and T cells; natural killer cells; myeloid cells, such as monocytes, macrophages, cosinophils, mast cells, basophils, and granulocytes. In some embodiments, the cell is a T cell; a NK cell; a NKT cell; lymphocytes, such as B cells and T cells; and myeloid cells, such as monocytes, macrophages, cosinophils, mast cells, basophils, and granulocytes.

In one embodiment, the cell is obtained from an individual having or diagnosed as having cancer, a plasma cell disorder, or autoimmune disease.

"Cancer" as used herein can refer to a hyperproliferation of cells whose unique trait-loss of normal cellular control-results in unregulated growth, lack of differentiation, local tissue invasion, and metastasis, and can be leukemia, lymphoma, multiple myeloma, or a solid tumor. Non-limiting examples of leukemia include acute myeloid leukemia (AML), Chronic myeloid leukemia (CML), Acute lymphocytic leukemia (ALL), and Chronic lymphocytic leukemia (CLL). In one embodiment, the cancer is ALL or CLL. Non-limiting examples of lymphoma include Diffuse large B-cell lymphoma (DLBCL), Follicular lymphoma, Chronic lymphocytic leukemia (CLL), Small lymphocytic lymphoma (SLL), Mantle cell lymphoma (MCL), Marginal zone lymphomas, Burkitt lymphoma, hairy cell leukemia (HCL). In one embodiment, the cancer is DLBCL or Follicular lymphoma. Non-limiting examples of solid tumors include Adrenocortical Tumor, Alveolar Soft Part Sarcoma, Carcinoma, Chondrosarcoma, Colorectal Carcinoma, Desmoid Tumors, Desmoplastic Small Round Cell Tumor, Endocrine Tumors, Endodermal Sinus Tumor, Epithelioid Hemangioendothelioma, Ewing Sarcoma, Germ Cell Tumors (Solid Tumor), Giant Cell Tumor of Bone and Soft Tissue, Hepatoblastoma, Hepatocellular Carcinoma, Melanoma, Nephroma, Neuroblastoma, Non-Rhabdomyosarcoma Soft Tissue Sarcoma (NRSTS), Osteosarcoma, Paraspinal Sarcoma, Renal Cell Carcinoma, Retinoblastoma, Rhabdomyosarcoma, Synovial Sarcoma, and Wilms Tumor. Solid tumors can be found in bones, muscles, or organs, and can be sarcomas or carcinomas. It is contemplated that any aspect of the invention described herein can be used to treat all types of cancers, including cancers not listed in the instant application. As used herein, the term "tumor" refers to an abnormal growth of cells or tissues, e.g., of malignant type or benign type.

As used herein, an "autoimmune disease or disorder" is characterized by the inability of one's immune system to distinguish between a foreign cell and a healthy cell. This results in one's immune system targeting one's healthy cells for programmed cell death. Non-limiting examples of an autoimmune disease or disorder include inflammatory arthritis, type 1 diabetes mellitus, multiples sclerosis, psoriasis, inflammatory bowel diseases, SLE, and vasculitis, allergic inflammation, such as allergic asthma, atopic dermatitis, and contact hypersensitivity, rheumatoid arthritis, multiple sclerosis (MS), systemic lupus erythematosus, Graves' disease (overactive thyroid), Hashimoto's thyroiditis (underactive thyroid), chronic graft v. host disease, hemophilia with antibodies to coagulation factors, celiac disease, Crohn's disease and ulcerative colitis, Guillain-Barre syndrome, primary biliary sclerosis/cirrhosis, sclerosing cholangitis, autoimmune hepatitis, Raynaud's phenomenon, scleroderma, Sjogren's syndrome, Goodpasture's syndrome, Wegener's granulomatosis, polymyalgia rheumatica, temporal arteritis/giant cell arteritis, chronic fatigue syndrome CFS), psoriasis, autoimmune Addison's Disease, ankylosing spondylitis, Acute disseminated encephalomyelitis, antiphospholipid antibody syndrome, aplastic anemia, idiopathic thrombocytopenia purpura, Myasthenia gravis, opsoclonus myoclonus syndrome, optic neuritis, Ord's thyroiditis, pemphigus, pernicious anaemia, polyarthritis in dogs, Reiter's syndrome, Takayasu's arteritis, warm autoimmune hemolytic anemia, Wegener's granulomatosis and fibromyalgia (FM).

In one embodiment, the mammalian cell is obtained for a patient having an immune system disorder that results in abnormally low activity of the immune system, or immune deficiency disorders, which hinders one's ability to fight a foreign cell, (i.e., a virus or bacterial cell).

A plasma cell is a white blood cell produces from B lymphocytes which function to generate and release antibodies needed to fight infections. As used herein, a "plasma cell disorder or disease" is characterized by abnormal multiplication of a plasma cell. Abnormal plasma cells are capable of "crowding out" healthy plasma cells, which results in a decreased capacity to fight a foreign object, such as a virus or bacterial cell. Non-limiting examples of plasma cell disorders include amyloidosis, Waldenstrom's macroglobulinemia, osteosclerotic myeloma (POEMS syndrome), Monoclonal gammopathy of unknown significance (MGUS), and plasma cell myeloma.

T cells can be obtained from a subject using standard techniques known in the field, for example, T cells are isolated from peripheral blood taken from a patient.

A cell, for example a T cell, can be engineered to comprise any of the CAR polypeptides described herein; or a nucleic acid encoding any of the CAR polypeptides described herein. In one embodiment, a CAR polypeptide described herein is comprised in a lentiviral vector. The lentiviral vector is used to express the CAR polypeptide in a cell using infection standard techniques.

Retroviruses, such as lentiviruses, provide a convenient platform for delivery of nucleic acid sequences encoding a gene, or chimeric gene of interest. A selected nucleic acid sequence can be inserted into a vector and packaged in retroviral particles using techniques known in the art. The recombinant virus can then be isolated and delivered to cells, e.g. in vitro or ex vivo. Retroviral systems are well known in the art and are described in, for example, U.S. Pat. No. 5,219,740; Kurth and Bannert (2010) "Retroviruses: Molecular Biology, Genomics and Pathogenesis" Calster Academic Press (ISBN: 978-1-90455-55-4); and Hu and Pathak Pharmacological Reviews 2000 52:493-512; which are incorporated by reference herein in their entirety. Lentiviral system for efficient DNA delivery can be purchased from OriGene™; Rockville, MD. In alternative embodiments, the CAR polypeptide of any of the CARs described herein are expressed in the mammalian cell via transfection or electroporation of an expression vector comprising nucleic acid encoding the CAR. Transfection or electroporation methods are known in the art.

Efficient expression of the CAR polypeptide of any of the CAR polypeptides described herein can be assessed using standard assays that detect the mRNA, DNA, or gene product of the nucleic acid encoding the CAR. For example, RT-PCR, FACS, northern blotting, western blotting, ELISA, or immunohistochemistry.

In one embodiment, the CAR polypeptide of any of the CAR polypeptides described herein is constitutively expressed. In one embodiment, the CAR polypeptide of any of the CAR polypeptides described herein is encoded by recombinant nucleic acid sequence.

One aspect of the invention described herein relates to a method to a method of treating cancer, a plasma cell disorder, amyloidosis, or an autoimmune disease in a subject, the method comprising: engineering a T cell to comprise any of the CAR polypeptides described herein on the T cell surface; administering the engineered T cell to the subject.

Another aspect of the invention described herein relates to a method of treating cancer, a plasma cell disorder, or an autoimmune disease in a subject, the method comprising administering a cell comprising any of the CAR polypeptides described herein, or a nucleic acid encoding any of the CAR polypeptides described herein.

In one embodiment, the method further comprises activating or stimulating the CAR-T prior to administering the cell to the subject, e.g., according to a method as described elsewhere herein.

In one embodiment, the cancer cell comprises the tumor antigens BAFF+, BCMA+, and/or TACI+ cancer. In one embodiment, cancer is multiple myeloma or smoldering myeloma.

Administration

In some embodiments, the methods described herein relate to treating a subject having or diagnosed as having cancer, a plasma cell disease or disorder, or an autoimmune disease or disorder with a mammalian cell comprising any of the CAR polypeptides described herein, or a nucleic acid encoding any of the CAR polypeptides described herein. As used herein, a "CAR T cell as described herein" refers to a mammalian cell comprising any of the CAR polypeptides described herein, or a nucleic acid encoding any of the CAR polypeptides described herein. As used herein, a "condition" refers to a cancer, a plasma cell disease or disorder, or an autoimmune disease or disorder. Subjects having a condition can be identified by a physician using current methods of diagnosing the condition. Symptoms and/or complications of the condition, which characterize these conditions and aid in diagnosis are well known in the art and include but are not limited to, fatigue, persistent infections, and persistent bleeding. Tests that may aid in a diagnosis of, e.g. the condition, but are not limited to, blood screening and bone marrow testing, and are known in the art for a given condition. A family history for a condition, or exposure to risk factors for a condition can also aid in determining if a subject is likely to have the condition or in making a diagnosis of the condition.

The compositions described herein can be administered to a subject having or diagnosed as having a condition. In some embodiments, the methods described herein comprise administering an effective amount of activated CAR T cells described herein to a subject in order to alleviate a symptom of the condition. As used herein, "alleviating a symptom of the condition" is ameliorating any condition or symptom associated with the condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. In one embodiment, the compositions described herein are administered systemically or locally. In a preferred embodiment, the compositions described herein are administered intravenously. In another embodiment, the compositions described herein are administered at the site of the tumor.

The term "effective amount" as used herein refers to the amount of activated CAR T cells needed to alleviate at least one or more symptom of the disease or disorder, and relates to a sufficient amount of the cell preparation or composition to provide the desired effect. The term "therapeutically effective amount" therefore refers to an amount of activated CAR T cells that is sufficient to provide a particular anti-condition effect when administered to a typical subject. An effective amount as used herein, in various contexts, would also include an amount sufficient to delay the development of a symptom of the disease, alter the course of a symptom disease (for example but not limited to, slowing the progression of a condition), or reverse a symptom of the condition. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be evaluated by standard pharmaceutical procedures in cell cultures or experimental animals. The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of activated CAR T cells, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for bone marrow testing, among others. The dosage can be determined by a physician and adjusted, as necessary, to suit observed effects of the treatment.

In one aspect of the invention, the technology described herein relates to a pharmaceutical composition comprising activated CAR T cells as described herein, and optionally a pharmaceutically acceptable carrier. The active ingredients of the pharmaceutical composition at a minimum comprise activated CAR T cells as described herein. In some embodiments, the active ingredients of the pharmaceutical composition consist essentially of activated CAR T cells as described herein. In some embodiments, the active ingredients of the pharmaceutical composition consist of activated CAR T cells as described herein. Pharmaceutically acceptable carriers for cell-based therapeutic formulation include saline and aqueous buffer solutions, Ringer's solution, and serum component, such as serum albumin, HDL and LDL. The terms such as "excipient", "carrier", "pharmaceutically acceptable carrier" or the like are used interchangeably herein.

In some embodiments, the pharmaceutical composition comprising activated CAR T cells as described herein can be a parenteral dose form. Since administration of parenteral dosage forms typically bypasses the patient's natural defenses against contaminants, the components apart from the CAR T cells themselves are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Any of these can be added to the activated CAR T cells preparation prior to administration.

Suitable vehicles that can be used to provide parenteral dosage forms of activated CAR T cells as disclosed within are well known to those skilled in the art. Examples include, without limitation: saline solution; glucose solution; aqueous vehicles including but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Dosage

"Unit dosage form" as the term is used herein refers to a dosage for suitable one administration. By way of example a unit dosage form can be an amount of therapeutic disposed in a delivery device, e.g., a syringe or intravenous drip bag. In one embodiment, a unit dosage form is administered in a single administration. In another, embodiment more than one unit dosage form can be administered simultaneously.

In some embodiments, the activated CAR T cells described herein are administered as a monotherapy, i.e., another treatment for the condition is not concurrently administered to the subject.

A pharmaceutical composition comprising the T cells described herein can generally be administered at a dosage of $10^4$ to $10^9$ cells/kg body weight, in some instances $10^5$ to $10^6$ cells/kg body weight, including all integer values within those ranges. If necessary, T cell compositions can also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated CAR T cells to a subject and then subsequently redraw blood (or have an apheresis performed), activate T cells therefrom as described herein, and reinfuse the patient with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc.

Modes of administration can include, for example intravenous (i.v.) injection or infusion. The compositions described herein can be administered to a patient transarterially, intratumorally, intranodally, or intramedullary. In some embodiments, the compositions of T cells may be injected directly into a tumor, lymph node, or site of infection. In one embodiment, the compositions described herein are administered into a body cavity or body fluid (e.g., ascites, pleural fluid, peritoneal fluid, or cerebrospinal fluid).

In a particular exemplary aspect, subjects may undergo leukapheresis, wherein leukocytes are collected, enriched, or depleted ex vivo to select and/or isolate the cells of interest, e.g., T cells. These T cell isolates can be expanded by contact with an aAPC as described herein, e.g., an aAPC expressing anti-CD28 and anti-CD3 CDRs as described herein and treated such that one or more CAR constructs of the invention may be introduced, thereby creating a CAR T cell. Subjects in need thereof can subsequently undergo standard treatment with high dose chemotherapy followed by peripheral blood stem cell transplantation. Following or concurrent with the transplant, subjects can receive an infusion of the expanded CAR T cells. In one embodiment, expanded cells are administered before or following surgery.

In some embodiments, lymphodepletion is performed on a subject prior to administering one or more CAR T cell as described herein. In such embodiments, the lymphodepletion can comprise administering one or more of melphalan, Cytoxan®, cyclophosphamide, and fludarabine.

The dosage of the above treatments to be administered to a patient will vary with the precise nature of the condition being treated and the recipient of the treatment. The scaling of dosages for human administration can be performed according to art-accepted practices.

In some embodiments, a single treatment regimen is required. In others, administration of one or more subsequent doses or treatment regimens can be performed. For example, after treatment biweekly for three months, treatment can be repeated once per month, for six months or a year or longer. In some embodiments, no additional treatments are administered following the initial treatment.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further cells, discontinue treatment, resume treatment, or make other alterations to the treatment regimen. The dosage should not be so large as to cause adverse side effects, such as cytokine release syndrome. Generally, the dosage will vary with the age, condition, and sex of the patient and can be determined by one of skill in the art. The dosage can also be adjusted by the individual physician in the event of any complication.

Combinational Therapy

The activated CAR T cells described herein can be used in combination with other known agents and therapies. In one embodiment, the subject is further administered an anti-BCMA therapy. In one embodiment, the subject is resistant to anti-BCMA therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The activated CAR T cells described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed. The CAR T therapy and/or other therapeutic agents, procedures or modalities can be administered during periods of active disorder, or during a period of remission or less active disease. The CAR T therapy can be administered before another treatment, concurrently with the treatment, post-treatment, or during remission of the disorder.

When administered in combination, the activated CAR T cells and the additional agent (e.g., second or third agent), or all, can be administered in an amount or dose that is higher, lower or the same as the amount or dosage of each agent used individually, e.g., as a monotherapy. In certain embodiments, the administered amount or dosage of the activated CAR T cells, the additional agent (e.g., second or third agent), or all, is lower (e.g., at least 20%, at least 30%, at least 40%, or at least 50%) than the amount or dosage of each agent used individually. In other embodiments, the amount or dosage of the activated CAR T cells, the additional agent (e.g., second or third agent), or all, that results in a desired effect (e.g., treatment of cancer) is lower (e.g., at least 20%, at least 30%, at least 40%, or at least 50% lower) than the amount or dosage of each agent individually required to achieve the same therapeutic effect. In further embodiments, the activated CAR T cells described herein can be used in a treatment regimen in combination with surgery, chemotherapy, radiation, an mTOR pathway inhibitor, immunosuppressive agents, such as cyclosporin, azathioprine, methotrexate, mycophenolate, and FK506, antibodies, or other immunoablative agents such as CAMPATH®, anti-CD3 antibodies or other antibody therapies, cytoxin, fludarabine, rapamycin, mycophenolic acid, steroids, FR901228, cytokines, or a peptide vaccine, such as that described in Izumoto et al. 2008 J Neurosurg 108:963-971.

In one embodiment, the activated CAR T cells described herein can be used in combination with a checkpoint inhibitor. Exemplary checkpoint inhibitors include anti-PD-1 inhibitors (Nivolumab, MK-3475, Pembrolizumab, Pidilizumab, AMP-224, AMP-514), anti-CTLA4 inhibitors (Ipilimumab and Tremelimumab), anti-PDL1 inhibitors (Atezolizumab, Avelomab, MSB0010718C, MEDI4736, and MPDL3280A), and anti-TIM3 inhibitors.

In one embodiment, the activated CAR T cells described herein can be used in combination with a chemotherapeutic agent. Exemplary chemotherapeutic agents include an anthracycline (e.g., doxorubicin (e.g., liposomal doxorubicin)), a *vinca* alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide). General chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BICNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegen®), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurca (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®). Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Hacmanthamine®, Nordopan®, Uracil nitrogen mustard®, Uracillost®, Uracilmostaza®, Uramustine®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), tricthylenethiophosphoramine, Temozolomide (Temodar®), thiotepa (Thioplex®), busulfan (Busilvex®, Mylderan®), carmustine (BICNU®), lomustine (CecNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BICNU®); Bendamustine (Treanda®); Busulfan (Busulfex® and Mylderan®); Carboplatin (Paraplatin®); Lomustine (also known as CCNU, CecNUR); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifcx®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®). Exemplary mTOR inhibitors include, e.g., temsirolimus; ridaforolimus (formally known as deforolimus, (1R,2R,45)-4-[(2R)-2 [(1R,95,125, 15R, 16E, 18R, 19R,21R,235,24E,26E,28Z, 305,325,35R)-1,18-dihydroxy-19,30-dimethoxy-15,17,21, 23,29,35-hexamethyl-2,3,10,14,20-pentaoxo-1 1,36-dioxa-4-azatricyclo[30.3.1.04'9]hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (Afinitor® or RADOOI); rapamycin (AY22989, Sirolimus®); simapimod (CAS 164301-51-3); emsirolimus, (5-{2,4-Bis [(35)-3-methylmorpholin-4-yl] pyrido[2,3-(i]pyrimidin-7-yl}-2-methoxyphenyl) methanol (AZD8055); 2-Amino-8-[iraw5,-4-(2-hydroxyethoxy) cyclohexyl]-6-(6-methoxy-3-pyridinyl)-4-methyl-pyrido[2, 3-JJpyrimidin-7 (8H)-one (PF04691502, CAS 1013101-36-4); and N2-[1,4-dioxo-4-[[4-(4-oxo-8-phenyl-4H-1-benzo-pyran-2-yl) morpholinium-4-yl]methoxy|butyl]-L-arginylglycyl-L-a-aspartyIL-serine-, inner salt (SF1126, CAS 936487-67-1), and XL765. Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics®). Exemplary anthracyclines include, e.g., doxorubicin (Adriamycin® and Rubex®); bleomycin (lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin. Exemplary *vinca* alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®). Exemplary proteosome inhibitors include bortezomib (Velcade®); carfilzomib (PX-171-007, (5)-4-Methyl-N-((5)-1-(((5)-4-methyl-1-((R)-2-methyloxiran-2-yl)-1-oxopentan-2-yl) amino)-1-oxo-3-phenylpropan-2-yl)-2-((5)-2-(2-morpholinoacetamido)-4-phenylbutanamido)-pentanamide); marizomib (NPT0052); ixazomib citrate (MLN-9708); delanzomib (CEP-18770); and O-Methyl-N-[(2-methyl-5-thiazolyl) carbonyl]-L-seryl-O-methyl-N-[(IIS')-2-[(2R)-2-methyl-2-oxiranyl]-2-oxo-1-(phenylmethyl) ethyl]-L-serinamide (ONX-0912).

One of skill in the art can readily identify a chemotherapeutic agent of use (e.g. see Physicians' Cancer Chemotherapy Drug Manual 2014, Edward Chu, Vincent T. De Vita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In an embodiment, activated CAR T cells described herein are administered to a subject in combination with a molecule that decreases the activity and/or level of a molecule targeting GITR and/or modulating GITR functions, a molecule that decreases the Treg cell population, an mTOR inhibitor, a GITR agonist, a kinase inhibitor, a non-receptor tyrosine kinase inhibitor, a CDK4 inhibitor, and/or a BTK inhibitor.

Efficacy

The efficacy of activated CAR T cells in, e.g. the treatment of a condition described herein, or to induce a response as described herein (e.g. a reduction in cancer cells) can be determined by the skilled clinician. However, a treatment is considered "effective treatment," as the term is used herein, if one or more of the signs or symptoms of a condition described herein is altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

Efficacy can also be measured by a failure of an individual to worsen as assessed by hospitalization, or need for medical interventions (i.e., progression of the disease is halted). Methods of measuring these indicators are known to those of skill in the art and/or are described herein.

Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy of a given approach can be assessed in animal models of a condition described herein, for example treatment of ALL. When using an experimental animal model, efficacy of treatment is evidenced when a statistically significant change in a marker is observed.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting Some embodiments of the technology described herein can be defined according to any of the following numbered paragraphs:

1. A chimeric antigen receptor (CAR) polypeptide comprising:
   a) one or more extracellular domains comprising a portion of Tumor Necrosis Factor (TNF) superfamily receptor ligand;
   b) a hinge and transmembrane domain;
   c) a co-stimulatory domain; and
   d) an intracellular signaling domain.

2. The CAR polypeptide of paragraph 1, wherein the TNF superfamily receptor ligand is A Proliferation-Inducing Ligand (APRIL).

3. The CAR polypeptide of paragraph 1, wherein the TNF superfamily receptor ligand is TNF-alpha, lymphotoxin beta, OX40L, CD154, FasL, LIGHT, TLIA, CD70, Siva, CD153, 4-1BB ligand, TRAIL, RANKL, TWEAK, BAFF, CAMLG, LIGHT, NGF, BDNF, NT-3, NT-4, GITR ligand, TLIA, or EDA-A2.

4. The CAR polypeptide of any one of paragraphs 1-3, further comprising a CD8 leader sequence.

5. The CAR polypeptide of paragraph 4, wherein the CD8 leader sequence comprises the sequence selected from SEQ ID NO: 20, 26, or 32.

6. The CAR polypeptide of any of paragraphs 2, 4, or 5, wherein the portion of APRIL does not comprise a lysine-rich region of APRIL.

7. The CAR polypeptide of any of paragraphs 2 or 4-6, wherein the portion of APRIL comprises the sequence selected from SEQ ID NO: 21, 27, or 33.

8. The CAR polypeptide of any of paragraphs 1-7, wherein the hinge and transmembrane domain comprises the hinge and transmembrane domain of CD8 or 4-1BB.

9. The CAR polypeptide of any of paragraphs 1-8, wherein the CD8 hinge and transmembrane domain sequence comprises the sequence of SEQ ID NO: 22.

10. The CAR polypeptide of any of paragraphs 1-9, wherein the 4-1BB hinge and transmembrane domain sequence comprises the sequence selected from SEQ ID NO: 28 or 34.

11. The CAR polypeptide of any of paragraphs 1-10, wherein the intracellular signaling domain comprises the signaling domain of CD3ζ, CD3ε, or CD3θ.

12. The CAR polypeptide of any of paragraphs 1-11, wherein the CD3ζ intracellular signaling domain sequence comprises the sequence selected from SEQ ID NO: 24 or 30.

13. The CAR polypeptide of any of paragraphs 1-12, wherein the CD3θ intracellular signaling domain sequence comprises the sequence of SEQ ID NO: 36.

14. The CAR of any of paragraphs 1-13, wherein the co-stimulatory domain is the intracellular domain selected from the group consisting of 4-1BB ICD, CD28 ICD, CD27 ICD, ICOS ICD, and OX40 ICD.

15. The CAR polypeptide of any of paragraphs 1-14, wherein the co-stimulatory domain is the intracellular domain of 4-1BB.

16. The CAR polypeptide of paragraph 15, wherein the intracellular domain of 4-1BB sequence comprises a sequence selected from SEQ ID NO: 23, 29, or 35.

17. The CAR polypeptide of any one of paragraphs 1-16, wherein the CAR polypeptide comprises two or more extracellular domains comprising a portion of TNF superfamily receptor ligand.

18. The CAR polypeptide of paragraph 17, wherein the CAR polypeptide comprises three extracellular domains comprising a portion of TNF superfamily receptor ligand.

19. A CAR polypeptide comprising at least 95% identity with a sequence selected from SEQ ID NO: 19, 25, or 31, or that is encoded by a sequence comprising at least 95% identity with a sequence selected from SEQ ID NO: 1, 7, or 13.

20. A CAR polypeptide comprising a sequence selected from SEQ ID NO: 19, 25, or 31, or that is encoded by a sequence selected from SEQ ID NO: 1, 7, or 13.

21. A CAR polypeptide comprising a sequence corresponding to a sequence selected from SEQ ID NO: 19, 25, or 31, or that is encoded by a sequence selected from SEQ ID NO: 1, 7, or 13.

22. A polypeptide complex comprising two or more of the CAR polypeptides of any one of paragraphs 1-21.

23. The polypeptide complex of paragraph 22, wherein the polypeptide complex comprises three CAR polypeptides of any one of paragraphs 1-21.

24. A mammalian cell comprising;
  a) a CAR polypeptide of any of paragraphs 1-21;
  b) a nucleic acid encoding a CAR polypeptide of any of paragraphs 1-21; or
  c) a polypeptide complex of paragraph 22 or 23.

25. The cell of paragraph 24, wherein the cell is a T cell.

26. The cell of paragraph 24 or 25, wherein the cell is a human cell.

27. The cell of any of paragraphs 24-26, wherein the cell is obtained from an individual having or diagnosed as having cancer, a plasma cell disorder, or autoimmune disease.

28. A method of treating cancer, a plasma cell disorder, amyloidosis, or an autoimmune disease in a subject, the method comprising:
  a) engineering a T cell to comprise a CAR of any of paragraphs 1-21 on the T cell surface;
  b) administering the engineered T cell to the subject.

29. A method of treating cancer, a plasma cell disorder, or an autoimmune disease in a subject, the method comprising administering a cell of any of paragraphs 24-27 to the subject.

30. The method of paragraph 28 or 29, wherein the cancer is BAFF+, BCMA+ and/or TACI$^+$.

31. The method of any of paragraphs 28-30, wherein the subject is further administered an anti-BCMA therapy.

32. The method of any of paragraphs 28-31, wherein the subject is resistant to anti-BCMA therapies.

33. The method of any of paragraphs 28-32, wherein the cancer is multiple myeloma or smoldering myeloma.

34. The method of any of paragraphs 28-32, wherein the autoimmune disease is selected from the group consisting of hemophilia with antibodies to coagulation factors, myasthenia gravis, multiple sclerosis, and chronic graft v. host disease.

35. A composition comprising the CAR polypeptide of any one of paragraphs 1-21, the polypeptide complex of paragraph 22 or 23, or the cell of any one of paragraphs 24-27 formulated for the treatment of cancer.

36. The composition of paragraph 35, further comprising a pharmaceutically acceptable carrier.

EXAMPLES

Example 1

Chimeric antigen receptors based on the extracellular domain of the APRIL (A PRoliferation-Inducing ligand) fused to transmembrane domains of CD8 or 4-1BB and the signaling domain of the T cell activating receptors CD3 zeta, CD3 eta, or CD3 theta are described herein. These CARs can overcome resistance to anti-BCMA targeted therapies and utilize dimerizing and trimerizing transmembrane domains for optimal function. These CARs are contemplated for the treatment of cancer, e.g., multiple myelomas, plasma cell disorders, and/or severe autoimmune disease.

It was contemplated by the inventors that the natural ligand for BCMA could be used to engineer an antigen-binding moiety to generate anti-myeloma CAR T cells. CAR T cells based on scFvs and on the natural ligand (APRIL) were compared for cytotoxic activity, antigen-specific proliferation, and cytokine production in myeloma cell lines expressing BCMA, TACI, and/or BAFF-receptor.

BCMA is a small type-III transmembrane protein that binds BAFF with low affinity and APRIL with high affinity[48]; BCMA signaling protects myeloma cells from apoptosis[49]. BCMA has two close family members: TACI and BAFF-receptor. TACI is expressed at similar levels and stages of B cell development, whereas BAFF receptor is expressed in earlier stages of B cell development and has higher affinity for binding BAFF than APRIL[3]. The intracellular domains of both BCMA and TACI interact with TRAFs, and likely have redundant functions in promoting plasma cell survival[50]. Antibodies and scFvs raised specifically against BCMA are less likely to cross-react with TACI given the small epitope-binding regions of BCMA than vice versa. In fact, the literature indicates that none of the anti-BCMA products (antibodies, scFvs, or bi-specific T cell engagers) in the clinical setting cross-react with BAFF-receptor or TACI[51].

One of the greatest challenges in designing a CAR T cell with novel specificity is determining off-tumor expression of the target. Reassuringly, anti-BCMA products have been considered safe in a variety of clinical settings, without evidence of off-tumor reactivity[51]. CAR T cell products directed to BCMA have been associated with cytokine release syndrome. However, publicly available data from TCGA, ENCODE, BLUEPRINT, and GTEX indicate that the expression profiles of BCMA and TACI appear to be safe for targeting via CAR T cells (data not shown); neither molecule is expressed by healthy adult tissues other than plasma cells and B cells, and both are expressed at high levels in multiple myeloma and chronic lymphocytic leukemia. Further, given emerging data regarding antigen-escape variants in patients with acute lymphoblastic leukemia receiving anti-CD19-directed CAR T cells[33,52,53], developing a re-directed T cell that binds two antigens with similar expression profiles and signaling redundancy can provide a mechanism of avoiding escape variants.

There are three putative ways to generate one CAR designed to react to two antigens. (1) Generate an scFv that cross-reacts with both targets. The danger with this strategy is that a promiscuous scFv may also have off-tumor reactivity that could be difficult to predict in the pre-clinical setting. (2) Generate a CAR composed of scFvs with two different specificities in tandem. This strategy is being pursued for CD19 and CD22[54] and for CD19 and CD20[55], for example. However, the optimal spacing between the two scFvs must be determined empirically, and formation of cross-reactive diabody-scFvs could also result in off-target binding. This method is feasible but challenging and expensive, especially since scFvs must be generated and tested independently, and then combined[56]. (3) Develop a high-affinity ligand that binds to both receptors and fuse it to the remaining components of the chimeric antigen receptor (transmembrane and signaling domains). In this case, the inventors appreciated a unique opportunity to utilize the third approach with APRIL (FIG. 1).

There are four potential issues with respect to using APRIL as an extracellular binding domain for a CAR T cell: (1) APRIL naturally forms a homo-trimer, whereas scFv-based CARs are thought to homodimerize[43,57,58]. It is not clear whether APRIL homodimers bind BCMA/TACI, or if CARs can signal if they form trimers. Of note, 4-1BB also naturally forms a trimer, and yet CAR constructs that include a 4-1BB costimulation domain are highly active, indicating flexibility of function between homodimerizing and homotrimerizing TNF-related proteins. Formation of active CARs with suitable binding to BCMA/TACI is easily tested in vitro via flow cytometry with soluble BCMA and TACI, as well as via cytotoxicity assays against target cells expressing BCMA and TACI. (2) APRIL also binds to heparan sulfate chains associated with proteoglycans of the syndecan family (including CD138, syndecan-1), which may have more disseminated expression than TACI and BCMA; thus, there is increased potential for off-tumor activity. Specifically, binding of APRIL to heparan sulfate chains occurs via the lysine-rich region in its N-terminus, whereas the TNF-like region interacts with the BCMA and TACI receptors[59]. In myeloma cells, binding to CD138 can act as a co-receptor for APRIL binding to TACI[60]. Due to the distance between putative binding of the APRIL CAR and the heparan sulfate proteoglycan molecules, it is not expected that this interaction will result in cytotoxicity[54], but this prediction can be tested systematically in cell lines expressing CD138 without TACI or BCMA. In addition, a form of APRIL that lacks the N-terminal lysine-rich region to avoid binding to heparan sulfate chains can be generated. (3) There is a putative receptor for APRIL, which has not been confirmed but is hypothesized to be expressed on epithelial tissue[61]; this interaction would necessitate testing and modeling of APRIL-CAR directed activity against epithelial cells. (4) The natural APRIL sequence is cleaved from its endogenous transmembrane domain, and can promote survival signals in myeloma cells; it is therefore proposed to anchor only the N-terminus domains of APRIL (distal to the cleavage site) to the transmembrane and intracellular domains of the CAR, so as to avoid shedding APRIL from the CAR T cells.

Experimental Design

Described herein is the testing of a small panel of scFv sequences specific for BCMA based on published sequences of murine and phage-display derived anti-BCMA constructs in the context of our CAR backbone. In addition, an APRIL-based CAR, utilizing only the most extracellular portion of APRIL domains that bind to BCMA and TACI is characterized. Also described is an N-terminus-truncated version of APRIL to eliminate the lysine-rich region that binds to heparan sulfate chains. Next, lentiviral vectors with two scFv- and two APRIL-based CARs are used to test primary T cells for expression of the CAR via flow cytometry after staining with biotinylated soluble BCMA-Ig and TACI-Ig (commercially available). Finally, it is verified that APRIL-based CARs do not secrete or cleave APRIL as a soluble protein, by collecting supernatants from T cell cultures and measuring soluble APRIL via ELISA.

Target cell lines based on K562 cells were engineered to express BAFF-receptor, BCMA, and TACI singly and in combination via lentiviral transduction. K562 cells expressing CD138 (syndecan-1), are engineered to test for binding of APRIL-based CARs to this heparan sulfate proteoglycan. These lines provide targets and antigen-presenting cells in which to test anti-BCMA scFv-CARs and APRIL-CARs for their ability to lyse BCMA- and TACI-expressing targets, and undergo antigen-specific proliferation. CD138-bearing targets are tested for sensitivity to APRIL-CAR mediated binding and toxicity in the presence and absence of heparin (which eliminates binding between APRIL and heparan sulfate[60]). Specific lysis is measured by co-culturing effector cells with target cells at various (E:T) ratios; target cells are also genetically modified to express luciferase, such that viable target cells can be quantified by measuring light emission.

The cross-reactivity of binding to the CARs is also measured by using soluble BCMA and soluble TACI as staining reagents for CAR T cells to be evaluated by flow cytometry. Anti-BCMA scFv-CAR T cells and APRIL-CAR T cells are tested for their ability to proliferate in an antigen-specific manner in response to targets presenting BCMA, TACI, or both. Proliferation is measured by dilution of the fluorescent dye CFSE, and by counting T cells over the course of one to two weeks following antigen stimulation.

Finally, primary human plasma cells from patients with multiple myeloma are examined for their expression of BCMA, TACI, and BAFF receptor by standard flow cytometry. The MGH myeloma group has a biobank of bone marrow specimens from patients with multiple myeloma, from which de-identified samples can be examined. The levels of BCMA, TACI, and BAFF-R in plasma cells from 30 patients with measurable plasma cell burden can be quantified. Where feasible, anti-BCMA and APRIL-based CAR T cells are co-cultured with viable primary myeloma plasma cells; co-cultures are evaluated for viability of the myeloma cells and proliferation of the CAR T cells. In addition, the levels of BCMA and TACI expression in the bone marrow plasma cells of patients who have received anti-BCMA scFv-based CAR T cells can be examined. In this case, BCMA and TACI expression can be quantified in baseline marrow samples and in a bone marrow sample that is collected at 1-3 months following treatment, or at relapse, in patients treated at our site.

It is expected that scFv-based and APRIL-based CAR-transduced primary T cells exert cytotoxic activity and proliferate in response to BCMA-expressing target cells, be they K562-transduced cell lines, myeloma cell lines such as U266 and RPMI-8226, or primary patient myeloma cells. In contrast, only APRIL-based CARs exert cytotoxic effects against cell lines expressing only TACI. APRIL-based CARs bind soluble versions of both TACI and BCMA, whereas scFv-based anti-BCMA CARs bind only to soluble BCMA.

Untransduced T cells and CD19-CAR transduced T cells are not expected to display cytotoxic activity in response to BCMA-expressing target cells or multiple myeloma cell lines; these cells serve as negative controls. APRIL-based CARs are not expected to secrete soluble APRIL into the culture medium; if detectable secretion occurs, as measured by ELISA or Luminex™ analysis of the supernatant, the CAR can be redesigned to an alternative format (based on an scFv that is cross-reactive between TACI and BCMA), or including fewer amino acid domains of the extracellular distal (C-terminus) portion of APRIL to further eliminate possible cleavage sites. APRIL-based and scFv-based anti-BCMA CARs are expected to yield similar levels of cytokine production, and proliferate similarly in response to BCMA-expressing targets, but only APRIL-based CARs are expected to produce IFNγ and IL-2 in response to TACI-expressing targets.

APRIL-based CARs are not expected to mediate cytolysis of CD138-expressing targets in the absence of TACI or BCMA due to the distance between binding sites; comparisons will be made to anti-CD138-scFv-based CARs, which have already been shown to eliminate myeloma cell lines in vitro and in vivo. However, if CD138-directed cytotoxicity is not observed with APRIL-based CARs, the heparan sulfate mechanism can be verified by adding heparin to abrogate this interaction. An N-terminus-truncated version of APRIL, so as to eliminate the lysine-rich region but maintain only the TNF-like region as the extracellular binding domain of the CAR, is also described herein. If there is any remaining question as to potential toxicity of APRIL-based CARs against heparan sulfate proteoglycans or epithelial tissues, cytotoxicity can be tested against primary cultured keratinocytes and in our skin-graft in vivo model. In this model, immunodeficient mice are grafted with human skin (discarded tissue from plastic surgery or circumcisions) and allowed to heal. Skin-toxicity of CAR T cells is monitored histopathologically from biopsies or graft excisions; skin toxicity is manifested as lymphocytic infiltration with destruction of the epidermal/dermal junction and keratinocyte apoptosis, which is the pathognomonic sign of graft-vs.-host disease. If there is remaining concern about possible epithelial toxicity of APRIL-based CAR T cells, safety of APRIL-based CARs can be evaluated in this model.

In bone marrow samples obtained from patients with multiple myeloma, it is expected to confirm high levels of expression of TACI and BCMA in plasma cells, with lower levels of BAFF-receptor as determined by flow cytometry and appropriate controls (fluorescence minus one).

Figure 3:
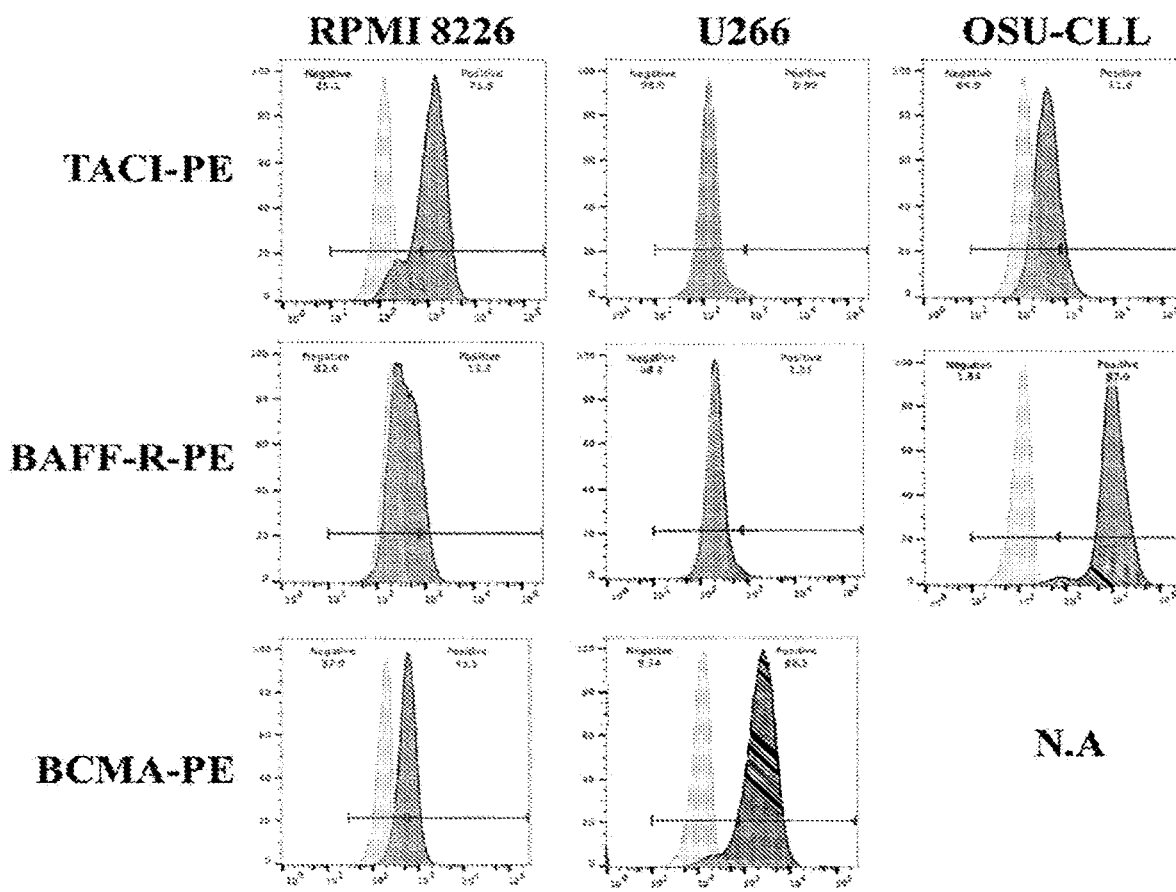
FIG. 3 depicts target surface expression in the indicated cell types.

Example 2: Limiting Antigen Escape in Multiple Myeloma by Dual Antigen-Targeting Despite recent advantages in treatment, multiple myeloma still remains an incurable disease. Several recent clinical trials of CAR T cells directed against B cell maturation antigen (BCMA) have lead to clinical responses including complete remission in patients with multiple myeloma. However, treatment failure due to antigen-loss of BCMA has already been described in some patients. The transmembrane activator and calcium modulator and cyclophilin ligand interactor (TACI) is thought to have a redundant role to BCMA in maintaining plasma cell survival, and is also highly expressed on multiple myeloma cells. In the work described herein, the natural ligand for BCMA and TACI, APRIL, was utilized as a CAR binding moiety. The approach prevents disease relapse due to antigen-escape by dual targeting of multiple surface antigens in multiple myeloma (FIG. 3).

Materials and Methods

Figure 2:
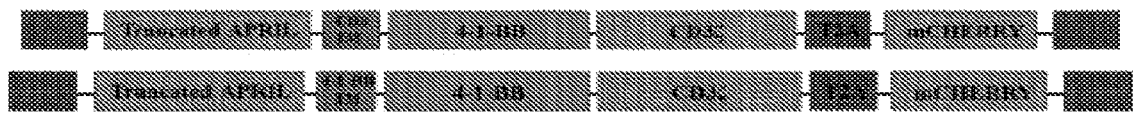
FIG. 2 depicts a schematic diagram of certain embodiments of the CARs described herein. It is expected that use of the 4-1BB transmembrane domain is more likely to promote trimerization.

CAR constructs were generated with scFv-based anti-BCMA, and APRIL-based CARs bearing different hinge and transmembrane domains (CD8 or 4-1BB), all fused to 4-1BB and CD3 zeta (FIG. 2). Human primary T cells were lentivirally transduced with either an anti-BCMA-CAR or APRIL-based CARs. Cytotoxicity, proliferation and cytokine production was evaluated in vitro against a panel of cell lines with varying expression levels of BCMA and TACI and in vivo in a xenograft model of multiple myeloma.

Results

Increased activation in response to BCMA+ or TACI+ target cells, were seen for APRIL-based CARs. Anti-BCMA-CAR was only activated in response to BCMA+ target cells. Both BCMA and APRIL-CD8 hinge/transmembrane CARs displayed antigen-specific cytotoxicity. Interestingly, lower levels were found in cytokine production for APRIL-CD8 hinge/transmembrane CAR compared to anti-BCMA-CAR. This observation is likely to reflect the difference in binding affinity between using APRIL or an scFv as CAR binding moiety. Altering the hinge/transmembrane domain to 4-1BB in the APRIL-CAR lead to a reduction in cytotoxicity and limited cytokine production. Ongoing studies, using a xenograft model have shown complete tumor remission in some mice treated with anti-BCMA-CAR or APRIL-CD8 hinge/transmembrane CAR.

DISCUSSION

Described herein is the design of a CAR, based on the natural ligand APRIL, able to recognize both BCMA and TACI in order to limit potential antigen-escape in multiple myeloma. Inclusion of the CD8 hinge and transmembrane region was optimal for APRIL CAR function. Despite the cytotoxic efficacy of the APRIL CAR against tumor cells, lower levels of effector cytokine production were seen. This is an important finding, since CAR T cell therapy can lead to cytokine release syndrome.

Example 3

Figure 4:
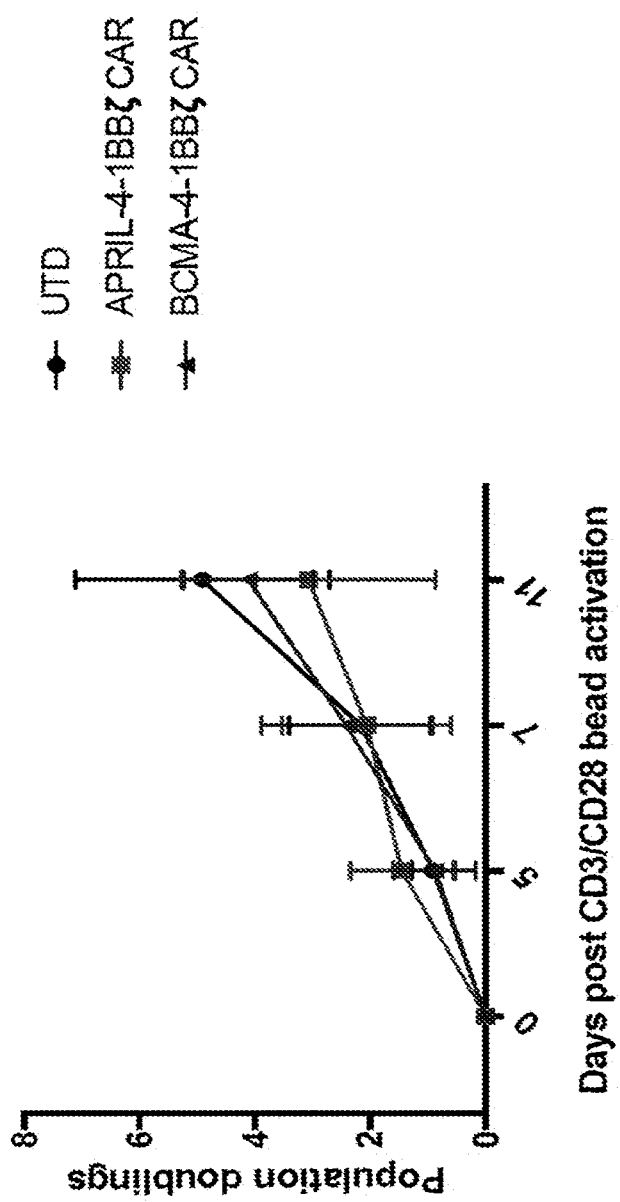
FIG. 4 depicts a growth curve for cells expressing APRIL or BCMA CARs.
Figure 5A:
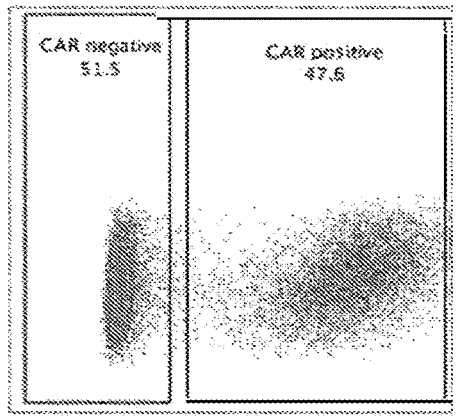
FIG. 5A depicts the CAR-T cell transduction efficiency of APRIL CAR.
Figure 5A:
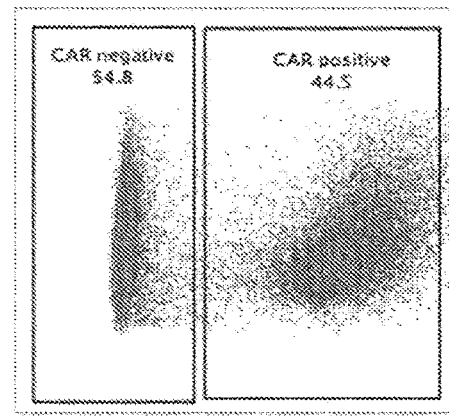
Figure 5B:
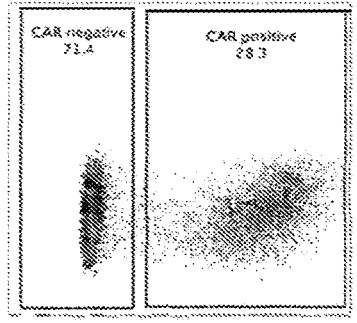
FIG. 5B depicts the CAR-T cell transduction efficiency of BCMA CAR. X-axis is mCherry, y-axis is side scatter. Cells are gated on live CD3+ T cells.
Figure 5B:
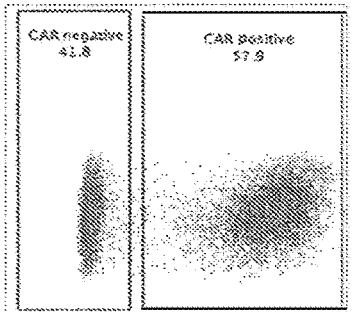
Figure 5B:
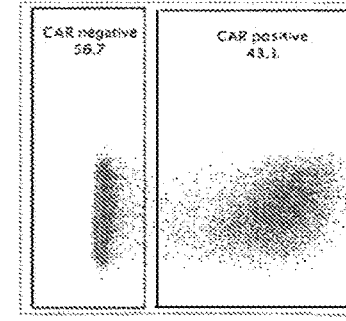

Human T cells were stimulated with CD3/28 beads on day 0 and transduced with lentiviral vector coding for APRIL-CD8TM-4-1BBzCAR expressed APRIL-CD8TM-4-1BBζ CAR or BCMA-CD8TM-4-1BBζCAR. Cells were counted beginning on day 0 and their growth was plotted as population doublings (FIG. 4). Transduction efficiency was measured by mCherry (reporter) positivity (FIG. 5A-5B).

Figure 6:
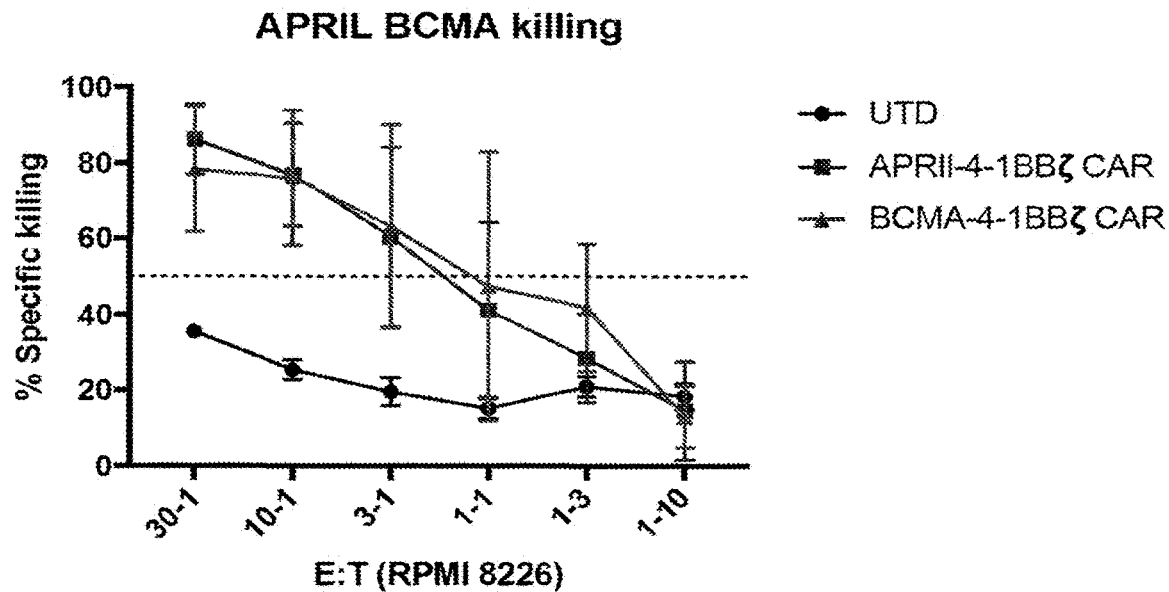
FIG. 6 depicts the results of a killing assay comparing APRIL and BCMA CARs.

CAR-transduced T cells were incubated for 18 hours with target BCMA+TACI+multiple cells (RMPI-8226) that had been transduced to express luciferase. Specific lysis of target cell was calculated at the indicated effector:target ratios (FIG. 6).

Figure 7:
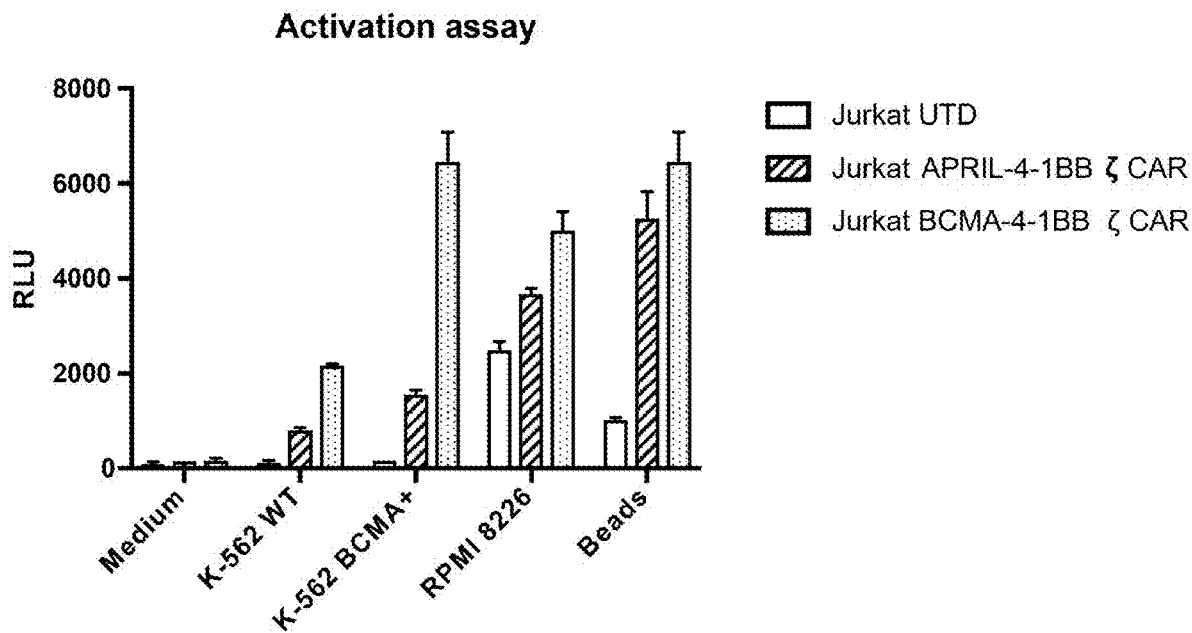
FIG. 7 depicts the results of an activation assay comparing APRIL and BCMA CARs. CAR-mediated T cell activation was tested in a Jurkat cell line expressing luciferase behind the NFAT promoter (JNL). JNL cells were lentivirally transduced with CARs as indicated and exposed to the targets indicated on the x-axis for several hours. Light emission was measured (relative Light units, y-axis).

CAR-mediated T cell activation was tested in a Jurkat cell line expressing luciferase behind the NFAT promoter (FIG. 7).

Example 4

Figure 8:
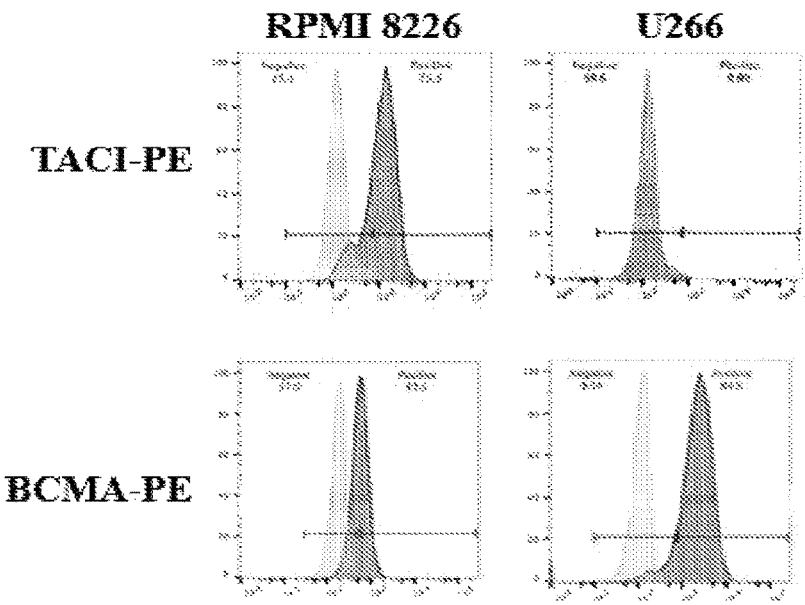
FIG. 8 depicts the level of expression of BCMA and TACI in the indicated multiple myeloma cell lines.
Figure 9:
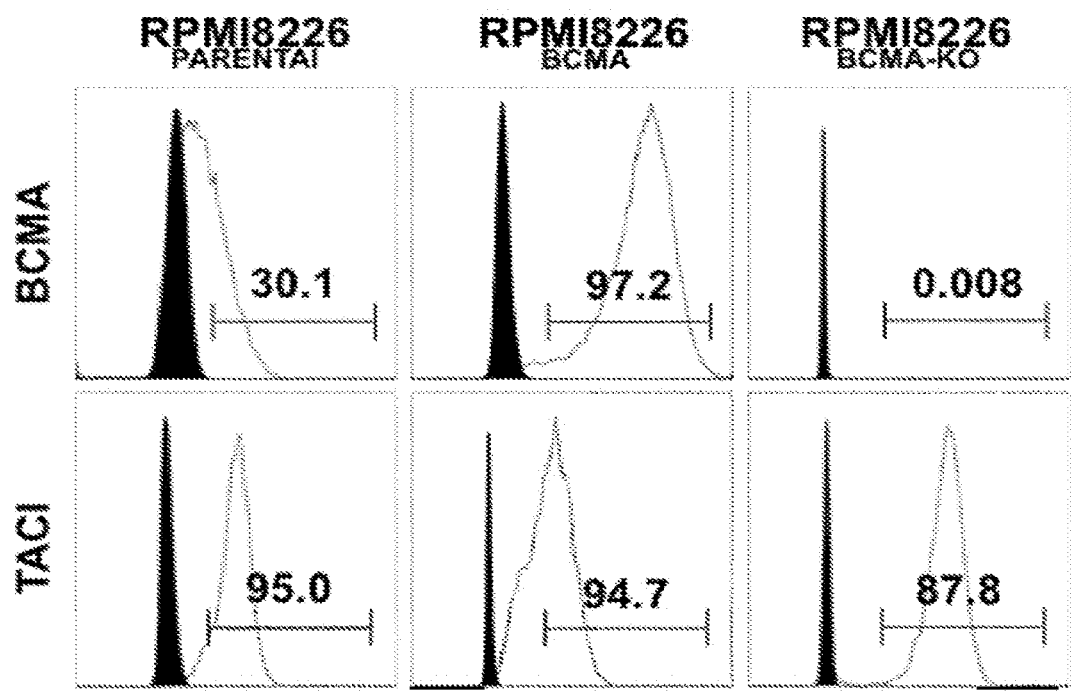
FIG. 9 depicts the expression of BCMA and TACI in engineered cell lines.

Surface expression of BCMA and TACI was measured in multiple myeloma cell lines (FIG. 8), and RPMI8226 was engineered to express various levels of BCMA (FIG. 9). TACI was transduced in to the RPMI-BCMA KO.

Figure 10:
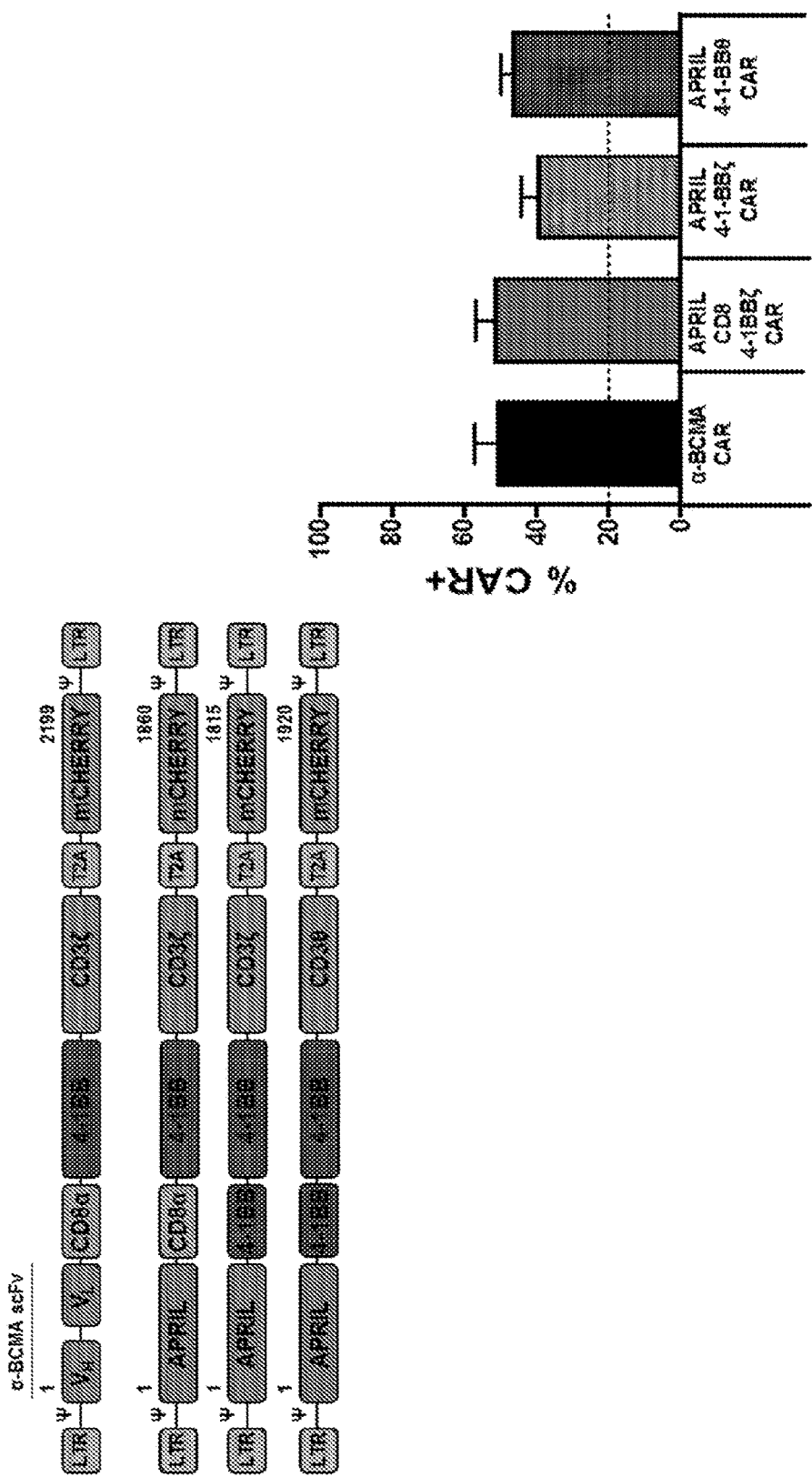
FIG. 10 depicts schematics of several APRIL and BCMA CARs and their transduction efficiencies.
Figure 11:
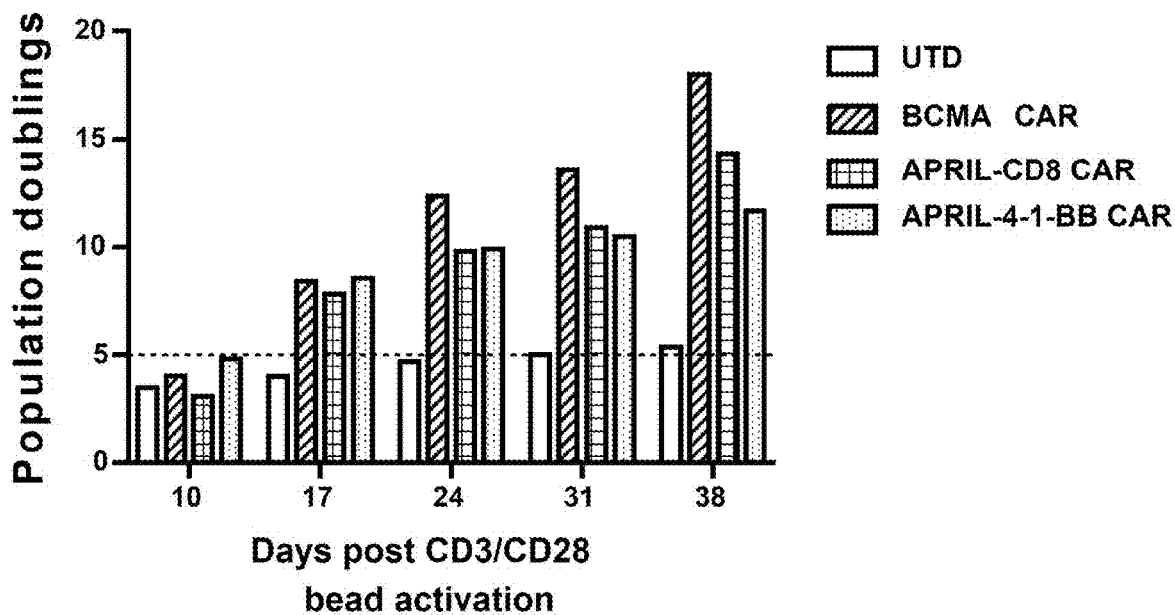
FIG. 11 depicts a graph demonstrating that BCMA and APRIL CARs expand upon repeated stimulation with RPMI8226BCMA
Figure 12:
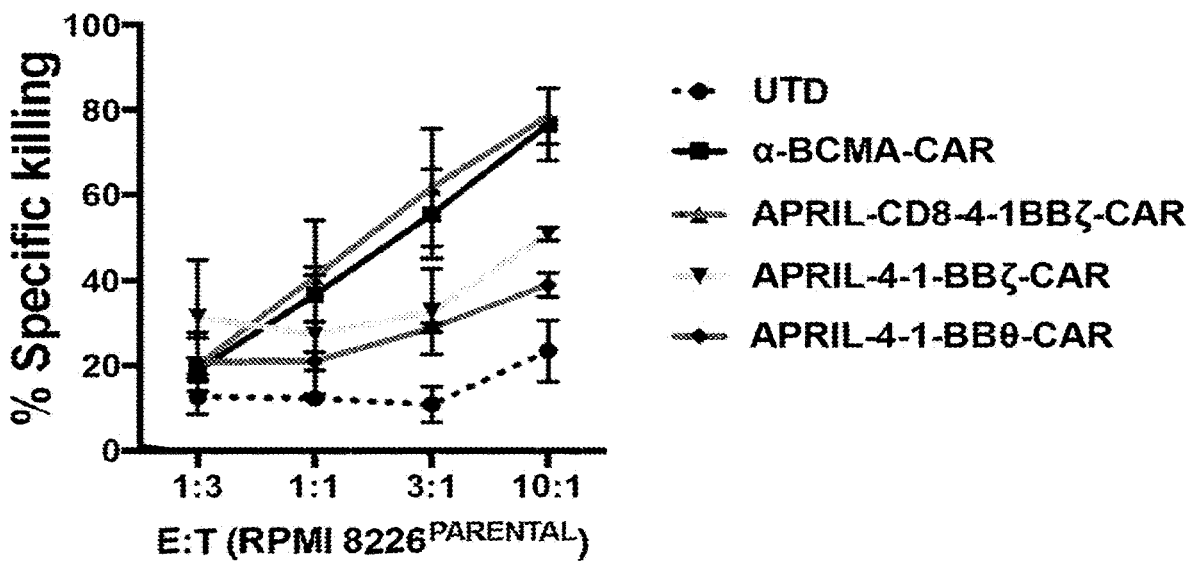
FIG. 12 depicts a graph of APRIL-CAR killing of BCMA and TACI expressing cell lines.
Figure 13:
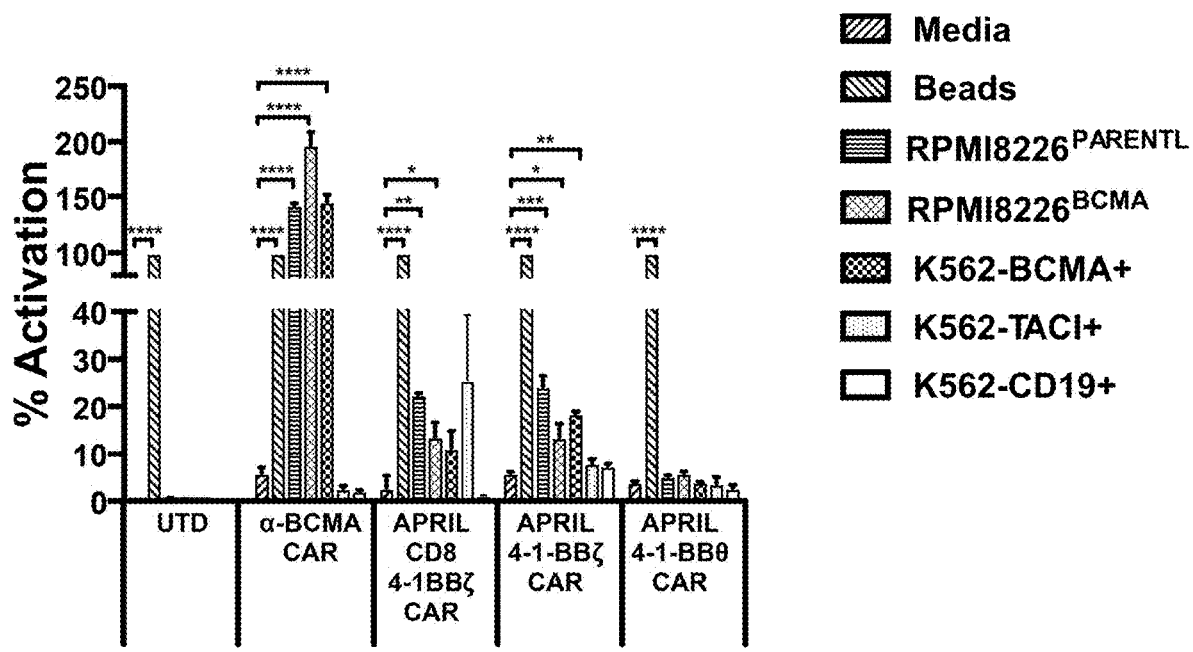
FIG. 13 depicts specific activation of APRIL-CAR.

A number of APRIL and BCMA CAR constructs were designed and demonstrated to effectively transduce T cells (FIG. 10). T cells expressing the CARs expanded upon stimulation with BCMA-expressing cells (FIG. 11). APRIL-CAR expressing T cells demonstrated specific killing of cells expressing BCMA and TACI (FIG. 12) and activation was similarly specific (FIG. 13).

Figure 14:
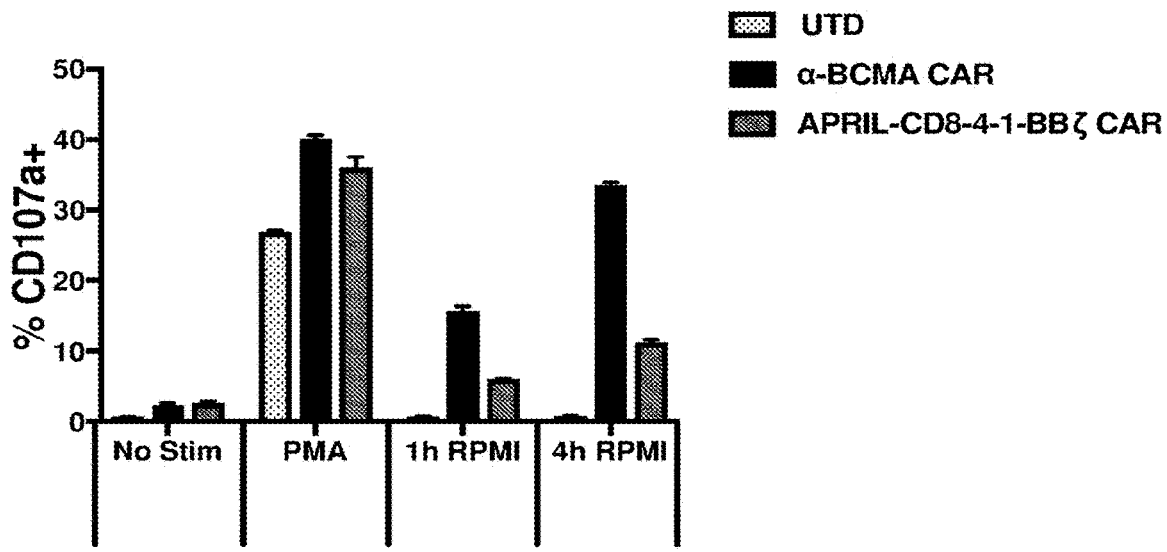
FIG. 14 demonstrates that BCMA and APRIL CARs degranulate in response to stimulation with RPMI8226PARENTAL
Figure 15A:
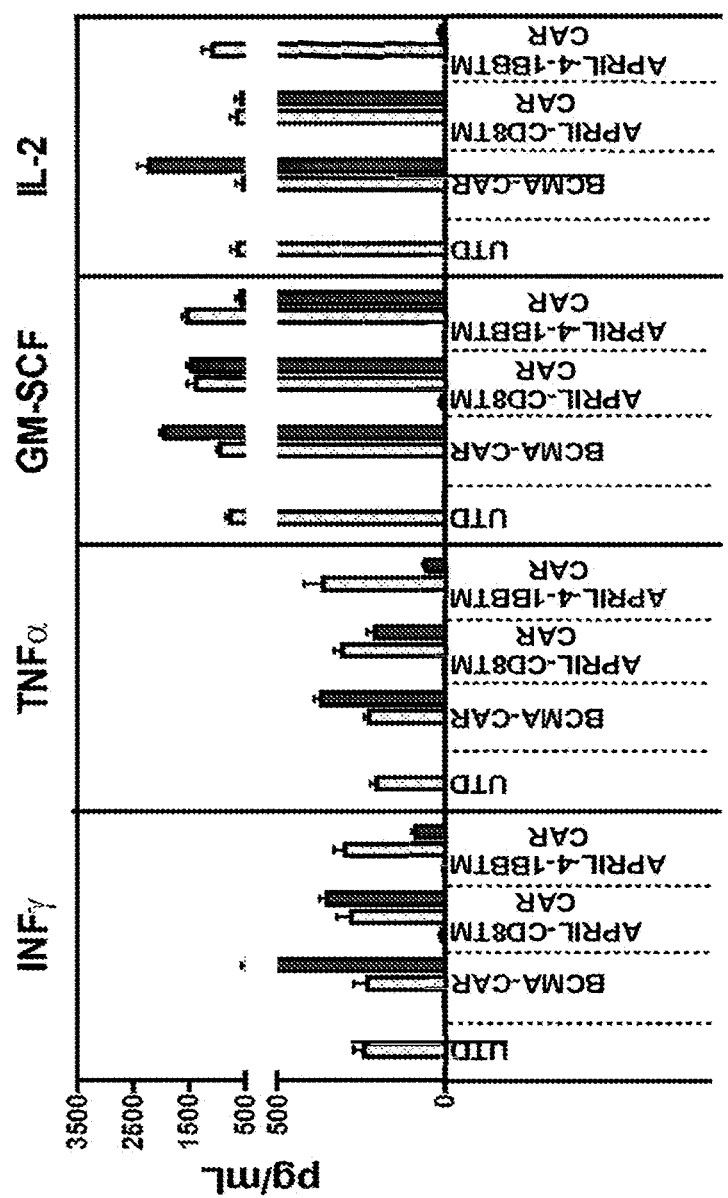
FIGS. 15A-15B depict the cytokine profile of APRIL-CART cells.
Figure 15B:
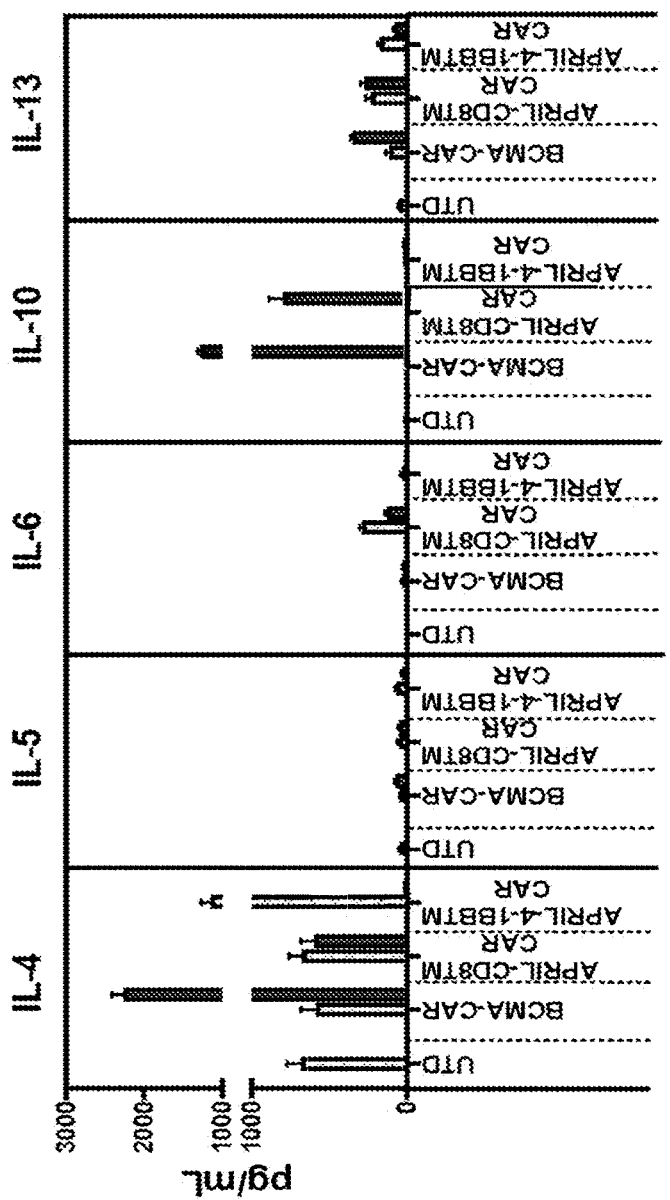

BCMA and APRIL CARs degranulate in response to stimulation with RPMI8226$^{PARENTAL}$ (FIG. 14). The cytokine profile of APRIL CARs is depicted in FIG. 15

Example 5—Construct Sequences pMGH71-APRIL/CD8TM/4-1BB/CD3ζ (SEQ ID NO: 1) comprises: CD8 leader (nucleotides 1-63 (SEQ ID NO: 2)); APRIL sequence (nucleotides 64-471 (SEQ ID NO: 3)); CD8 hinge and TM sequence (nucleotides 472-678 (SEQ ID NO: 4)); 4-1BB ICD sequence (nucleotides 679-804 (SEQ ID NO: 5)); and CD3 zeta sequence (nucleotides 805-1140 (SEQ ID NO: 6)).

```
(SEQ ID NO: 1)
ATGGCCCTCCCTGTCACCGCCCTGCTGCTTCCGCTGGCTCTTCTGCTCCA

CGCCGCTCGGCCCCACTCTGTCCTGCACCTGGTTCCCATTAACGCCACCT

CCAAGGATGACTCCGATGTGACAGAGGTGATGTGGCAACCAGCTCTTAGG

CGTGGGAGAGGCCTACAGGCCCAAGGATATGGTGTCCGAATCCAGGATGC

TGGAGTTTATCTGCTGTATAGCCAGGTCCTGTTTCAAGACGTGACTTTCA

CCATGGGTCAGGTGGTGTCTCGAGAAGGCCAAGGAAGGCAGGAGACTCTA

TTCCGATGTATAAGAAGTATGCCCTCCCACCCGGACCGGGCCTACAACAG
```

```
-continued
CTGCTATAGCGCAGGTGTCTTCCATTTACACCAAGGGGATATTCTGAGTG

TCATAATTCCCCGGGCAAGGGCGAAACTTAACCTCTCTCCACATGGAACC

TTCCTGGGGTTTGTGAAACTGACCACTACCCCAGCACCGAGGCCACCCAC

CCCGGCTCCTACCATCGCCTCCCAGCCTCTGTCCCTGCGTCCGGAGGCAT

GTAGACCCGCAGCTGGTGGGGCCGTGCATACCCGGGGTCTTGACTTCGCC

TGCGATATCTACATTTGGGCCCCTCTGGCTGGTACTTGCGGGGTCCTGCT

GCTTTCACTCGTGATCACTCTTTACTGTAAGCGCGGTCGGAAGAAGCTGC

TGTACATCTTTAAGCAACCCTTCATGAGGCCTGTGCAGACTACTCAAGAG

GAGGACGGCTGTTCATGCCGGTTCCCAGAGGAGGAGGAAGGCGGCTGCGA

ACTGCGCGTGAAATTCAGCCGCAGCGCAGATGCTCCAGCCTACCAACAGG

GGCAGAACCAGCTCTACAACGAACTCAATCTTGGTCGGAGAGAGGAGTAC

GACGTGCTGGACAAGCGGAGAGGACGGGACCCAGAAATGGGCGGGAAGCC

GCGCAGAAAGAATCCCCAAGAGGGCCTGTACAACGAGCTCCAAAAGGATA

AGATGGCAGAAGCCTATAGCGAGATTGGTATGAAAGGGGAACGCAGAAGA

GGCAAAGGCCACGACGGACTGTACCAGGGACTCAGCACCGCCACCAAGGA

CACCTATGACGCTCTTCACATGCAGGCCCTGCCGCCTCGG
```

CD8 leader (SEQ ID NO: 2 (nucleotides 1-63 of SEQ ID NO: 1))

```
(SEQ ID NO: 2)
ATGGCCCTCCCTGTCACCGCCCTGCTGCTTCCGCTGGCTCTTCTGCTCCA

CGCCGCTCGGCCC
```

APRIL sequence SEQ ID NO: 3 (nucleotides 64-471 of SEQ ID NO: 1)

```
(SEQ ID NO: 3)
CACTCTGTCCTGCACCTGGTTCCCATTAACGCCACCTCCAAGGATGACTC

CGATGTGACAGAGGTGATGTGGCAACCAGCTCTTAGGCGTGGGAGAGGCC

TACAGGCCCAAGGATATGGTGTCCGAATCCAGGATGCTGGAGTTTATCTG

CTGTATAGCCAGGTCCTGTTTCAAGACGTGACTTTCACCATGGGTCAGGT

GGTGTCTCGAGAAGGCCAAGGAAGGCAGGAGACTCTATTCCGATGTATAA

GAAGTATGCCCTCCCACCCGGACCGGGCCTACAACAGCTGCTATAGCGCA

GGTGTCTTCCATTTACACCAAGGGGATATTCTGAGTGTCATAATTCCCCG

GGCAAGGGCGAAACTTAACCTCTCTCCACATGGAACCTTCCTGGGGTTTG

TGAAACTG
```

CD8 hinge and TM sequence (SEQ ID NO: 4 (nucleotides 472-678 of SEQ ID NO: 1))

```
(SEQ ID NO: 4)
ACCACTACCCCAGCACCGAGGCCACCCACCCCGGCTCCTACCATCGCCTC

CCAGCCTCTGTCCCTGCGTCCGGAGGCATGTAGACCCGCAGCTGGTGGGG

CCGTGCATACCCGGGGTCTTGACTTCGCCTGCGATATCTACATTTGGGCC

CCTCTGGCTGGTACTTGCGGGGTCCTGCTGCTTTCACTCGTGATCACTCT

TTACTGT
```

4-1BB ICD sequence (SEQ ID NO: 5 (nucleotides 679-804 of SEQ ID NO: 1))

(SEQ ID NO: 5)
AAGCGCGGTCGGAAGAAGCTGCTGTACATCTTTAAGCAACCCTTCATGAG

GCCTGTGCAGACTACTCAAGAGGAGGACGGCTGTTCATGCCGGTTCCCAG

AGGAGGAGGAAGGCGGCTGCGAACTG

CD3 zeta sequence (SEQ ID NO: 6 (nucleotides 805-1140 of SEQ ID NO: 1))

(SEQ ID NO: 6)
CGCGTGAAATTCAGCCGCAGCGCAGATGCTCCAGCCTACCAACAGGGGCA

GAACCAGCTCTACAACGAACTCAATCTTGGTCGGAGAGAGGAGTACGACG

TGCTGGACAAGCGGAGAGGACGGGACCCAGAAATGGGCGGGAAGCCGCGC

AGAAAGAATCCCCAAGAGGGCCTGTACAACGAGCTCCAAAAGGATAAGAT

GGCAGAAGCCTATAGCGAGATTGGTATGAAAGGGGAACGCAGAAGAGGCA

AAGGCCACGACGGACTGTACCAGGGACTCAGCACCGCCACCAAGGACACC

TATGACGCTCTTCACATGCAGGCCCTGCCGCCTCGG pMGH76-APRIL/4-1BB™/4-1BB/CD3ζ (SEQ ID NO: 7) comprises CD8 leader (nucleotides 1-63 (SEQ ID NO: 8)); APRIL sequence (nucleotides 64-471 (SEQ ID NO: 9)); 4-1BB hinge and TM sequence (nucleotides 472-633 (SEQ ID NO: 10)); 4-1BB ICD sequence (nucleotides 634-759 (SEQ ID NO: 11)); CD3 zeta sequence (nucleotides 760-1095 (SEQ ID NO: 12)).

(SEQ ID NO: 7)
ATGGCCCTCCCTGTCACCGCCCTGCTGCTTCCGCTGGCTCTTCTGCT

CCACGCCGCTCGGCCCCACTCTGTCCTGCACCTGGTTCCCATTAACG

CCACCTCCAAGGATGACTCCGATGTGACAGAGGTGATGTGGCAACCA

GCTCTTAGGCGTGGGAGAGGCCTACAGGCCCAAGGATATGGTGTCCG

AATCCAGGATGCTGGAGTTTATCTGCTGTATAGCCAGGTCCTGTTTC

AAGACGTGACTTTCACCATGGGTCAGGTGGTGTCTCGAGAAGGCCAA

GGAAGGCAGGAGACTCTATTCCGATGTATAAGAAGTATGCCCTCCCA

CCCGGACCGGGCCTACAACAGCTGCTATAGCGCAGGTGTCTTCCATT

TACACCAAGGGGATATTCTGAGTGTCATAATTCCCCGGGCAAGGGCG

AAACTTAACCTCTCTCCACATGGAACCTTCCTGGGGTTTGTGAAACT

GCCATCTCCAGCCGACCTCTCTCCGGGAGCATCCTCTGTGACCCCGC

CTGCCCCTGCGAGAGAGCCAGGACACTCTCCGCAGATCATCTCCTTC

TTTCTTGCGCTGACGTCGACTGCGTTGCTCTTCCTGCTGTTCTTCCT

CACGCTCCGTTTCTCTGTTGTTAAGCGCGGTCGGAAGAAGCTGCTGT

ACATCTTTAAGCAACCCTTCATGAGGCCTGTGCAGACTACTCAAGAG

GAGGACGGCTGTTCATGCCGGTTCCCAGAGGAGGAGGAAGGCGGCTG

CGAACTGCGCGTGAAATTCAGCCGCAGCGCAGATGCTCCAGCCTACC

AACAGGGGCAGAACCAGCTCTACAACGAACTCAATCTTGGTCGGAGA

GAGGAGTACGACGTGCTGGACAAGCGGAGAGGACGGGACCCAGAAAT

GGGCGGGAAGCCGCGCAGAAAGAATCCCCAAGAGGGCCTGTACAACG

AGCTCCAAAAGGATAAGATGGCAGAAGCCTATAGCGAGATTGGTATG

AAAGGGGAACGCAGAAGAGGCAAAGGCCACGACGGACTGTACCAGGG

ACTCAGCACCGCCACCAAGGACACCTATGACGCTCTTCACATGCAGG

CCCTGCCGCCTCGG

CD8 leader sequence (SEQ ID NO: 8 (nucleotides 1-63 of SEQ ID NO: 7))

(SEQ ID NO: 8)
ATGGCCCTCCCTGTCACCGCCCTGCTGCTTCCGCTGGCTCTTCTGCT

CCACGCCGCTCGGCCC

APRIL sequence (SEQ ID NO: 9 (nucleotides 64-471 of SEQ ID NO: 7))

(SEQ ID NO: 9)
CACTCTGTCCTGCACCTGGTTCCCATTAACGCCACCTCCAAGGATGA

CTCCGATGTGACAGAGGTGATGTGGCAACCAGCTCTTAGGCGTGGGA

GAGGCCTACAGGCCCAAGGATATGGTGTCCGAATCCAGGATGCTGGA

GTTTATCTGCTGTATAGCCAGGTCCTGTTTCAAGACGTGACTTTCAC

CATGGGTCAGGTGGTGTCTCGAGAAGGCCAAGGAAGGCAGGAGACTC

TATTCCGATGTATAAGAAGTATGCCCTCCCACCCGGACCGGGCCTAC

AACAGCTGCTATAGCGCAGGTGTCTTCCATTTACACCAAGGGGATAT

TCTGAGTGTCATAATTCCCCGGGCAAGGGCGAAACTTAACCTCTCTC

CACATGGAACCTTCCTGGGGTTTGTGAAACTG 4-1BB hinge and TM sequence (SEQ ID NO: 10 (nucleotides 472-633 of SEQ ID NO: 7))

(SEQ ID NO: 10)
CCATCTCCAGCCGACCTCTCTCCGGGAGCATCCTCTGTGACCCCGCC

TGCCCCTGCGAGAGAGCCAGGACACTCTCCGCAGATCATCTCCTTCT

TTCTTGCGCTGACGTCGACTGCGTTGCTCTTCCTGCTGTTCTTCCTC

ACGCTCCGTTTCTCTGTTGTT 4-1BB ICD sequence (SEQ ID NO: 11 (nucleotides 634-759 of SEQ ID NO: 7))

(SEQ ID NO: 11)
AAGCGCGGTCGGAAGAAGCTGCTGTACATCTTTAAGCAACCCTTCAT

GAGGCCTGTGCAGACTACTCAAGAGGAGGACGGCTGTTCATGCCGGT

TCCCAGAGGAGGAGGAAGGCGGCTGCGAACTG

CD3 zeta sequence (SEQ ID NO: 12 (nucleotides 760-1095 of SEQ ID NO: 7))

(SEQ ID NO: 12)
CGCGTGAAATTCAGCCGCAGCGCAGATGCTCCAGCCTACCAACAGGG

GCAGAACCAGCTCTACAACGAACTCAATCTTGGTCGGAGAGAGGAGT

ACGACGTGCTGGACAAGCGGAGAGGACGGGACCCAGAAATGGGCGGG

AAGCCGCGCAGAAAGAATCCCCAAGAGGGCCTGTACAACGAGCTCCA pMGH77-APRIL/4-1BB™/4-1BB/CD3theta (SEQ ID NO: 13) comprising CD8 leader (nucleotides 1-63 (SEQ ID NO: 14)); APRIL sequence (nucleotides 64-471 (SEQ ID NO: 15)); 4-1BB hinge and TM sequence (nucleotides 472-633 (SEQ ID NO: 16)); 4-1BB ICD sequence (nucleotides 634-759 (SEQ ID NO: 17)); CD3 theta sequence (nucleotides 760-1200) (SEQ ID NO: 18)).

(SEQ ID NO: 13)
ATGGCCCTCCCTGTCACCGCCCTGCTGCTTCCGCTGGCTCTTCTGCT

CCACGCCGCTCGGCCCCACTCTGTCCTGCACCTGGTTCCCATTAACG

CCACCTCCAAGGATGACTCCGATGTGACAGAGGTGATGTGGCAACCA

GCTCTTAGGCGTGGGAGAGGCCTACAGGCCCAAGGATATGGTGTCCG

AATCCAGGATGCTGGAGTTTATCTGCTGTATAGCCAGGTCCTGTTTC

AAGACGTGACTTTCACCATGGGTCAGGTGGTGTCTCGAGAAGGCCAA

GGAAGGCAGGAGACTCTATTCCGATGTATAAGAAGTATGCCCTCCCA

CCCGGACCGGGCCTACAACAGCTGCTATAGCGCAGGTGTCTTCCATT

TACACCAAGGGGATATTCTGAGTGTCATAATTCCCCGGGCAAGGGCG

AAACTTAACCTCTCTCCACATGGAACCTTCCTGGGGTTTGTGAAACT

GCCATCTCCAGCCGACCTCTCTCCGGGAGCATCCTCTGTGACCCCGC

CTGCCCCTGCGAGAGAGCCAGGACACTCTCCGCAGATCATCTCCTTC

TTTCTTGCGCTGACGTCGACTGCGTTGCTCTTCCTGCTGTTCTTCCT

CACGCTCCGTTTCTCTGTTGTTAAGCGCGGTCGGAAGAAGCTGCTGT

ACATCTTTAAGCAACCCTTCATGAGGCCTGTGCAGACTACTCAAGAG

GAGGACGGCTGTTCATGCCGGTTCCCAGAGGAGGAGGAAGGCGGCTG

CGAACTGCGCGTGAAATTCAGCCGCAGCGCAGATGCTCCAGCCTACC

AACAGGGGCAGAACCAGCTCTACAACGAACTCAATCTTGGTCGGAGA

GAGGAGTACGACGTGCTGGACAAGCGGAGAGGACGGGACCCAGAAAT

GGGCGGGAAGCCGCGCAGAAAGAATCCCCAAGAGGGCCTGTACAACG

AGCTCCAAAAGGATAAGATGGCAGAAGCCTATAGCGAGATTGGTATG

AAAGGGAACGCAGAAGAGGCAAAGGCCACGACGGACTGTACCAGGA

CAGCCACTTCCAAGCAGTTCCAGTACAGGAAAAGAAAAAAGGCTCA

GAAGGGCACCGTGGCGTGCATTCGCCCAGCCCCAGAGGTTAAAGCAC

CGAAACAATGAACTACCTGACTCCCTAGAGCCCATATATAAAAACAT

TTGGAACAAAACATTTATAGGAGAG

CD8 leader sequence (SEQ ID NO: 14 (nucleotides 1-63 of SEQ ID NO: 13))

(SEQ ID NO: 14)
ATGGCCCTCCCTGTCACCGCCCTGCTGCTTCCGCTGGCTCTTCTGCT

CCACGCCGCTCGGCCC

APRIL sequence (SEQ ID NO: 15 (nucleotides 64-471 of SEQ ID NO: 13))

(SEQ ID NO: 15)
CACTCTGTCCTGCACCTGGTTCCCATTAACGCCACCTCCAAGGATGA

CTCCGATGTGACAGAGGTGATGTGGCAACCAGCTCTTAGGCGTGGGA

GAGGCCTACAGGCCCAAGGATATGGTGTCCGAATCCAGGATGCTGGA

GTTTATCTGCTGTATAGCCAGGTCCTGTTTCAAGACGTGACTTTCAC

CATGGGTCAGGTGGTGTCTCGAGAAGGCCAAGGAAGGCAGGAGACTC

TATTCCGATGTATAAGAAGTATGCCCTCCCACCCGGACCGGGCCTAC

AACAGCTGCTATAGCGCAGGTGTCTTCCATTTACACCAAGGGGATAT

TCTGAGTGTCATAATTCCCCGGGCAAGGGCGAAACTTAACCTCTCTC

CACATGGAACCTTCCTGGGGTTTGTGAAACTG 4-1BB hinge and TM sequence (SEQ ID NO: 16 (nucleotides 472-633 of SEQ ID NO: 13))

(SEQ ID NO: 16)
CCATCTCCAGCCGACCTCTCTCCGGGAGCATCCTCTGTGACCCCGCC

TGCCCCTGCGAGAGAGCCAGGACACTCTCCGCAGATCATCTCCTTCT

TTCTTGCGCTGACGTCGACTGCGTTGCTCTTCCTGCTGTTCTTCCTC

ACGCTCCGTTTCTCTGTTGTT 4-1BB ICD sequence (SEQ ID NO: 17 (nucleotides 634-759 SEQ ID NO: 13))

(SEQ ID NO: 17)
AAGCGCGGTCGGAAGAAGCTGCTGTACATCTTTAAGCAACCCTTCAT

GAGGCCTGTGCAGACTACTCAAGAGGAGGACGGCTGTTCATGCCGGT

TCCCAGAGGAGGAGGAAGGCGGCTGCGAACTG

CD3 theta sequence (SEQ ID NO: 18 (nucleotides 760-1200 of SEQ ID NO: 13))

(SEQ ID NO: 18)
CGCGTGAAATTCAGCCGCAGCGCAGATGCTCCAGCCTACCAACAGGG

GCAGAACCAGCTCTACAACGAACTCAATCTTGGTCGGAGAGAGGAGT

ACGACGTGCTGGACAAGCGGAGAGGACGGGACCCAGAAATGGGCGGG

AAGCCGCGCAGAAAGAATCCCCAAGAGGGCCTGTACAACGAGCTCCA

AAAGGATAAGATGGCAGAAGCCTATAGCGAGATTGGTATGAAAGGGG

AACGCAGAAGAGGCAAAGGCCACGACGGACTGTACCAGGACAGCCAC

TTCCAAGCAGTTCCAGTACAGGAAAAGAAAAAAAGGCTCAGAAGGGC

ACCGTGGCGTGCATTCGCCCAGCCCCAGAGGTTAAAGCACCGAAACA

ATGAACTACCTGACTCCCTAGAGCCCATATATAAAAACATTTGGAAC

AAAACATTTATAGGAGAG

Example 6

As described elsewhere herein, specific residues are involved in binding to BCMA/TACI, namely: D132, T175, D205, R206, R231 of APRIL. The location of those residues are depicted below with bold type.

pMGH71-CD8Leader/APRIL/CD8hinge+TM/4-1BB/ CD3z (SEQ ID NO: 19) comprising CD8 leader (amino acids 1-21 (SEQ ID NO: 20)); APRIL sequence (amino acids 22-157 (SEQ ID NO: 21)); CD8 hinge and TM sequence (amino acids 158-226 (SEQ ID NO: 22)); 4-1BB ICD sequence (amino acids 227-268 (SEQ ID NO: 23)); CD3 zeta sequence (amino acids 269-380) (SEQ ID NO: 24)).

(SEQ ID NO: 19)
MALPVTALLLPLALLLHAARPHSVLHLVPINATSKDDSDVTEVMWQP

ALRRGRGLQAQGYGVRIQDAGVYLLYSQVLFQDVTFTMGQVVSREGQ

GRQETLFRCIRSMPSHPDRAYNSCYSAGVFHLHQGDILSVIIPRARA

KLNLSPHGTFLGFVKLTTTPAPRPPTPAPTIASQPLSLRPEACRPAA

GGAVHTRGLDFACDIYIWAPLAGTCGVLLLSLVITLYCKRGRKKLLY

IFKQPFMRPVQTTQEEDGCSCRFPEEEEGGCELRVKFSRSADAPAYQ

QGQNQLYNELNLGRREEYDVLDKRRGRDPEMGGKPRRKNPQEGLYNE

LQKDKMAEAYSEIGMKGERRRGKGHDGLYQGLSTATKDTYDALHMQA

LPPR

CD8 leader sequence (SEQ ID NO: 20 (amino acids 1-21 of SEQ ID NO: 19))

(SEQ ID NO: 20)
MALPVTALLLPLALLLHAARP

APRIL sequence (SEQ ID NO: 21 (amino acids 22-157 of SEQ ID NO: 19))

(SEQ ID NO: 21)
HSVLHLVPINATSKDDSDVTEVMWQPALRRGRGLQAQGYGVRIQDAG

VYLLYSQVLFQDVTFTMGQVVSREGQGRQETLFRCIRSMPSHPDRAY

NSCYSAGVFHLHQGDILSVIIPRARAKLNLSPHGTFLGFVKL

CD8 hinge and TM sequence (SEQ ID NO: 22 (amino acids 158-226 of SEQ ID NO: 19))

(SEQ ID NO: 22)
TTTPAPRPPTPAPTIASQPLSLRPEACRPAAGGAVHTRGLDFACDIY

IWAPLAGTCGVLLLSLVITLYC 4-1BB ICD sequence (SEQ ID NO: 23 (amino acids 227-268 of SEQ ID NO: 19))

(SEQ ID NO: 23)
KRGRKKLLYIFKQPFMRPVQTTQEEDGCSCRFPEEEEGGCEL

CD3 zeta sequence (SEQ ID NO: 24 (amino acids 269-380 of SEQ ID NO: 19))

(SEQ ID NO: 24)
RVKFSRSADAPAYQQGQNQLYNELNLGRREEYDVLDKRRGRDPEMGG

KPRRKNPQEGLYNELQKDKMAEAYSEIGMKGERRRGKGHDGLYQGLS

TATKDTYDALHMQALPPR pMGH76-CD8Leader/APRIL/4-1BBhinge+TM/4-1BB/ CD3z (SEQ ID NO: 25) comprises CD8 leader (amino acids 1-21 (SEQ ID NO: 26)); APRIL sequence (amino acids 22-157 (SEQ ID NO: 27)); 4-1BB hinge and TM sequence (amino acids 158-211 (SEQ ID NO: 28)); 4-1BB ICD sequence (amino acids 212-253 (SEQ ID NO: 29)); CD3 zeta sequence (amino acids 254-365 (SEQ ID NO: 30)).

(SEQ ID NO: 25)
MALPVTALLLPLALLLHAARPHSVLHLVPINATSKDDSDVTEVMWQP

ALRRGRGLQAQGYGVRIQDAGVYLLYSQVLFQDVTFTMGQVVSREGQ

GRQETLFRCIRSMPSHPDRAYNSCYSAGVFHLHQGDILSVIIPRARA

KLNLSPHGTFLGFVKLPSPADLSPGASSVTPPAPAREPGHSPQIISF

FLALTSTALLFLLFFLTLRFSVVKRGRKKLLYIFKQPFMRPVQTTQE

EDGCSCRFPEEEEGGCELRVKFSRSADAPAYQQGQNQLYNELNLGRR

EEYDVLDKRRGRDPEMGGKPRRKNPQEGLYNELQKDKMAEAYSEIGM

KGERRRGKGHDGLYQGLSTATKDTYDALHMQALPPR

CD8 leader sequence (SEQ ID NO: 26 (amino acids 1-21 of SEQ ID NO: 25))

(SEQ ID NO: 26)
MALPVTALLLPLALLLHAARP

APRIL sequence (SEQ ID NO: 27 (amino acids 22-157 of SEQ ID NO: 25))

(SEQ ID NO: 27)
HSVLHLVPINATSKDDSDVTEVMWQPALRRGRGLQAQGYGVRIQDAG

VYLLYSQVLFQDVTFTMGQVVSREGQGRQETLFRCIRSMPSHPDRAY

NSCYSAGVFHLHQGDILSVIIPRARAKLNLSPHGTFLGFVKL 4-1BB hinge and TM sequence (SEQ ID NO: 28 (amino acids 158-211 of SEQ ID NO: 25))

(SEQ ID NO: 28)
PSPADLSPGASSVTPPAPAREPGHSPQIISFFLALTSTALLFLLFFL

TLRFSVV 4-1BB ICD sequence (SEQ ID NO: 29 (amino acids 212-253 of SEQ ID NO: 25))

(SEQ ID NO: 29)
KRGRKKLLYIFKQPFMRPVQTTQEEDGCSCRFPEEEEGGCEL

CD3 zeta sequence (SEQ ID NO: 30 (amino acids 254-365 of SEQ ID NO: 25)

(SEQ ID NO: 30)
RVKFSRSADAPAYQQGQNQLYNELNLGRREEYDVLDKRRGRDPEMGG

KPRRKNPQEGLYNELQKDKMAEAYSEIGMKGERRRGKGHDGLYQGLS

TATKDTYDALHMQALPPR pMGH77-CD8Leader/APRIL/4-1BBhinge+TM/4-1BB/ CD3theta (SEQ ID NO: 31) comprises CD8 leader (amino acids 1-21 (SEQ ID NO: 32)); APRIL sequence (amino acids 22-157 (SEQ ID NO: 33)); 4-1BB hinge and TM sequence (amino acids 158-211 (SEQ ID NO: 34)); 4-1BB ICD sequence (amino acids 212-253 (SEQ ID NO: 35)); CD3 theta sequence (amino acids 254-400) (SEQ ID NO: 36)).

(SEQ ID NO: 31)
MALPVTALLLPLALLLHAARPHSVLHLVPINATSKDDSDVTEVMWQP

ALRRGRGLQAQGYGVRIQDAGVYLLYSQVLFQDVTFTMGQVVSREGQ

GRQETLFRCIRSMPSHPDRAYNSCYSAGVFHLHQGDILSVIIPRARA

KLNLSPHGTFLGFVKLPSPADLSPGASSVTPPAPAREPGHSPQIISF

FLALTSTALLFLLFFLTLRFSVVKRGRKKLLYIFKQPFMRPVQTTQE

EDGCSCRFPEEEEGGCELRVKFSRSADAPAYQQGQNQLYNELNLGRR

EEYDVLDKRRGRDPEMGGKPRRKNPQEGLYNELQKDKMAEAYSEIGM

KGERRRGKGHDGLYQDSHFQAVPVQEKKKRLRRAPWRAFAQPQRLKH

RNNELPDSLEPIYKNIWNKTFIGE

CD8 leader sequence (SEQ ID NO: 32 (amino acids 1-21 of SEQ ID NO: 31))

(SEQ ID NO: 32)
MALPVTALLLPLALLLHAARP

APRIL sequence (SEQ ID NO: 33 (amino acids 22-157 of SEQ ID NO: 31))

(SEQ ID NO: 33)
HSVLHLVPINATSKDDSDVTEVMWQPALRRGRGLQAQGYGVRIQDAG

VYLLYSQVLFQDVTFTMGQVVSREGQGRQETLFRCIRSMPSHPDRAY

NSCYSAGVFHLHQGDILSVIIPRARAKLNLSPHGTFLGFVKL 4-1BB hinge and TM sequence (SEQ ID NO: 34 (amino acids 158-211 of SEQ ID NO: 31))

(SEQ ID NO: 34)
PSPADLSPGASSVTPPAPAREPGHSPQIISFFLALTSTALLFLLFFL

TLRFSVV 4-1BB ICD sequence (SEQ ID NO: 35 (amino acids 212-253 of SEQ ID NO: 31))

(SEQ ID NO: 35)
KRGRKKLLYIFKQPFMRPVQTTQEEDGCSCRFPEEEEGGCEL

CD3 theta sequence (SEQ ID NO: 36 (amino acids 254-400 of SEQ ID NO: 31))

(SEQ ID NO: 36)
RVKFSRSADAPAYQQGQNQLYNELNLGRREEYDVLDKRRGRDPEMGG

KPRRKNPQEGLYNELQKDKMAEAYSEIGMKGERRRGKGHDGLYQDSH

FQAVPVQEKKKRLRRAPWRAFAQPQRLKHRNNELPDSLEPIYKNIWN

KTFIGE

Example 7

Ligand Oligomerization to Enhance CARs Targeting Multimeric Antigens

In the work described in this study, natural oligomerization (e.g., homotrimerization) was used to develop ligand-based CARs with increased activity against cells expressing their cognate receptor. Certain ligands for cell surface receptors, including ligands of the TNF superfamily, are known to oligomerize (e.g., trimerize) to bind their cognate receptor. For example, as described above, human myeloma is known to express two surface antigens that may be targeted for effective antitumor antigens: BCMA and TACI. BCMI and TACI share a common ligand, APRIL, which is a compact self-forming trimer which binds with nanomolar affinity to TACI and BCMA.

A homotrimeric APRIL CAR construct was designed and constructed (FIG. 16). This construct is referred to herein as "TriPRIL CAR" and includes three tandem APRIL polypeptides connected through linkers, a CD8 hinge/transmembrane domain (CD8 TM), a 4-1BB intracellular domain (4-1BB), and a CD3ζ intracellular domain (CD3ζ). This construct is operably linked to a promoter (e.g., an EFla promoter).

Figure 17:
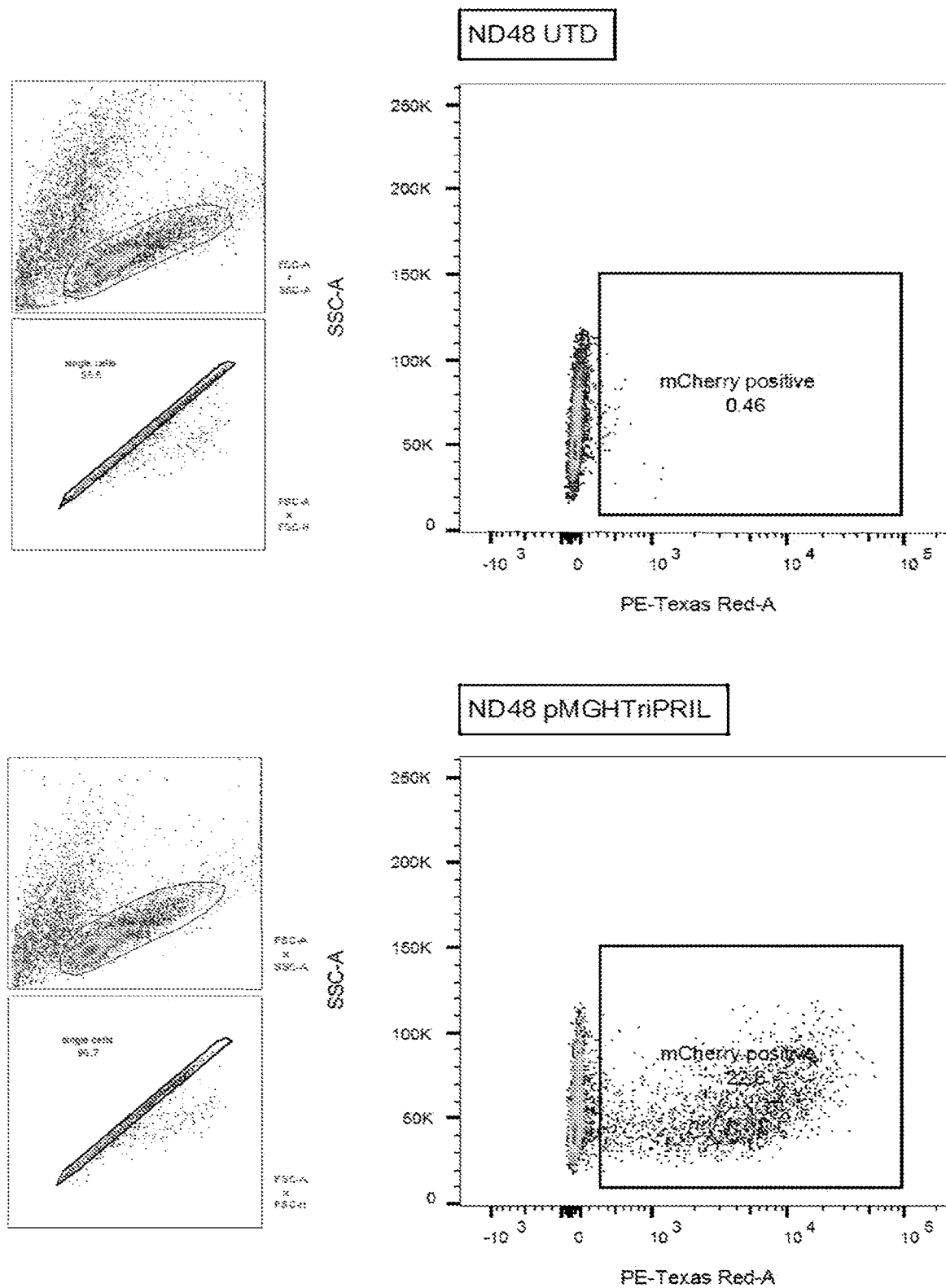
FIG. 17 depicts CAR-T cell transduction efficiency of TriPRIL CAR. The X-axis shows mCherry signal, and the y-axis is side scatter. The top panel shows control untransduced (UTD) cells, and the bottom panel shows cells transduced with the TriPRIL CAR.

The transduction efficiency of the TriPRIL CAR construct into primary human T cells was evaluated (FIG. 17). Approximately 22.6% of the cells were mCherry-positive, compared to approximately 0.46% for the untransduced control. Therefore, the TriPRIL CAR construct can be transduced into primary human T cells.

Figure 18:
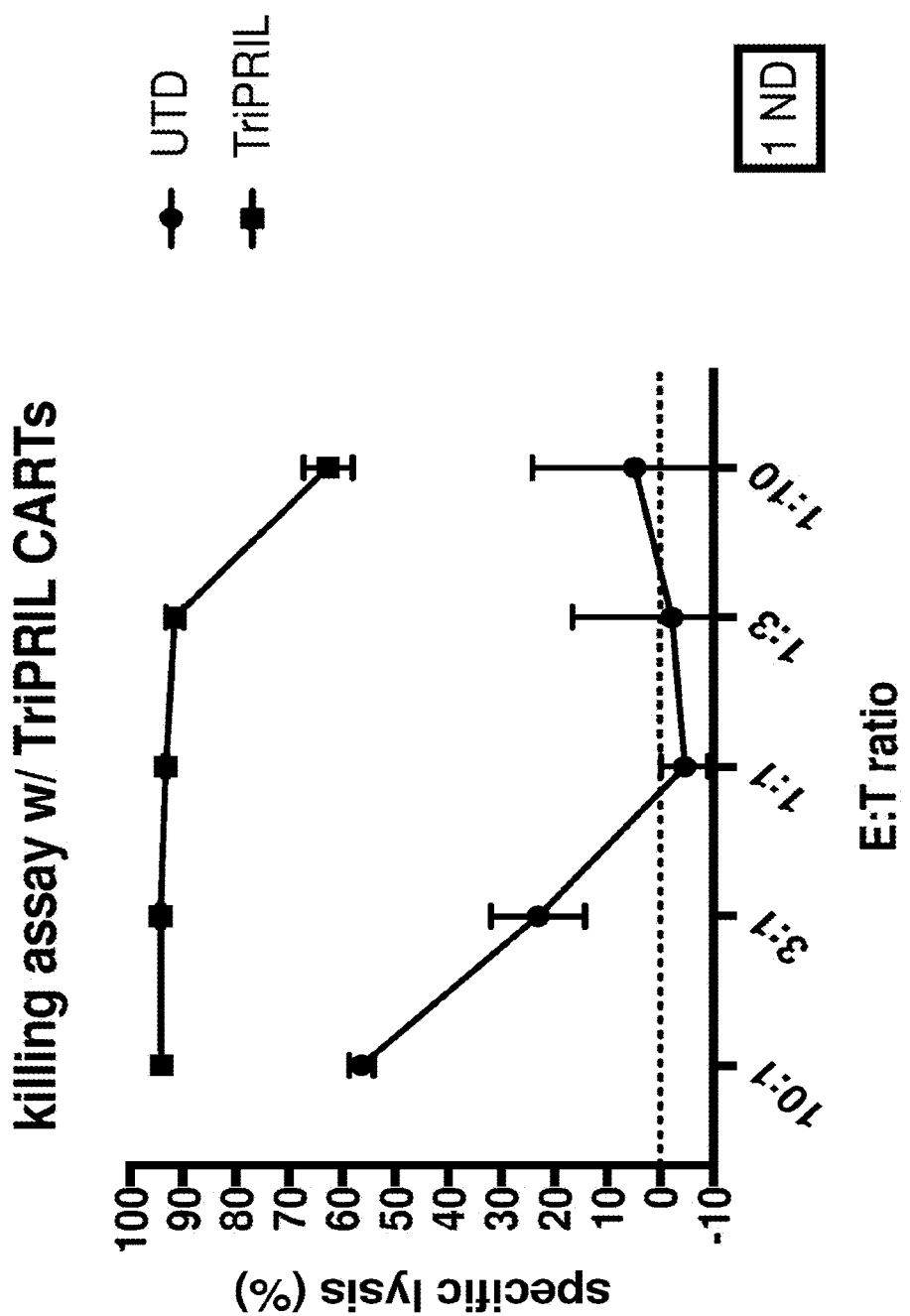
FIG. 18 depicts the results of a cell killing assay using TriPRIL CAR T cells.

TriPRIL CAR expressing T cells demonstrated specific killing of cells expressing BCMA and TACI (FIG. 18). Therefore, TriPRIL CARs are useful therapeutic agents for treatment of tumors expressing BCMA, TACI, and/or BAFF-receptor, e.g., myeloma.

Analogous CAR constructs using other self-oligomerizing ligands (e.g., TNF superfamily ligands (e.g., TNF-alpha, lymphotoxin beta, OX40L, CD154, FasL, LIGHT, TLIA, CD70, Siva, CD153, 4-1BB ligand, TRAIL, RANKL, TWEAK, BAFF, CAMLG, LIGHT, NGF, BDNF, NT-3, NT-4, GITR ligand, TLIA, or EDA-A2)) can be used to target killing of unwanted cells expressing the cognate receptor, e.g., tumor cells.

What is claimed herein is:

1. A CAR polypeptide comprising a sequence corresponding to a sequence selected from SEQ ID NO: 25 or 31, or that is encoded by a sequence selected from SEQ ID NO: 7 or 13.

2. A polypeptide complex comprising two or more of the CAR polypeptides of claim 1.

3. The polypeptide complex of claim 2, wherein the polypeptide complex comprises three CAR polypeptides.

4. A mammalian cell comprising;
   (a) the CAR polypeptide of claim 1;
   (b) a nucleic acid encoding the CAR polypeptide; or (c) a polypeptide complex comprising two or more of the CAR polypeptides.

5. A method of treating cancer expressing a cognate receptor of APRIL in a subject, the method comprising:
   a) engineering a T cell to comprise the CAR of claim 1 on the T cell surface; and
   b) administering an effective amount of the engineered T cell to the subject.

6. A method of treating cancer expressing a cognate receptor of APRIL in a subject, the method comprising administering an effective amount of an engineered T cell comprising the CAR of claim 1 to the subject.

7. The method of claim 6, wherein the cancer is B-cell activating factor receptor positive (BAFF-receptor+), B-cell maturation antigen positive (BCMA+) and/or transmembrane activator calcium modulator and cyclophilin ligand interactor positive (TACI+).

8. The method of claim 7, wherein the cancer is BAFF-receptor+.

9. The method of claim 7, wherein the cancer is BCMA+.

10. The method of claim 7, wherein the cancer is TACI+.

11. The method of claim 6, wherein the cancer is a B cell malignancy, leukemia, lymphoma, or multiple myeloma.

12. The method of claim 11, wherein the cancer is a leukemia.

13. The method of claim 12, wherein the leukemia is chronic lymphocytic leukemia.

14. The method of claim 11, wherein the cancer is a lymphoma.

15. The method of claim 11, wherein the cancer is a multiple myeloma.

16. The method of claim 11, wherein the cancer is a B cell malignancy.

17. The mammalian cell of claim 4, wherein the cell is an immune cell.

18. The mammalian cell of the claim 4, wherein the cell is a T cell.

* * * * *